US012575772B2

(12) United States Patent
Bullington et al.

(10) Patent No.: US 12,575,772 B2
(45) Date of Patent: *Mar. 17, 2026

(54) DEVICES AND METHODS FOR BODILY FLUID COLLECTION AND DISTRIBUTION

(71) Applicant: Magnolia Medical Technologies, Inc., Seattle, WA (US)

(72) Inventors: Gregory J. Bullington, Seattle, WA (US); Jeff Allison, Lake Oswego, OR (US); Brian Shay, Seattle, WA (US); Joshua D. Maruska, Seattle, WA (US); John Andrew Johnson, Bainbridge Island, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,178

(22) Filed: Aug. 30, 2023

(65) Prior Publication Data

US 2024/0057908 A1     Feb. 22, 2024

Related U.S. Application Data

(63) Continuation of application No. 16/785,170, filed on Feb. 7, 2020, now Pat. No. 11,786,155.

(60) Provisional application No. 62/802,999, filed on Feb. 8, 2019.

(51) Int. Cl.
  *A61B 5/15*        (2006.01)
  *A61B 10/00*      (2006.01)
(52) U.S. Cl.
  CPC .... *A61B 5/150251* (2013.01); *A61B 10/0048* (2013.01); *A61B 10/0051* (2013.01); *A61B 10/007* (2013.01); *A61B 2010/0077* (2013.01)
(58) Field of Classification Search
  None
  See application file for complete search history.

(56) References Cited

U.S. PATENT DOCUMENTS

| | | |
|---|---|---|
| 2,674,265 A | 4/1954 | Lee |
| 2,697,435 A | 12/1954 | Benjamin |
| 2,707,953 A | 5/1955 | Ryan |
| 2,876,769 A | 3/1959 | Cordova |
| 2,952,258 A | 9/1960 | Chandler |
| 2,992,974 A | 7/1961 | Belcove et al. |
| 3,013,557 A | 12/1961 | Pallotta |
| 3,098,016 A | 7/1963 | Sam et al. |
| 3,382,865 A | 5/1968 | Worrall, Jr. |
| 3,405,706 A | 10/1968 | Paul |
| 3,467,021 A | 9/1969 | Green, Jr. |
| 3,467,095 A | 9/1969 | Ross |
| 3,494,351 A | 2/1970 | Horn |
| 3,494,352 A | 2/1970 | Russo et al. |

| | | |
|---|---|---|
| 3,577,980 A | 5/1971 | Cohen |
| 3,596,652 A | 8/1971 | Winkelman |
| 3,604,410 A | 9/1971 | Whitacre |
| 3,635,798 A | 1/1972 | Kirkham et al. |
| 3,640,267 A | 2/1972 | Hurtig et al. |
| 3,648,684 A | 3/1972 | Barnwell et al. |
| 3,650,093 A | 3/1972 | Rosenberg |
| 3,680,558 A | 8/1972 | Kapelowitz |
| 3,696,806 A | 10/1972 | Sausse |
| 3,705,018 A | 12/1972 | Taylor |
| 3,730,168 A | 5/1973 | McWhorter |
| 3,741,197 A | 6/1973 | Sanz et al. |
| 3,777,773 A | 12/1973 | Tolbert |
| 3,779,383 A | 12/1973 | Ayres |
| 3,803,810 A | 4/1974 | Rosenberg |
| 3,817,240 A | 6/1974 | Ayres |
| 3,831,602 A | 8/1974 | Broadwin |
| 3,834,372 A | 9/1974 | Turney |
| 3,835,835 A | 9/1974 | Thompson et al. |
| 3,848,579 A | 11/1974 | Villa |
| 3,848,581 A | 11/1974 | Cinqualbre et al. |
| 3,859,998 A | 1/1975 | Thomas et al. |
| 3,874,367 A | 4/1975 | Ayres |
| 3,886,930 A | 6/1975 | Ryan |
| 3,890,203 A | 6/1975 | Mehl |
| 3,890,968 A | 6/1975 | Pierce et al. |
| 3,937,211 A | 2/1976 | Merten |
| 3,943,917 A | 3/1976 | Johansen |
| 3,945,380 A | 3/1976 | Dabney et al. |
| 3,960,139 A | 6/1976 | Bailey |
| 3,978,846 A | 9/1976 | Bailey |

(Continued)

FOREIGN PATENT DOCUMENTS

| | | |
|---|---|---|
| AT | 310345 B | 9/1973 |
| AU | 736156 B2 | 7/2001 |

(Continued)

OTHER PUBLICATIONS

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.

(Continued)

*Primary Examiner* — Ann Montgomery
(74) *Attorney, Agent, or Firm* — Cooley LLP

(57)           ABSTRACT

An apparatus includes a housing that defines a fluid reservoir and includes a port that is in fluid communication with the fluid reservoir. An inlet adapter is removably coupleable to the housing. A user can engage an actuator to move a plunger from a first position in which the fluid reservoir has a first volume, to a second position in which the fluid reservoir has a second volume greater than the first volume, which draws bodily fluid into the fluid reservoir via the inlet adapter. The actuator modulates a plunger rate of motion below a threshold as the plunger is moved. When a predetermined volume of bodily fluid is transferred into the fluid reservoir, a volume indicator transitions from a first state to a second state and the inlet adapter can then be removed to transfer the predetermined volume into a sample bottle external to the housing via the port.

19 Claims, 28 Drawing Sheets

(56)                 References Cited

U.S. PATENT DOCUMENTS

| | | |
|---|---|---|
| 3,996,923 A | 12/1976 | Guerra |
| 4,056,101 A | 11/1977 | Geissler et al. |
| 4,057,050 A | 11/1977 | Sarstedt |
| 4,062,360 A | 12/1977 | Bentley |
| 4,063,460 A | 12/1977 | Svensson |
| 4,077,395 A | 3/1978 | Woolner |
| 4,106,491 A | 8/1978 | Guerra |
| 4,106,497 A | 8/1978 | Percarpio |
| 4,133,304 A | 1/1979 | Bailey |
| 4,133,863 A | 1/1979 | Koenig |
| 4,150,089 A | 4/1979 | Linet |
| 4,154,229 A | 5/1979 | Nugent |
| 4,166,450 A | 9/1979 | Abramson |
| 4,190,426 A | 2/1980 | Ruschke |
| 4,193,400 A | 3/1980 | Loveless et al. |
| 4,202,764 A | 5/1980 | Afflerbaugh et al. |
| 4,206,282 A | 6/1980 | Hochstein |
| 4,207,870 A | 6/1980 | Eldridge |
| 4,210,173 A | 7/1980 | Choksi et al. |
| 4,212,308 A | 7/1980 | Percarpio |
| 4,226,236 A | 10/1980 | Genese |
| 4,238,207 A | 12/1980 | Ruschke |
| 4,257,416 A | 3/1981 | Prager |
| 4,275,730 A | 6/1981 | Hussein |
| 4,298,358 A | 11/1981 | Ruschke |
| 4,312,362 A | 1/1982 | Kaufman |
| 4,317,456 A | 3/1982 | Percarpio |
| 4,327,746 A | 5/1982 | Feaster |
| 4,340,067 A | 7/1982 | Rattenborg |
| 4,340,068 A | 7/1982 | Kaufman |
| 4,349,035 A | 9/1982 | Thomas et al. |
| 4,354,507 A | 10/1982 | Raitto |
| 4,370,987 A | 2/1983 | Bazell et al. |
| 4,373,535 A | 2/1983 | Martell |
| 4,398,544 A | 8/1983 | Nugent et al. |
| 4,411,275 A | 10/1983 | Raitto |
| 4,412,548 A | 11/1983 | Hoch |
| 4,416,290 A | 11/1983 | Lutkowski |
| 4,416,291 A | 11/1983 | Kaufman |
| 4,425,235 A | 1/1984 | Cornell et al. |
| 4,436,098 A | 3/1984 | Kaufman |
| 4,444,203 A | 4/1984 | Engelman |
| 4,459,997 A | 7/1984 | Sarstedt |
| 4,496,458 A | 1/1985 | Lee |
| 4,509,534 A | 4/1985 | Tassin, Jr. |
| 4,551,131 A | 11/1985 | Miles et al. |
| 4,581,014 A | 4/1986 | Millerd et al. |
| 4,608,996 A | 9/1986 | Brown |
| 4,626,248 A | 12/1986 | Scheller |
| 4,654,027 A | 3/1987 | Dragan et al. |
| 4,657,027 A | 4/1987 | Paulsen |
| 4,657,160 A | 4/1987 | Woods et al. |
| 4,673,386 A | 6/1987 | Gordon |
| 4,676,256 A | 6/1987 | Golden |
| 4,679,571 A | 7/1987 | Frankel et al. |
| 4,690,154 A | 9/1987 | Woodford et al. |
| 4,699,612 A | 10/1987 | Hamacher |
| 4,703,763 A | 11/1987 | McAlister et al. |
| 4,705,497 A | 11/1987 | Shitaokoshi et al. |
| 4,714,461 A | 12/1987 | Gabel |
| 4,715,854 A | 12/1987 | Vaillancourt |
| 4,772,273 A | 9/1988 | Alchas |
| 4,820,287 A | 4/1989 | Leonard |
| 4,838,855 A | 6/1989 | Lynn |
| 4,865,583 A | 9/1989 | Tu |
| 4,879,098 A | 11/1989 | Oberhardt et al. |
| 4,886,072 A | 12/1989 | Percarpio et al. |
| 4,890,627 A | 1/1990 | Haber et al. |
| 4,904,240 A | 2/1990 | Hoover |
| 4,936,315 A | 6/1990 | Lineback |
| 4,980,297 A | 12/1990 | Haynes et al. |
| 4,988,339 A | 1/1991 | Vadher |
| 5,027,827 A | 7/1991 | Cody et al. |
| 5,032,116 A | 7/1991 | Peterson et al. |
| 5,032,288 A | 7/1991 | Columbus et al. |
| 5,035,688 A | 7/1991 | Inui |
| 5,045,185 A | 9/1991 | Ohnaka et al. |
| 5,052,403 A | 10/1991 | Haber et al. |
| 5,054,498 A | 10/1991 | Melet |
| 5,066,284 A | 11/1991 | Mersch et al. |
| 5,084,034 A | 1/1992 | Zanotti |
| 5,086,780 A | 2/1992 | Schmitt |
| 5,097,842 A | 3/1992 | Bonn |
| 5,100,394 A | 3/1992 | Dudar et al. |
| 5,108,927 A | 4/1992 | Dorn |
| 5,116,323 A | 5/1992 | Kreuzer et al. |
| 5,122,129 A | 6/1992 | Olson et al. |
| 5,126,054 A | 6/1992 | Matkovich |
| 5,135,489 A | 8/1992 | Jepson et al. |
| 5,147,329 A | 9/1992 | Brannon |
| 5,208,160 A | 5/1993 | Kikyotani et al. |
| 5,222,502 A | 6/1993 | Kurose |
| 5,269,317 A | 12/1993 | Bennett |
| 5,286,279 A | 2/1994 | Wu |
| 5,330,464 A | 7/1994 | Mathias et al. |
| 5,334,162 A | 8/1994 | Harris |
| 5,354,537 A | 10/1994 | Moreno |
| 5,360,011 A | 11/1994 | McCallister |
| 5,372,143 A | 12/1994 | Bernes et al. |
| 5,395,339 A | 3/1995 | Talonn et al. |
| 5,417,673 A | 5/1995 | Gordon |
| 5,429,610 A | 7/1995 | Vaillancourt |
| 5,431,811 A | 7/1995 | Tusini et al. |
| 5,439,022 A | 8/1995 | Summers et al. |
| 5,439,450 A | 8/1995 | Haedt |
| 5,450,856 A | 9/1995 | Norris |
| 5,451,321 A | 9/1995 | Matkovich |
| 5,454,786 A | 10/1995 | Harris |
| 5,466,228 A | 11/1995 | Evans |
| 5,472,605 A | 12/1995 | Zuk, Jr. |
| 5,485,854 A | 1/1996 | Hollister |
| 5,507,299 A | 4/1996 | Roland |
| 5,520,193 A | 5/1996 | Suzuki et al. |
| 5,522,804 A | 6/1996 | Lynn |
| 5,536,262 A | 7/1996 | Velasquez |
| 5,573,510 A | 11/1996 | Isaacson |
| 5,573,951 A | 11/1996 | Gombrich et al. |
| 5,575,777 A | 11/1996 | Cover et al. |
| 5,577,513 A | 11/1996 | Van Vlasselaer |
| 5,603,700 A | 2/1997 | Daneshvar |
| 5,632,906 A | 5/1997 | Ishida et al. |
| 5,634,893 A | 6/1997 | Rishton |
| 5,649,912 A | 7/1997 | Peterson |
| 5,658,271 A | 8/1997 | Loubser |
| 5,685,846 A | 11/1997 | Michaels, Jr. |
| 5,691,486 A | 11/1997 | Behringer et al. |
| 5,749,857 A | 5/1998 | Cuppy |
| 5,759,160 A | 6/1998 | Neese et al. |
| 5,762,633 A | 6/1998 | Whisson |
| 5,772,608 A | 6/1998 | Dhas |
| 5,785,682 A | 7/1998 | Grabenkort |
| 5,811,658 A | 9/1998 | Van Driel et al. |
| 5,824,001 A | 10/1998 | Erskine |
| 5,833,213 A | 11/1998 | Ryan |
| 5,857,983 A | 1/1999 | Douglas et al. |
| 5,865,803 A | 2/1999 | Major |
| 5,865,812 A | 2/1999 | Correia |
| 5,871,699 A | 2/1999 | Ruggeri |
| 5,873,841 A | 2/1999 | Brannon |
| 5,876,926 A | 3/1999 | Beecham |
| 5,882,318 A | 3/1999 | Boyde |
| 5,911,705 A | 6/1999 | Howell |
| 5,922,551 A | 7/1999 | Durbin et al. |
| RE36,273 E | 8/1999 | Brannon |
| 5,947,932 A | 9/1999 | Desecki et al. |
| 5,961,472 A | 10/1999 | Swendson et al. |
| 5,971,956 A | 10/1999 | Epstein |
| 5,980,830 A | 11/1999 | Savage et al. |
| 6,001,307 A | 12/1999 | Naka et al. |
| 6,010,633 A | 1/2000 | Zuk, Jr. et al. |
| 6,013,037 A * | 1/2000 | Brannon .......... A61B 5/150496 |
| | | 600/576 |
| 6,016,712 A | 1/2000 | Warden et al. |
| 6,050,957 A | 4/2000 | Desch |

(56)                References Cited

U.S. PATENT DOCUMENTS

| | | |
|---|---|---|
| 6,074,366 A | 6/2000 | Rogers et al. |
| 6,103,271 A | 8/2000 | Morrison et al. |
| 6,106,509 A | 8/2000 | Loubser |
| 6,126,643 A | 10/2000 | Vaillancouert |
| 6,146,360 A | 11/2000 | Rogers et al. |
| 6,159,164 A | 12/2000 | Neese et al. |
| 6,171,493 B1 | 1/2001 | Zia et al. |
| 6,190,855 B1 | 2/2001 | Herman et al. |
| 6,210,909 B1 | 4/2001 | Guirguis |
| 6,224,561 B1 | 5/2001 | Swendson et al. |
| 6,254,581 B1 | 7/2001 | Scott |
| 6,296,020 B1 | 10/2001 | McNeely et al. |
| 6,299,131 B1 | 10/2001 | Ryan |
| 6,306,614 B1 | 10/2001 | Romaschin et al. |
| 6,325,975 B1 | 12/2001 | Naka et al. |
| 6,328,726 B1 | 12/2001 | Ishida et al. |
| 6,355,023 B1 | 3/2002 | Roth et al. |
| 6,364,847 B1 | 4/2002 | Shulze et al. |
| 6,364,890 B1 | 4/2002 | Lum et al. |
| 6,368,306 B1 | 4/2002 | Koska |
| 6,387,086 B2 | 5/2002 | Mathias et al. |
| 6,403,381 B1 | 6/2002 | Mann et al. |
| 6,416,496 B1 | 7/2002 | Rogers et al. |
| 6,440,725 B1 | 8/2002 | Pourahmadi et al. |
| 6,478,775 B1 | 11/2002 | Galt et al. |
| 6,482,188 B1 | 11/2002 | Rogers et al. |
| 6,506,182 B2 | 1/2003 | Estabrook et al. |
| 6,511,439 B1 | 1/2003 | Tabata et al. |
| 6,520,948 B1 | 2/2003 | Mathias et al. |
| 6,569,117 B1 | 5/2003 | Ziv et al. |
| 6,592,555 B1 | 7/2003 | Wen-Pi et al. |
| 6,592,613 B1 | 7/2003 | Ishida et al. |
| 6,626,884 B1 | 9/2003 | Dillon et al. |
| 6,629,959 B2 | 10/2003 | Kuracina et al. |
| 6,638,252 B2 | 10/2003 | Moulton et al. |
| 6,638,263 B1 | 10/2003 | Theeuwes et al. |
| 6,648,835 B1 | 11/2003 | Shemesh |
| 6,692,479 B2 | 2/2004 | Kraus et al. |
| 6,695,004 B1 | 2/2004 | Raybuck |
| 6,712,963 B2 | 3/2004 | Schick |
| 6,716,187 B1 | 4/2004 | Jorgensen et al. |
| 6,716,396 B1 | 4/2004 | Anderson et al. |
| 6,733,433 B1 | 5/2004 | Fell |
| 6,736,783 B2 | 5/2004 | Blake et al. |
| 6,746,420 B1 | 6/2004 | Prestidge et al. |
| 6,772,513 B1 | 8/2004 | Frye-Mason et al. |
| 6,843,775 B2 | 1/2005 | Hyun |
| 6,860,871 B2 | 3/2005 | Kuracina et al. |
| 6,905,483 B2 | 6/2005 | Newby et al. |
| 6,913,580 B2 | 7/2005 | Stone |
| 6,945,948 B2 | 9/2005 | Bainbridge et al. |
| 6,979,323 B2 | 12/2005 | Rogers et al. |
| 7,044,941 B2 | 5/2006 | Mathias et al. |
| 7,052,603 B2 | 5/2006 | Schick |
| 7,055,401 B2 | 6/2006 | Prybella et al. |
| 7,087,047 B2 | 8/2006 | Kraus et al. |
| 7,141,097 B2 | 11/2006 | Leahey |
| 7,241,281 B2 | 7/2007 | Coelho et al. |
| 7,261,707 B2 | 8/2007 | Frezza et al. |
| 7,264,608 B2 | 9/2007 | Bischof et al. |
| 7,306,736 B2 | 12/2007 | Collins et al. |
| 7,314,452 B2 | 1/2008 | Madonia |
| 7,316,662 B2 | 1/2008 | Delnevo et al. |
| 7,335,188 B2 | 2/2008 | Graf |
| 7,351,228 B2 | 4/2008 | Keane et al. |
| 7,384,416 B2 | 6/2008 | Goudaliez et al. |
| 7,435,231 B2 | 10/2008 | Mathias et al. |
| 7,461,671 B2 | 12/2008 | Ehwald et al. |
| 7,479,131 B2 | 1/2009 | Mathias et al. |
| 7,544,324 B2 | 6/2009 | Tung et al. |
| 7,614,857 B2 | 11/2009 | Fuechslin et al. |
| 7,615,033 B2 | 11/2009 | Leong |
| 7,618,407 B2 | 11/2009 | Demay et al. |
| 7,648,491 B2 | 1/2010 | Rogers |
| 7,666,166 B1 | 2/2010 | Emmert et al. |
| 7,744,573 B2 | 6/2010 | Gordon et al. |
| 7,766,879 B2 | 8/2010 | Tan et al. |
| 7,896,817 B2 | 3/2011 | Garrison |
| 7,914,508 B2 | 3/2011 | Engstrom |
| 7,923,053 B2 | 4/2011 | Kitching et al. |
| 7,963,950 B2 | 6/2011 | Madonia |
| 8,070,725 B2 | 12/2011 | Christensen |
| 8,109,157 B2 | 2/2012 | Kanayama et al. |
| RE43,283 E | 3/2012 | Ishida et al. |
| 8,197,420 B2 | 6/2012 | Patton |
| 8,206,318 B2 | 6/2012 | Uchiyama et al. |
| 8,206,514 B2 | 6/2012 | Rogers et al. |
| 8,231,546 B2 | 7/2012 | Patton |
| 8,282,605 B2 | 10/2012 | Tan et al. |
| 8,287,499 B2 | 10/2012 | Miyasaka |
| 8,337,418 B2 | 12/2012 | Patton |
| 8,349,254 B2 | 1/2013 | Hoshino et al. |
| 8,356,644 B2 | 1/2013 | Chong et al. |
| 8,377,040 B2 | 2/2013 | Burkholz et al. |
| 8,382,712 B2 | 2/2013 | Kim |
| 8,383,044 B2 | 2/2013 | Davis et al. |
| 8,412,300 B2 | 4/2013 | Sonderegger |
| 8,523,826 B2 | 9/2013 | Layton, Jr. |
| 8,535,241 B2 | 9/2013 | Bullington et al. |
| 8,540,663 B2 | 9/2013 | Davey et al. |
| 8,568,371 B2 | 10/2013 | Siopes et al. |
| 8,574,203 B2 | 11/2013 | Stout et al. |
| 8,603,009 B2 | 12/2013 | Tan et al. |
| 8,647,286 B2 | 2/2014 | Patton |
| 8,679,063 B2 | 3/2014 | Stout et al. |
| 8,747,779 B2 | 6/2014 | Sprague et al. |
| 8,772,046 B2 | 7/2014 | Fraden et al. |
| 8,795,198 B2 | 8/2014 | Tan et al. |
| 8,808,202 B2 | 8/2014 | Brancazio |
| 8,827,958 B2 | 9/2014 | Bierman et al. |
| 8,834,650 B2 | 9/2014 | Rogers et al. |
| 8,864,684 B2 | 10/2014 | Bullington et al. |
| 8,876,734 B2 | 11/2014 | Patton |
| 8,992,505 B2 | 3/2015 | Thorne, Jr. et al. |
| 8,999,073 B2 | 4/2015 | Rogers et al. |
| 9,022,950 B2 | 5/2015 | Bullington et al. |
| 9,022,951 B2 | 5/2015 | Bullington et al. |
| 9,060,724 B2 | 6/2015 | Bullington et al. |
| 9,060,725 B2 | 6/2015 | Bullington et al. |
| 9,138,572 B2 | 9/2015 | Zeytoonian et al. |
| 9,149,576 B2 | 10/2015 | Bullington et al. |
| 9,155,495 B2 | 10/2015 | Bullington et al. |
| 9,204,864 B2 | 12/2015 | Bullington et al. |
| 9,205,198 B2 | 12/2015 | Py |
| 9,233,208 B2 | 1/2016 | Tekeste |
| RE45,896 E | 2/2016 | Stout et al. |
| 9,259,284 B2 | 2/2016 | Rogers et al. |
| 9,314,201 B2 | 4/2016 | Burkholz et al. |
| 9,320,459 B2 | 4/2016 | Chin et al. |
| 9,743,874 B2 | 8/2017 | Kashmirian |
| 9,820,682 B2 | 11/2017 | Rogers et al. |
| 9,855,001 B2 | 1/2018 | Patton |
| 9,855,002 B2 | 1/2018 | Patton |
| 9,855,386 B2 | 1/2018 | Close et al. |
| 9,861,306 B2 | 1/2018 | Patton |
| 9,872,645 B2 | 1/2018 | Patton |
| 9,877,674 B2 | 1/2018 | Holmes et al. |
| 9,877,675 B2 | 1/2018 | Baid |
| 9,895,092 B2 | 2/2018 | Burkholz |
| 9,931,466 B2 | 4/2018 | Bullington et al. |
| 9,950,084 B2 | 4/2018 | Bullington et al. |
| 9,962,489 B2 | 5/2018 | Hopkins |
| 9,999,383 B2 | 6/2018 | Bullington et al. |
| 10,010,282 B2 | 7/2018 | Rogers et al. |
| 10,022,079 B2 | 7/2018 | Hopkins |
| 10,022,530 B2 | 7/2018 | Tekeste |
| 10,028,687 B2 | 7/2018 | Patton |
| 10,028,688 B2 | 7/2018 | Patton |
| 10,028,689 B2 | 7/2018 | Patton |
| 10,039,483 B2 | 8/2018 | Bullington et al. |
| 10,045,724 B2 | 8/2018 | Patton |
| 10,052,053 B2 | 8/2018 | Patton |
| 10,080,516 B2 | 9/2018 | Ellis et al. |
| 10,086,142 B2 | 10/2018 | Tekeste |

(56) References Cited

U.S. PATENT DOCUMENTS

| | | |
|---|---|---|
| 10,123,783 B2 | 11/2018 | Bullington et al. |
| 10,143,412 B2 | 12/2018 | Rogers et al. |
| 10,143,413 B2 | 12/2018 | Garrett et al. |
| 10,206,613 B2 | 2/2019 | Bullington et al. |
| 10,220,139 B2 | 3/2019 | Bullington et al. |
| 10,238,326 B2 | 3/2019 | Gil et al. |
| 10,251,590 B2 | 4/2019 | Bullington et al. |
| 10,265,007 B2 | 4/2019 | Bullington et al. |
| 10,292,633 B2 | 5/2019 | Bullington et al. |
| 10,299,713 B2 | 5/2019 | Patton |
| 10,369,285 B2 | 8/2019 | Hopkins |
| 10,433,779 B2 | 10/2019 | Bullington et al. |
| 10,463,792 B2 | 11/2019 | Hopkins |
| 10,596,315 B2 | 3/2020 | Bullington et al. |
| 10,624,977 B2 | 4/2020 | Bullington et al. |
| 10,736,554 B2 | 8/2020 | Bullington et al. |
| 10,744,315 B2 | 8/2020 | Sanders |
| 10,772,548 B2 | 9/2020 | Bullington et al. |
| 10,827,964 B2 | 11/2020 | Rogers et al. |
| 10,856,791 B2 | 12/2020 | McHale et al. |
| 10,881,343 B2 | 1/2021 | Bullington et al. |
| 10,888,262 B2 | 1/2021 | Russ et al. |
| 10,912,506 B2 | 2/2021 | Bullington et al. |
| 11,076,787 B2 | 8/2021 | Bullington et al. |
| 11,116,904 B2 | 9/2021 | Hopkins |
| 11,167,085 B2 | 11/2021 | Hopkins |
| 11,234,626 B2 | 2/2022 | Bullington et al. |
| 11,253,649 B2 | 2/2022 | Hopkins |
| 11,259,727 B2 | 3/2022 | Bullington et al. |
| 11,311,218 B2 | 4/2022 | Bullington et al. |
| 11,317,838 B2 | 5/2022 | Bullington et al. |
| 11,318,459 B2 | 5/2022 | Shi et al. |
| 11,395,611 B2 | 7/2022 | Bullington et al. |
| 11,395,612 B2 | 7/2022 | Bullington et al. |
| 11,419,531 B2 | 8/2022 | Bullington et al. |
| 11,529,081 B2 | 12/2022 | Bullington et al. |
| 11,589,786 B2 | 2/2023 | Bullington et al. |
| 11,589,843 B2 | 2/2023 | Bullington et al. |
| 11,607,159 B2 | 3/2023 | Bullington et al. |
| 11,653,863 B2 | 5/2023 | Bullington et al. |
| 11,660,030 B2 | 5/2023 | Bullington et al. |
| 11,737,693 B2 | 8/2023 | Bullington et al. |
| 11,786,155 B2 * | 10/2023 | Bullington ......... A61B 5/15003 |
| | | 600/578 |
| 11,819,329 B2 | 11/2023 | Bullington et al. |
| 11,998,332 B2 | 6/2024 | Bullington et al. |
| 12,083,234 B2 | 9/2024 | Bullington et al. |
| 12,133,968 B2 | 11/2024 | Bullington et al. |
| 12,138,052 B1 | 11/2024 | Rogers et al. |
| 12,150,763 B2 | 11/2024 | Bullington et al. |
| 12,186,080 B2 | 1/2025 | Bullington et al. |
| 12,193,816 B2 | 1/2025 | Bullington et al. |
| 2001/0039058 A1 | 11/2001 | Iheme et al. |
| 2002/0002349 A1 | 1/2002 | Flaherty et al. |
| 2002/0004647 A1 | 1/2002 | Leong |
| 2002/0107469 A1 | 8/2002 | Bolan et al. |
| 2002/0183651 A1 | 12/2002 | Hyun |
| 2002/0193751 A1 | 12/2002 | Theeuwes et al. |
| 2003/0013991 A1 | 1/2003 | Stone |
| 2003/0055381 A1 | 3/2003 | Wilkinson |
| 2003/0069543 A1 | 4/2003 | Carpenter et al. |
| 2003/0105414 A1 | 6/2003 | Leong |
| 2003/0121821 A1 | 7/2003 | Roshdy |
| 2003/0208151 A1 | 11/2003 | Kraus et al. |
| 2004/0000309 A1 | 1/2004 | Alston |
| 2004/0009542 A1 | 1/2004 | Dumont et al. |
| 2004/0010228 A1 | 1/2004 | Swenson et al. |
| 2004/0054283 A1 | 3/2004 | Corey et al. |
| 2004/0054333 A1 | 3/2004 | Theeuwes et al. |
| 2004/0073171 A1 | 4/2004 | Rogers et al. |
| 2004/0124389 A1 | 7/2004 | Phillips |
| 2004/0127816 A1 | 7/2004 | Galvao |
| 2004/0147855 A1 | 7/2004 | Marsden |
| 2005/0004524 A1 * | 1/2005 | Newby ............ A61B 5/150648 |
| | | 604/164.08 |
| 2005/0010136 A1 | 1/2005 | Restelli et al. |
| 2005/0054949 A1 | 3/2005 | McKinnon et al. |
| 2005/0082218 A1 | 4/2005 | Verri et al. |
| 2005/0148992 A1 | 7/2005 | Simas et al. |
| 2005/0148993 A1 | 7/2005 | Mathias et al. |
| 2005/0154368 A1 | 7/2005 | Lim et al. |
| 2005/0161112 A1 | 7/2005 | Ehwald et al. |
| 2005/0199077 A1 | 9/2005 | Prybella et al. |
| 2005/0240161 A1 | 10/2005 | Crawford |
| 2005/0245885 A1 | 11/2005 | Brown |
| 2005/0273019 A1 | 12/2005 | Conway et al. |
| 2005/0277848 A1 | 12/2005 | Graf |
| 2005/0281713 A1 | 12/2005 | Hampsch et al. |
| 2006/0009713 A1 | 1/2006 | Flaherty |
| 2006/0018790 A1 | 1/2006 | Naka et al. |
| 2006/0096877 A1 | 5/2006 | Khajavi et al. |
| 2006/0111667 A1 | 5/2006 | Matsuura et al. |
| 2006/0155212 A1 | 7/2006 | Madonia |
| 2006/0251622 A1 | 11/2006 | Suzuki et al. |
| 2006/0287639 A1 | 12/2006 | Sharp |
| 2007/0083162 A1 | 4/2007 | O'Reagan et al. |
| 2007/0088279 A1 | 4/2007 | Shue et al. |
| 2007/0100250 A1 | 5/2007 | Kline |
| 2007/0119508 A1 | 5/2007 | West et al. |
| 2007/0191716 A1 | 8/2007 | Goldberger et al. |
| 2007/0287948 A1 | 12/2007 | Sakiewicz |
| 2008/0086085 A1 | 4/2008 | Brown |
| 2008/0108954 A1 | 5/2008 | Mathias et al. |
| 2008/0114304 A1 * | 5/2008 | Nalesso .............. A61M 39/221 |
| | | 604/207 |
| 2008/0167577 A1 | 7/2008 | Weilbacher et al. |
| 2008/0185056 A1 | 8/2008 | Diodati et al. |
| 2008/0200837 A1 | 8/2008 | Frazier et al. |
| 2008/0254471 A1 | 10/2008 | Bordano |
| 2008/0255523 A1 | 10/2008 | Grinberg |
| 2008/0312576 A1 | 12/2008 | McKinnon et al. |
| 2008/0319346 A1 | 12/2008 | Crawford et al. |
| 2009/0050213 A1 | 2/2009 | Biddell et al. |
| 2009/0076441 A1 | 3/2009 | Sebban |
| 2009/0173685 A1 | 7/2009 | Imai et al. |
| 2009/0177117 A1 | 7/2009 | Amano et al. |
| 2009/0192447 A1 | 7/2009 | Andersen et al. |
| 2009/0227896 A1 | 9/2009 | Alvin Tan et al. |
| 2009/0301317 A1 | 12/2009 | Andrews |
| 2009/0306601 A1 | 12/2009 | Shaw et al. |
| 2010/0010372 A1 | 1/2010 | Brown et al. |
| 2010/0042048 A1 | 2/2010 | Christensen |
| 2010/0057004 A1 | 3/2010 | Christensen et al. |
| 2010/0094171 A1 | 4/2010 | Conway et al. |
| 2010/0152681 A1 | 6/2010 | Mathias |
| 2010/0185134 A1 | 7/2010 | Houwen et al. |
| 2010/0234768 A1 | 9/2010 | Uchiyama et al. |
| 2010/0240964 A1 | 9/2010 | Sterling et al. |
| 2010/0252118 A1 | 10/2010 | Fraden et al. |
| 2010/0255589 A1 | 10/2010 | Saiki et al. |
| 2010/0268118 A1 | 10/2010 | Schweiger |
| 2010/0286513 A1 | 11/2010 | Pollard, Jr. et al. |
| 2010/0298671 A1 | 11/2010 | Asakura et al. |
| 2011/0009717 A1 | 1/2011 | Davis et al. |
| 2011/0046602 A1 | 2/2011 | Grimm et al. |
| 2011/0092856 A1 | 4/2011 | Freeman et al. |
| 2011/0125058 A1 | 5/2011 | Levinson et al. |
| 2011/0198221 A1 | 8/2011 | Angelescu |
| 2011/0288441 A1 | 11/2011 | Taguchi |
| 2011/0306856 A1 | 12/2011 | Rule et al. |
| 2011/0306899 A1 | 12/2011 | Brown et al. |
| 2011/0313318 A1 | 12/2011 | Rule et al. |
| 2012/0004619 A1 | 1/2012 | Stephens et al. |
| 2012/0016266 A1 | 1/2012 | Burkholz |
| 2012/0017999 A1 | 1/2012 | Velschow |
| 2012/0029494 A1 | 2/2012 | Wittenberger et al. |
| 2012/0035540 A1 | 2/2012 | Ferren et al. |
| 2012/0123297 A1 * | 5/2012 | Brancazio .......... A61B 10/0064 |
| | | 600/576 |
| 2012/0226239 A1 * | 9/2012 | Green ................. A61M 5/1782 |
| | | 604/218 |
| 2012/0245042 A1 | 9/2012 | Liu et al. |
| 2012/0265099 A1 | 10/2012 | Goodnow, II et al. |
| 2012/0265128 A1 | 10/2012 | Kolln |

(56) References Cited

U.S. PATENT DOCUMENTS

| | | |
|---|---|---|
| 2012/0277697 A1 | 11/2012 | Haghgooie et al. |
| 2012/0323142 A1 | 12/2012 | Allen et al. |
| 2013/0023792 A1 | 1/2013 | Markey et al. |
| 2013/0085514 A1 | 4/2013 | Lee et al. |
| 2013/0158506 A1 | 6/2013 | Harris et al. |
| 2013/0289420 A1 | 10/2013 | Pfeiffer et al. |
| 2013/0295602 A1 | 11/2013 | Fowler et al. |
| 2014/0008366 A1* | 1/2014 | Genosar ............... A61J 1/2096 |
| | | 220/265 |
| 2014/0051062 A1 | 2/2014 | Vanapalli et al. |
| 2014/0066880 A1 | 3/2014 | Prince et al. |
| 2014/0124542 A1 | 5/2014 | Kojima et al. |
| 2014/0128775 A1* | 5/2014 | Andreae ................ A61B 5/153 |
| | | 600/581 |
| 2014/0155782 A1* | 6/2014 | Bullington ....... A61B 5/150221 |
| | | 600/575 |
| 2014/0188002 A1 | 7/2014 | Close et al. |
| 2014/0208978 A1 | 7/2014 | Sunder et al. |
| 2014/0221873 A1 | 8/2014 | Hayakawa et al. |
| 2014/0257249 A1* | 9/2014 | Witt ...................... A61M 39/10 |
| | | 604/535 |
| 2014/0276039 A1 | 9/2014 | Cowan et al. |
| 2014/0305196 A1 | 10/2014 | Ellis et al. |
| 2014/0336536 A1 | 11/2014 | Brancazio |
| 2015/0011847 A1 | 1/2015 | Hayden |
| 2015/0018715 A1 | 1/2015 | Walterspiel |
| 2015/0025454 A1 | 1/2015 | Wetzel et al. |
| 2015/0025455 A1 | 1/2015 | Shetty et al. |
| 2015/0025456 A1 | 1/2015 | Shetty et al. |
| 2015/0073304 A1 | 3/2015 | Millerd |
| 2015/0151298 A1 | 6/2015 | Hobbs et al. |
| 2015/0314105 A1 | 11/2015 | Gasparyan et al. |
| 2015/0359473 A1 | 12/2015 | Garrett et al. |
| 2016/0008579 A1 | 1/2016 | Burkholz et al. |
| 2016/0038068 A1 | 2/2016 | Chickering, III et al. |
| 2016/0038684 A1 | 2/2016 | Lum et al. |
| 2016/0081606 A1 | 3/2016 | Russ et al. |
| 2016/0089070 A1 | 3/2016 | Russ et al. |
| 2016/0113560 A1 | 4/2016 | Bullington et al. |
| 2016/0174888 A1 | 6/2016 | Berthier et al. |
| 2016/0174948 A1 | 6/2016 | Kato et al. |
| 2016/0213294 A1 | 7/2016 | Patton |
| 2016/0257586 A1 | 9/2016 | Shaamsundarr |
| 2016/0361006 A1 | 12/2016 | Bullington et al. |
| 2016/0367177 A1 | 12/2016 | Edelhauser et al. |
| 2017/0020427 A1 | 1/2017 | Rogers et al. |
| 2017/0020428 A1* | 1/2017 | Rogers ............. A61B 5/150213 |
| 2017/0059552 A1 | 3/2017 | Campton et al. |
| 2017/0071519 A1 | 3/2017 | Gelfand et al. |
| 2017/0153165 A1 | 6/2017 | Nwadigo |
| 2017/0276679 A1 | 9/2017 | Chapman et al. |
| 2017/0327867 A1 | 11/2017 | Dohale et al. |
| 2017/0361019 A1 | 12/2017 | Hopkins |
| 2018/0093077 A1 | 4/2018 | Harding et al. |
| 2018/0140240 A1 | 5/2018 | Bullington et al. |
| 2018/0160958 A1 | 6/2018 | Baid |
| 2018/0177445 A1 | 6/2018 | Rogers et al. |
| 2018/0220944 A1 | 8/2018 | Otsubo et al. |
| 2018/0242890 A1 | 8/2018 | Chickering, III et al. |
| 2018/0271425 A1 | 9/2018 | Rogers et al. |
| 2018/0289894 A1 | 10/2018 | Hopkins |
| 2018/0321270 A1* | 11/2018 | Iwashita ................ G01N 37/00 |
| 2018/0353117 A1 | 12/2018 | Bullington et al. |
| 2019/0000367 A1 | 1/2019 | Lundquist et al. |
| 2019/0030293 A1 | 1/2019 | Rogers et al. |
| 2019/0076074 A1 | 3/2019 | Bullington et al. |
| 2019/0150818 A1 | 5/2019 | Bullington et al. |
| 2019/0159711 A1 | 5/2019 | Rogers et al. |
| 2019/0209066 A1* | 7/2019 | Bullington ....... A61B 5/150351 |
| 2019/0365303 A1 | 12/2019 | Bullington et al. |
| 2019/0374145 A1 | 12/2019 | Breindel et al. |
| 2020/0060595 A1 | 2/2020 | Bullington et al. |
| 2020/0060596 A1 | 2/2020 | Patton |
| 2020/0197925 A1 | 6/2020 | Ivosevic et al. |
| 2020/0214611 A1 | 7/2020 | Ivosevic |
| 2020/0215211 A1 | 7/2020 | Bullington et al. |
| 2020/0253524 A1 | 8/2020 | Bullington et al. |
| 2020/0281514 A1 | 9/2020 | Rogers et al. |
| 2020/0289039 A1 | 9/2020 | Bullington et al. |
| 2020/0305780 A1 | 10/2020 | Rogers et al. |
| 2020/0352497 A1 | 11/2020 | Brewer et al. |
| 2021/0008280 A1 | 1/2021 | Bullington et al. |
| 2021/0085230 A1 | 3/2021 | Brewer et al. |
| 2021/0169387 A1 | 6/2021 | Bullington et al. |
| 2021/0186392 A1 | 6/2021 | Bullington et al. |
| 2021/0186394 A1 | 6/2021 | Ma et al. |
| 2021/0275068 A1 | 9/2021 | Miazga et al. |
| 2021/0290123 A1 | 9/2021 | Sawyer |
| 2021/0345919 A1 | 11/2021 | Brewer et al. |
| 2021/0345920 A1 | 11/2021 | Brewer et al. |
| 2021/0345921 A1 | 11/2021 | Brewer et al. |
| 2021/0345922 A1 | 11/2021 | Brewer et al. |
| 2021/0361206 A1 | 11/2021 | Bullington et al. |
| 2021/0361207 A1* | 11/2021 | Rogers ............. A61B 5/150274 |
| 2022/0023539 A1 | 1/2022 | Hopkins |
| 2022/0151525 A1 | 5/2022 | Bullington et al. |
| 2022/0151526 A1 | 5/2022 | Bullington et al. |
| 2022/0151527 A1 | 5/2022 | Bullington et al. |
| 2022/0175284 A1 | 6/2022 | Bullington et al. |
| 2022/0183600 A1 | 6/2022 | Bullington et al. |
| 2022/0218248 A1 | 7/2022 | Bullington et al. |
| 2022/0218249 A1 | 7/2022 | Bullington et al. |
| 2022/0218250 A1 | 7/2022 | Bullington et al. |
| 2022/0287604 A1 | 9/2022 | Armstrong et al. |
| 2022/0304600 A1 | 9/2022 | Hammer |
| 2022/0304601 A1 | 9/2022 | Bullington et al. |
| 2022/0304664 A1 | 9/2022 | Hammer |
| 2022/0361786 A1 | 11/2022 | Bullington et al. |
| 2022/0369970 A1 | 11/2022 | Bullington et al. |
| 2022/0369971 A1 | 11/2022 | Bullington et al. |
| 2022/0369972 A1 | 11/2022 | Bullington et al. |
| 2023/0109255 A1 | 4/2023 | Rogers et al. |
| 2023/0172502 A1 | 6/2023 | Bullington et al. |
| 2023/0190157 A1 | 6/2023 | Bullington et al. |
| 2023/0240571 A1 | 8/2023 | Bullington et al. |
| 2023/0248281 A1 | 8/2023 | Bullington et al. |
| 2023/0320702 A1 | 10/2023 | Bullington et al. |
| 2023/0363674 A1 | 11/2023 | Bullington et al. |
| 2024/0008780 A1 | 1/2024 | Bullington et al. |
| 2024/0041370 A1 | 2/2024 | Bullington et al. |
| 2024/0065590 A1 | 2/2024 | Bullington et al. |
| 2024/0131258 A1 | 4/2024 | Bullington et al. |
| 2024/0138734 A1 | 5/2024 | Bullington et al. |
| 2024/0164670 A1 | 5/2024 | Patton |
| 2024/0306963 A1 | 9/2024 | Bullington et al. |
| 2024/0306964 A1 | 9/2024 | Bullington et al. |
| 2024/0315620 A1 | 9/2024 | Bullington et al. |
| 2024/0315621 A1 | 9/2024 | Bullington et al. |
| 2024/0315622 A1 | 9/2024 | Bullington et al. |
| 2024/0315623 A1 | 9/2024 | Bullington et al. |
| 2024/0315624 A1 | 9/2024 | Bullington et al. |
| 2025/0082235 A1 | 3/2025 | Bullington et al. |
| 2025/0120628 A1 | 4/2025 | Bullington et al. |
| 2025/0235133 A1 | 7/2025 | Bullington et al. |
| 2025/0235613 A1 | 7/2025 | Bullington |
| 2025/0275697 A1 | 9/2025 | Bullington et al. |

FOREIGN PATENT DOCUMENTS

| | | | |
|---|---|---|---|
| BR | 112012025546 A2 | 6/2016 | |
| CA | 1264275 A | 1/1990 | |
| CN | 86103696 A | 1/1987 | |
| CN | 2115767 U | 9/1992 | |
| CN | 1713928 A | 12/2005 | |
| CN | 1784186 A | 6/2006 | |
| CN | 1901955 A | 1/2007 | |
| CN | 2907683 Y | 6/2007 | |
| CN | 101060871 A | 10/2007 | |
| CN | 101309641 A | 11/2008 | |
| CN | 101352357 A | 1/2009 | |
| CN | 101437450 A | 5/2009 | |
| CN | 101564301 A | 10/2009 | |
| CN | 101631498 A | 1/2010 | |
| CN | 101676001 A | 3/2010 | |

(56)        References Cited

FOREIGN PATENT DOCUMENTS

| | | | |
|---|---|---|---|
| CN | 101785676 A | 7/2010 |
| CN | 101801445 A | 8/2010 |
| CN | 201617841 U | 11/2010 |
| CN | 102421362 A | 4/2012 |
| CN | 102548524 A | 7/2012 |
| CN | 102811754 A | 12/2012 |
| CN | 102971040 A | 3/2013 |
| CN | 103027727 A | 4/2013 |
| CN | 101626803 B | 8/2013 |
| CN | 103477201 A | 12/2013 |
| CN | 103619386 A | 3/2014 |
| CN | 104955392 A | 9/2015 |
| CN | 104971390 A | 10/2015 |
| CN | 105090005 A | 11/2015 |
| CN | 105612346 A | 5/2016 |
| CN | 105813669 A | 7/2016 |
| CN | 105832453 A | 8/2016 |
| CN | 107874786 A | 4/2018 |
| DE | 7203008 U | 5/1972 |
| DE | 2203858 A1 | 5/1973 |
| DE | 2541494 A1 | 3/1977 |
| DE | 2203858 B2 | 10/1977 |
| DE | 2946660 A1 | 5/1981 |
| DE | 3403957 A1 | 8/1985 |
| DE | 4026732 A1 | 2/1992 |
| DE | 29913417 U1 | 12/2000 |
| DE | 10038026 A1 | 2/2001 |
| DE | 10134913 A1 | 2/2003 |
| DE | 10134913 C2 | 6/2003 |
| DE | 10243129 A1 | 4/2004 |
| DE | 102009057792 B4 | 8/2016 |
| EP | 0181957 * | 11/1984 | ................ B01L 3/02 |
| EP | 0207304 A1 | 1/1987 |
| EP | 0264191 A2 | 4/1988 |
| EP | 0448795 A2 | 10/1991 |
| EP | 0208053 B1 | 12/1991 |
| EP | 0329786 B1 | 1/1993 |
| EP | 0565103 A1 | 10/1993 |
| EP | 0486059 B1 | 1/1997 |
| EP | 1219283 A2 | 7/2002 |
| EP | 1144026 B1 | 7/2004 |
| EP | 1219283 B1 | 6/2005 |
| EP | 1980204 A1 | 10/2008 |
| EP | 2254472 A2 | 12/2010 |
| EP | 1381438 B1 | 5/2012 |
| EP | 2692324 A1 | 2/2014 |
| EP | 2986216 A1 | 2/2016 |
| EP | 2254472 B1 | 5/2016 |
| EP | 1487369 B1 | 5/2017 |
| EP | 2986218 B1 | 12/2017 |
| EP | 2178585 B1 | 4/2021 |
| FR | 2110516 A5 | 6/1972 |
| FR | 2691364 B1 | 8/1999 |
| FR | 2833175 B1 | 5/2004 |
| FR | 2851167 B1 | 10/2005 |
| GB | 1506449 A | 4/1978 |
| GB | 1562686 A | 3/1980 |
| IE | 904353 A1 | 10/1991 |
| IL | 128709 A | 9/2004 |
| JP | S5397289 A | 8/1978 |
| JP | S5789869 A | 6/1982 |
| JP | S6458241 A | 3/1989 |
| JP | H0363570 A | 3/1991 |
| JP | H0614973 A | 1/1994 |
| JP | H06500403 A | 1/1994 |
| JP | H0716219 A | 1/1995 |
| JP | H0910302 A | 1/1997 |
| JP | H10211274 A | 8/1998 |
| JP | H1156821 A | 3/1999 |
| JP | H1176397 A | 3/1999 |
| JP | 2001159630 A | 6/2001 |
| JP | 2001276181 A | 10/2001 |
| JP | 3231086 B2 | 11/2001 |
| JP | 2002116201 A | 4/2002 |
| JP | 3498201 B2 | 2/2004 |
| JP | 2005237617 A | 9/2005 |
| JP | 2006026327 A | 2/2006 |
| JP | 3813974 B2 | 8/2006 |
| JP | 2007175534 A | 7/2007 |
| JP | 2008149076 A | 7/2008 |
| JP | 2008206734 A | 9/2008 |
| JP | 4382322 B2 | 12/2009 |
| JP | 2010514501 A | 5/2010 |
| JP | 4573538 B2 | 11/2010 |
| JP | 4861649 B2 | 1/2012 |
| JP | 4869910 B2 | 2/2012 |
| JP | 5344252 B2 | 11/2013 |
| JP | 5620541 B2 | 11/2014 |
| JP | 2015014552 A | 1/2015 |
| JP | 2016500278 A | 1/2016 |
| JP | 2016523591 A | 8/2016 |
| JP | 5997760 B2 | 9/2016 |
| JP | 2016527939 A | 9/2016 |
| JP | 6194415 B2 | 9/2017 |
| JP | 2018525191 A | 9/2018 |
| KR | 20120030087 A | 3/2012 |
| KR | 101134279 B1 | 4/2012 |
| KR | 20160088853 A | 7/2016 |
| TW | 200528066 A | 9/2005 |
| WO | WO-8605568 A1 | 9/1986 |
| WO | WO-9004351 A1 | 5/1990 |
| WO | WO-8403213 A1 | 10/1990 |
| WO | WO-9118632 A1 | 12/1991 |
| WO | WO-9216144 A1 | 10/1992 |
| WO | WO-9407415 A1 | 4/1994 |
| WO | WO-1994012093 A1 | 6/1994 |
| WO | WO-9415665 A1 | 7/1994 |
| WO | WO-9511712 A1 | 5/1995 |
| WO | WO-9516395 A1 | 6/1995 |
| WO | WO-1995021639 A1 | 8/1995 |
| WO | WO-9524176 A1 | 9/1995 |
| WO | WO-9621853 A1 | 7/1996 |
| WO | WO-9718845 A1 | 5/1997 |
| WO | WO-1997045714 A1 | 12/1997 |
| WO | WO-1998034532 A1 | 8/1998 |
| WO | WO-9846136 A1 | 10/1998 |
| WO | WO-9913925 A1 | 3/1999 |
| WO | WO-9948425 A1 | 9/1999 |
| WO | WO-9955232 A1 | 11/1999 |
| WO | WO-2000024313 A1 | 5/2000 |
| WO | WO-0041624 A1 | 7/2000 |
| WO | WO-0108546 A2 | 2/2001 |
| WO | WO-0191829 A2 | 12/2001 |
| WO | WO-0245813 A1 | 6/2002 |
| WO | WO-02051520 A1 | 7/2002 |
| WO | WO-03008012 A2 | 1/2003 |
| WO | WO-03041767 A1 | 5/2003 |
| WO | WO-03047660 A1 | 6/2003 |
| WO | WO-03078964 A2 | 9/2003 |
| WO | WO-03085395 A1 | 10/2003 |
| WO | WO-2003092573 A2 | 11/2003 |
| WO | WO-2004082467 A2 | 9/2004 |
| WO | WO-2004103565 A2 | 12/2004 |
| WO | WO-2005068011 A1 | 7/2005 |
| WO | WO-2006031500 A2 | 3/2006 |
| WO | WO-2006124634 A1 | 11/2006 |
| WO | WO-2007033319 A1 | 3/2007 |
| WO | WO-2008028165 A2 | 3/2008 |
| WO | WO-2008077047 A2 | 6/2008 |
| WO | WO-2008101025 A1 | 8/2008 |
| WO | WO-2009094345 A1 | 7/2009 |
| WO | WO-2009113999 A2 | 9/2009 |
| WO | WO-2009133755 A1 | 11/2009 |
| WO | WO-2010087216 A1 | 8/2010 |
| WO | WO-2011030282 A1 | 3/2011 |
| WO | WO-2011069145 A2 | 6/2011 |
| WO | WO-2011114413 A1 | 9/2011 |
| WO | WO-2011123685 A2 | 10/2011 |
| WO | WO-2011162772 A1 | 12/2011 |
| WO | WO-2012012127 A2 | 1/2012 |
| WO | WO-2012114105 A1 | 8/2012 |
| WO | WO-2013115729 A1 | 8/2013 |
| WO | WO-2013181352 A1 | 12/2013 |
| WO | WO-2014022275 A1 | 2/2014 |

(56) References Cited

FOREIGN PATENT DOCUMENTS

| WO | WO-2014022750 A1 | 2/2014 |
| WO | WO-2014058945 A1 | 4/2014 |
| WO | WO-2014085800 A1 | 6/2014 |
| WO | WO-2014089186 A1 | 6/2014 |
| WO | WO-2014099266 A2 | 6/2014 |
| WO | WO-2015091818 A1 | 6/2015 |
| WO | WO-2015134431 A1 | 9/2015 |
| WO | WO-2016027782 A1 | 2/2016 |
| WO | WO-2016054252 A1 | 4/2016 |
| WO | WO-2016201406 A1 | 12/2016 |
| WO | WO-2017019552 A1 | 2/2017 |
| WO | WO-2017041087 A1 | 3/2017 |
| WO | WO-2017133953 A1 | 8/2017 |
| WO | WO-2018125929 A1 | 7/2018 |
| WO | WO-2018227191 A1 | 12/2018 |
| WO | WO-2019055487 A1 | 3/2019 |
| WO | WO-2019113505 A1 | 6/2019 |
| WO | WO-2019232196 A1 | 12/2019 |
| WO | WO-2020163744 A1 | 8/2020 |
| WO | WO-2020185914 A1 | 9/2020 |
| WO | WO-2020227701 A1 | 11/2020 |
| WO | WO-2021178910 A1 | 9/2021 |
| WO | WO-2022203747 A1 | 9/2022 |

OTHER PUBLICATIONS

Barnard, D. R. & Arthur, M. M., "Fibronectin (cold insoluble globulin) in the neonate," Clinical and Laboratory Observations, 102(3):453-455 (1983).

Baxter, "IV Tubing and Access Devices" authored by and published by Baxter, dated Nov. 6, 2006, 105 pages.

BD Saf-T-Intima Closed IV Catheter System, Becton, Dickinson and Company, 2015 Brochure. Retrieved from the Internet (Sep. 11, 2019) https://www.bd.com/en-us/offerings/capabilities/infusion- therapy/iv-catheters/bd-saf-tintima-closed-iv-catheter-system, 2 pages.

BD Vacutainer Passive Shielding Blood Collection Needle Brochure; Becton Dickinson and Company (2005), 2 pages.

Brecher, M. E. et al., "Bacterial Contamination of Blood Components," Clinical Microbiology Reviews, 18(1):195-204 (2005).

Calam, R. R., "Recommended 'Order of Draw' for Collecting Blood Specimens Into Additive-Containing Tubes," Letter to the Editor, Clinical Chemistry, 28(6):1399 (1982), 1 page.

Cartridge and Test Information, Abbott, Art: 714258-010 Rev. Date: Aug. 15, 2016, 6 pages.

Challiner, A. et al., Queen Alexandra Hospital, Portsmouth P06 3LY, "Venous/arterial blood management protection system," Anaesthesia, Correspondence (Feb. 1992); 47(2), p. 169.

De Korte, D. et al., "Diversion of first blood volume results in a reduction of bacterial contamination for whole-blood collections," Vox Sanguinis, 83:13-16 (2002).

De Korte, D. et al., "Effects of skin disinfection method, deviation bag, and bacterial screening on clinical safety of platelet transfusions in the Netherlands," Transfusion, 46:476-485 (2006).

Edwards Lifesciences, "Conservation. Safety. Simplicity. Edwards VAMP and VAMP Jr. Systems," 2002 Brochure. Retrieved from the Internet (Sep. 11, 2019) https://www.medline.com/media/catalog/Docs/MKT/VAMPSYSTEMBROCHURE.PDF, 4 pages.

Ernst, D. J. et al., "NCCLS simplifies the order of draw: a brief history," MLO, pp. 26-27 (2004).

Gottlieb, T., "Hazards of Bacterial Contamination of Blood Products," Anaesth Intens Care, 21:20-23 (1993).

Hall, K. K. et al., "Updated Review of Blood Culture Contamination," Clinical Microbiology Reviews, 19(4):788-802 (2006).

Hillyer, C. D. et al., "Bacterial Contamination of Blood Components Risks, Strategies, and Regulation," Hematology, 575-589 (2003).

International Preliminary Search Report for International Application No. PCT/US2020/017261, dated Aug. 10, 2021, 8 pages.

International Search Report and Written Opinion for International Application No. PCT/US2020/017261, mailed May 14, 2020.

Kim, J. Y. et al., "The Sum of the Parts is Greater Than the Whole: Reducing Blood Culture Contamination," Annals of Internal Medicine, 154:202-203 (2011).

Levin, P. D. et al., "Use of the Nonwire Central Line Hub to Reduce Blood Culture Contamination," Chest, 143(3):640-645 (2013).

Liumbruno, G. M. et al., "Reduction of the risk of bacterial contamination of blood components through diversion of the first part of the donation of blood and blood components," Blood Transfus, 7:86-93 (2009).

Li, Y. et al., "Direct labeling and visualization of blood vessels with lipophilic carbocyanine dye Oil," Nature Protocols, 3(11):1703-1708 (2008).

Mayer, G. A, "A Method for the Reliable Determination of Clotting Time in Whole Blood," Can Med Assoc J., 72(12):927-929 (1955).

McDonald, C. P., "Interventions Implemented to Reduce the Risk of Transmission of Bacteria by Transfusion in the English National Blood Service," Transfus Med Hemother, 38:255-258 (2011).

Meissner, G. F. et al., "A Method Based on the Use of Whole Venous Blood in Capillary Tubes," American Journal of Clinical Pathology, 33(2):29-31 (1963).

Murphy, M., "Better Blood Transfusion," Journal of the Intensive Core Society, 4(3):78-80 (2003).

Napolitano, M. et al., "Quality control of bacterial contamination of blood components: the feasibility of diversion system testing," Blood Transfus, 2:231-232 (2004).

Non-Final Office Action for U.S. Appl. No. 16/785,170 mailed on Sep. 14, 2022, 10 pages.

Norberg, A et al., "Contamination Rates of Blood Cultures Obtained by Dedicated Phlebotomy vs Intravenous Catheter," JAMA, 289(6):726-729 (2003).

Order of Draw for Multiple Tube Collections, LabNotes, a newsletter from BD Diagnostics,—Preanalytical Systems, 17(1):3 (2007), 1 page.

Page, C. et al., "Blood conservation devices in critical care: a narrative review," Annals of Intensive Care, 3:14 (2013), 6 pages.

Palavecino, E. L. et al., "Detecting Bacterial Contamination in Platelet Products," Clin. Lab., 52:443-456 (2006).

Pall Corp., "Leukotrap Filtration Systems for Whole Blood Derived Platelets: Leukotrap RC PL and Leukotrap PL Systems," 2005 Brochure, 2 pages.

Patton, R. G. et al., "Innovation for Reducing Blood Culture Contamination: Initial Specimen Diversion Technique," Journal of Clinical Microbiology, 48(12):4501-4503 (2010).

Perez, P. et al., "Multivariate analysis of determinants of bacterial contamination of whole-blood donations," Vox Sanguinis, 82:55-60 (2002).

Proehl, J. A et al., "Clinical Practice Guideline: Prevention of Blood Culture Contamination, Full Version," 2012 ENA Emergency Nurses Resources Development Committee, Emergency Nurses Association (Dec. 2012), 14 pages.

Quilici, N. et al., "Differential Quantitative Blood Cultures in the Diagnosis of Catheter-Related Sepsis in Intensive Care Units," Clinical Infectious Diseases 25:1066-1070 (1997).

Schuur, J., "Blood Cultures: When Do they Help and When Do They Harm?" Brigham & Women's Hospital, Department of Emergency Medicine, (Jun. 21-23, 2012), 42 pages.

Sheppard, C. A et al., "Bacterial Contamination of Platelets for Transfusion: Recent Advances and Issues," LabMedicine, 36(12):767-770 (2005).

Shulman, G., "Quality of Processed Blood for Autotransfusion," The Journal of Extra-Corporeal Technology, 32(1):11-19 (2000).

Sibley, C. D. et al., "Molecular Methods for Pathogen and Microbial Community Detection and Characterization: Current and Potential Application in Diagnostic Microbiology," Infection, Genetics and Evolution 12:505-521 (2012).

Stohl, S. et al., "Blood Cultures at Central Line Insertion in the Intensive Care Unit: Comparison with Peripheral Venipuncture," Journal of Clinical Microbiology, 49(7):2398-2403 (2011).

Tang, M. et al., "Closed Blood Conservation Device for Reducing Catheter-Related Infections in Children After Cardiac Surgery," Critical Care Nurse, 34(5):53-61 (2014).

(56)         References Cited

OTHER PUBLICATIONS

Wagner et al., "Diversion of Initial Blood Flow to Prevent Whole-Blood Contamination by Skin Surface Bacteria: an in vitro model," Transfusion, 40:335-338 (2000).

Wang, P. et al., "Strategies on Reducing Blood Culture Contamination," Reviews in Medical Microbiology, 23: pp. 63-66 (2012).

Weinbaum, F. I. et al., "Doing It Right the First Time: Quality Improvement and the Contaminant Blood Culture," Journal of Clinical Microbiology, 35(3):563-565 (1997).

Weinstein, M.P., "Current Blood Culture Methods and Systems: Clinical Concepts, Technology, and Interpretation of Results," Clinical Infectious Diseases, 23:40-46 (1996).

Weinstein, M.P. et al., "The Clinical Significance of Positive Blood Cultures in the 1990s: A Prospective Comprehensive Evaluation of the Microbiology, Epidemiology, and Outcome of Bacteremia and Fungemia in Adults," Clinical Infectious Diseases, 24:584-602 (1997).

Weinstein, M.P., "MiniReview: Blood Culture Contamination: Persisting Problems and Partial Progress," Journal of Clinical Microbiology, 41(6):2275-2278 (2003).

Ziegler, et al., "Controlled Clinical Laboratory Comparison of Two Supplemented Aerobic and Anaerobic Media Used in Automated Blood Culture Systems to Detect Bloodstream Infections," J. Clinical Microbiology, 36(3):657-661 (1998).

Zimmon, D. S. et al., "Effect of Portal Venous Blood Flow Diversion on Portal Pressure," J Clin Invest, 65(6):1388-1397 (1980).

Zundert, A V., "New Closed IV Catheter System," Acta Anaesth. Belg., 56:283-285 (2005).

Avatar: "Is it safe to reinfuse blood drawn from a CVAD via a syringe when checking line patency or drawing blood?" [retrieved online Jul. 31, 2024] URL:https://www.avatargroup.org.au/faq---blood-collection.html, 4 pages.

Bruneau, Cecile, et al.; "Efficacy of a new collection procedure for preventing bacterial contamination of whole-blood donations," Transfusion (2001); 41(1):74-81.

Extended European Search Report for European Application No. 23029844.2, mailed Mar. 20, 2024, 9 pages.

Extended European Search Report for European Application No. 23217471.4, mailed May 22, 2024, 8 pages.

Extended European Search Report for European Application No. 23218666.8 mailed Apr. 18, 2024, 9 pages.

McDonald, C.P.; "Bacterial risk reduction by improved donor arm disinfection, diversion and bacterial screening," Transfus Med., (2006); 16(6):381-396.

Office Action for Australian Application No. 2020218544, mailed Jul. 31, 2024, 3 pages.

Office Action for Canadian Application No. 3066670, mailed Oct. 4, 2024, 4 pages.

Office Action for Canadian Application No. 3183294, mailed Aug. 19, 2024, 5 pages.

Office Action for Chinese Application No. 202080025953.7, mailed Aug. 28, 2024, with English language translation, 26 pages.

Office Action for Chinese Application No. 202080025953.7, mailed Jan. 9, 2024, with English translation, 27 pages.

Office Action for Israeli Application No. 285289, mailed May 6, 2024, 4 pages.

Office Action for Israeli Application No. 286263, mailed May 12, 2024, 4 pages.

Office Action for Israeli Application No. 309638, mailed Jul. 16, 2024, 3 pages.

Office Action for Japanese Application No. 2021-546225, mailed Dec. 19, 2023, with English translation, 11 pages.

Office Action for Japanese Application No. 2022-184274, mailed Jun. 14, 2024, with English Translation, 4 pages.

Office Action for Japanese Application No. 2022-212405, mailed Jun. 20, 2024, with English translation, 6 pages.

Office Action for Japanese Application No. 2023-075104 mailed Feb. 29, 2024, with English Translation, 9 pages.

Office Action for U.S. Appl. No. 17/136,882, mailed Apr. 19, 2024, 8 pages.

Office Action for U.S. Appl. No. 17/193,930, mailed Jun. 7, 2024, 10 pages.

Office Action for U.S. Appl. No. 17/403,500, mailed May 20, 2024, 28 pages.

Office Action for U.S. Appl. No. 18/227,185, mailed Apr. 18, 2024, 18 pages.

Office Action for U.S. Appl. No. 18/227,185, mailed Oct. 31, 2024, 17 pages.

Office Action for U.S. Appl. No. 18/380,259, mailed Oct. 16, 2024, 15 pages.

Office Action for U.S. Appl. No. 18/399,007, mailed Mar. 7, 2024, 8 pages.

Office Action for U.S. Appl. No. 18/407,010, mailed Mar. 13, 2024, 8 pages.

Office Action for U.S. Appl. No. 18/407,010, mailed Sep. 6, 2024, 11 pages.

Office Action for U.S. Appl. No. 18/675,824, mailed Jul. 26, 2024, 13 pages.

Office Action for U.S. Appl. No. 18/676,186, mailed Aug. 5, 2024, 13 pages.

Patel, R. et al., "Optimized Pathogen Detection with 30- Compared to 20-Milliliter Blood Culture Draws." Journal of Clinical Microbiology, 49(12):4047-4051 (2011).

Arenas et al., "Asynchronous Testing of 2 Specimen-Diversion Devices to reduce Blood Culture Contamination: A Single-Site Product Supply Quality Improvement Project," J. Emergency Nursing, vol. 47, No. 2, pp. 256-264.e6 (Mar. 2021), 15 pages.

Bauman et al., "Don't Stick Me Again! Reducing Blood Culture Contamination," INOVA Fairfax Medical Campus, Emergency Department (2019), 1 page.

Bell et al., Effectiveness of a Novel Specimen Collection System in Reducing Blood Culture Contamination Rates, J. Emergency Nursing, vol. 44, No. 6, 570 (Nov. 2018), 6 pages.

Blakeney, "Reduction of Blood Culture Contaminations Using Initial Specimen Diversion Device," Beebe Healthcare (Jun. 2018), 1 page.

Brownfield et al., "Emergency Department Observes 83% Reduction in Blood Culture Contamination with Initial Specimen Diversion Technology Adoption," Am. J. Infection Control, vol. 49, S14, ADS 34 (Jun. 2021), 1 page.

Chamarthy, P., et al.; "Mixing Characteristics in a Serpentine Micro-Channel," IMECE2004-61902; Proceedings of the ASME 2004 International Mechanical Engineering Congress and Exposition. Fluids Engineering. Anaheim, California, USA; Nov. 13-19, 2004, pp. 253-261; Exhibit 4; 10 pages.

Chang et al., "Impact of Blood Culture Diversion Device and Molecular Pathogen Identification on Vancomycin Use," San Antonio Military Medical Center (2016), 1 page.

Doern et al., "A Comprehensive Update on the Problem of Blood Culture Contamination and a Discussion of Methods for Addressing the Problem," Clinical Microbiology, vol. 33, No. 1, e00009-19 (Jan. 2020), 21 pages.

Extended European Search Report for European Application No. 16808502.5, mailed Jan. 23, 2019, 5 pages.

Extended European Search Report for European Application No. 17204012.3, mailed Feb. 14, 2018, 7 pages.

Extended European Search Report for European Application No. 18188136.8, mailed May 16, 2019, 9 pages.

Extended European Search Report for European Application No. 18855938.9, mailed Aug. 2, 2021, 7 pages.

Extended European Search Report for European Application No. 18885543.1, mailed Oct. 8, 2021, 8 pages.

Extended European Search Report for European Application No. 19156636.3, mailed Aug. 27, 2019, 7 pages.

Extended European Search Report for European Application No. 19190772.4, mailed Feb. 10, 2020, 7 pages.

Extended European Search Report for European Application No. 20176877.7, mailed Dec. 1, 2020, 9 pages.

Extended European Search Report for European Application No. 20207898.6, mailed Aug. 30, 2021, 8 pages.

Extended European Search Report for European Application No. 21167069.0, mailed Nov. 10, 2021, 9 pages.

(56) References Cited

OTHER PUBLICATIONS

Extended European Search Report for European Application No. 21167625.9, mailed Oct. 8, 2021, 7 pages.
Extended European Search Report for European Application No. 21197514.9, mailed Mar. 30, 2022, 9 pages.
Extended European Search Report for European Application No. 22158983.1, mailed Aug. 1, 2022, 9 pages.
Extended European Search Report for European Application No. 22172183.0, mailed Sep. 11, 2022, 7 pages.
Extended European Search Report for European Application No. 22194769.0, mailed Feb. 28, 2023, 9 pages.
Extended European Search Report for European Application No. 22210589.2, mailed Apr. 17, 2023, 6 pages.
Extended European Search Report for European Application No. 23153164.1, mailed Aug. 7, 2023, 8 pages.
Extended European Search Report for European Application No. 23171135.9, mailed Oct. 30, 2023, 8 pages.
Extended European Search Report for European Application No. 23182529.0, mailed Dec. 19, 2023, 13 pages.
Extended European Search Report for European Application No. 24217446.4, mailed Apr. 17, 2025, 8 pages.
Garstecki, P., et al.; "Formation of droplets and bubbles in a microfluidic T-junction-scaling and mechanism of break-up," Lab Chip; 6(3):437-446 (Mar. 2006).
Geisler et al., "Model to Evaluate the Impact of Hospital-Based Interventions Targeting False-Positive Blood Cultures on Economic and Clinical Outcomes," J. Hospital Infection, vol. 102, No. 4, pp. 438-444 (Mar. 2019).
International Search Report and Written Opinion for International Application No. PCT/US2007/087951, mailed May 16, 2008, 8 pages.
International Search Report and Written Opinion for International Application No. PCT/US2013/043289, mailed Oct. 24, 2013, 15 pages.
International Search Report and Written Opinion for International Application No. PCT/US2013/052493, mailed Nov. 27, 2013, 7 pages.
International Search Report and Written Opinion for International Application No. PCT/US2013/063975, mailed Mar. 20, 2014, 16 pages.
International Search Report and Written Opinion for International Application No. PCT/US2013/071491, mailed Aug. 5, 2014, 9 pages.
International Search Report and Written Opinion for International Application No. PCT/US2013/072563, mailed Feb. 7, 2014, 11 pages.
International Search Report and Written Opinion for International Application No. PCT/US2013/073080, mailed Feb. 18, 2014, 14 pages.
International Search Report and Written Opinion for International Application No. PCT/US2016/037160, mailed Sep. 30, 2016, 15 pages.
International Search Report and Written Opinion for International Application No. PCT/US2016/050380, mailed Dec. 1, 2016, 6 pages.
International Search Report and Written Opinion for International Application No. PCT/US2018/036910, mailed Sep. 4, 2018, 13 pages.
International Search Report and Written Opinion for International Application No. PCT/US2018/050621, mailed Nov. 26, 2018, 11 pages.
International Search Report and Written Opinion for International Application No. PCT/US2018/064561, mailed Feb. 11, 2019, 9 pages.
International Search Report and Written Opinion for International Application No. PCT/US2019/034626, mailed Aug. 22, 2019, 16 pages.
International Search Report and Written Opinion for International Application No. PCT/US2020/022125, mailed May 26, 2020, 17 pages.

Lanteri et al., "Reduction of Blood Culture Contaminations in the Emergency Department," Department of Emergency Medicine, San Antonio Military Medical Center (2016), 1 page.
Marshall, L.A., et al.; "An injection molded microchip for nucleic acid purification from 25 microliter samples using isotachophoresis," J Chromatogr A.; 1331; pp. 139-142 (Feb. 2014).
Nielsen et al., "Initial Specimen Diversion Device Reduces Blood Culture Contamination and Vancomycin Use in Academic Medical Centre," J. Hospital Infection, vol. 120:127-133 (Feb. 2022).
Office Action for Australian Application No. 2018279941, mailed Mar. 20, 2023, 3 pages.
Office Action for Australian Application No. 2018334138, mailed Jun. 24, 2023, 3 pages.
Office Action for Australian Application No. 2020234829, mailed Nov. 15, 2024, 3 pages.
Office Action for Australian Application No. 2022200818, mailed May 11, 2023, 4 pages.
Office Action for Australian Application No. 2024203105, mailed Jan. 21, 2025, 3 pages.
Office Action for Australian Application No. 2024203140, mailed Apr. 8, 2025, 4 pages.
Office Action for Canadian Application No. 2932536, mailed Nov. 8, 2019, 6 pages.
Office Action for Canadian Application No. 2932536, mailed Oct. 23, 2020, 6 pages.
Office Action for Canadian Application No. 3074105, mailed Nov. 15, 2024, 5 pages.
Office Action for Canadian Application No. 3087992, mailed Mar. 20, 2025, 4 pages.
Office Action for Canadian Application No. 3101972, mailed May 13, 2025, 4 pages.
Office Action for Canadian Application No. 3120161, mailed Jun. 20, 2022, 4 pages.
Office Action for Canadian Application No. 3129065, mailed Feb. 11, 2025, 3 pages.
Office Action for Chinese Application No. 201380040468.7, mailed Jun. 30, 2016, with English Translation, 9 pages.
Office Action for Chinese Application No. 201380072185.0, mailed Sep. 28, 2016, with English Translation, 17 pages.
Office Action for Chinese Application No. 201811146373.4, mailed Apr. 8, 2025, with English translation, 18 pages.
Office Action for Chinese Application No. 201811146373.4, mailed Aug. 25, 2021, with English language translation, 10 pages.
Office Action for Chinese Application No. 201811146373.4, mailed Jan. 29, 2022, with English language translation, 21 pages.
Office Action for Chinese Application No. 201811146373.4, mailed Nov. 4, 2020, with English language translation, 17 pages.
Office Action for Chinese Application No. 201880050862.1, mailed Mar. 14, 2022, with English translation, 19 pages.
Office Action for Chinese Application No. 201880066848.0, mailed Apr. 20, 2022, with English Translation, 10 pages.
Office Action for Chinese Application No. 201880088771.7, mailed Sep. 3, 2021, with English translation, 17 pages.
Office Action for Chinese Application No. 202080025953.7, mailed Dec. 17, 2024, with English language translation, 22 pages.
Office Action for Chinese Application No. 202080025953.7, mailed May 24, 2025, with English language translation, 12 pages.
Office Action for Chinese Application No. 202080033513.6, mailed Oct. 9, 2022, with English translation, 19 pages.
Office Action for Chinese Application No. 202310257287.5, mailed Apr. 23, 2025, with English translation, 21 pages.
Office Action for European Application No. 20709440.0, mailed Feb. 18, 2025, 6 pages.
Office Action for European Application No. 20716348.6, mailed Jul. 12, 2022, 7 pages.
Office Action for Ex Parte Reexamination for U.S. Appl. No. 90/019,177, mailed Aug. 9, 2023, 11 pages.
Office Action for Ex Parte Reexamination for U.S. Appl. No. 90/019,177, mailed Dec. 1, 2023, 19 pages.
Office Action for Ex Parte Re-examination of U.S. Appl. No. 90/019,756, mailed Jun. 17, 2025, 38 pages.
Office Action for Ex Parte Re-examination of U.S. Appl. No. 90/019,757, mailed Jun. 17, 2025, 27 pages.

(56)      References Cited

OTHER PUBLICATIONS

Office Action for Israeli Application No. 313917, mailed May 29, 2025, 4 pages.
Office Action for Japanese Application No. 2015-545813, mailed Jul. 4, 2017, with English Translation, 14 pages.
Office Action for Japanese Application No. 2018-081980, mailed Feb. 21, 2019, with English Translation, 9 pages.
Office Action for Japanese Application No. 2018-081980, mailed Jan. 30, 2020, with English Translation, 11 pages.
Office Action for Japanese Application No. 2018-086721, mailed Mar. 15, 2019, with English Translation, 6 pages.
Office Action for Japanese Application No. 2019-230734, mailed Jan. 22, 2021, with English Translation, 9 pages.
Office Action for Japanese Application No. 2019-230734, mailed Jan. 5, 2022, with English Translation, 6 pages.
Office Action for Japanese Application No. 2020-075727, mailed Jul. 21, 2021, with English translation, 37 pages.
Office Action for Japanese Application No. 2020-094488, mailed Aug. 2, 2021, with English Translation, 4 pages.
Office Action for Japanese Application No. 2020-094488, mailed Mar. 31, 2022, with English Translation, 6 pages.
Office Action for Japanese Application No. 2020-511930, mailed Aug. 23, 2022, with English translation, 9 pages.
Office Action for Japanese Application No. 2020-517772, mailed Dec. 26, 2022, with English Translation, 6 pages.
Office Action for Japanese Application No. 2020-517772, mailed Mar. 14, 2022, with English Translation, 13 pages.
Office Action for Japanese Application No. 2020-550048, mailed Aug. 5, 2022, with English Translation, 5 pages.
Office Action for Japanese Application No. 2020-566232 mailed Apr. 12, 2023, with English translation, 27 pages.
Office Action for Japanese Application No. 2021-552145, mailed Jan. 15, 2024, with English Translation, 9 pages.
Office Action for Japanese Application No. 2022-074696 mailed Feb. 20, 2023, with English translation, 11 pages.
Office Action for Japanese Application No. 2022-184274, mailed Oct. 27, 2023, with English translation, 6 pages.
Office Action for Japanese Application No. 2022-552857, mailed Feb. 26, 2025, with English Translation, 10 pages.
Office Action for Japanese Application No. 2024-014849, mailed Apr. 30, 2025, with English translation, 9 pages.
Office Action for Japanese Application No. 2024-020482 mailed Mar. 11, 2025, with English Translation, 16 pages.
Office Action for Japanese Application No. 2024-115518, mailed Jun. 11, 2025, with English Translation, 6 pages.
Office Action for Japanese Application No. 2024-187934, mailed Apr. 28, 2025, with English translation, 12 pages.
Office Action for United Kingdom Application No. GB 1805101.1, mailed May 25, 2018, 8 pages.
Office Action for U.S. Appl. No. 11/955,635, mailed Dec. 3, 2010, 11 pages.
Office Action for U.S. Appl. No. 11/955,635, mailed Jul. 22, 2010, 11 pages.
Office Action for U.S. Appl. No. 13/335,241, mailed Apr. 20, 2012, 12 pages.
Office Action for U.S. Appl. No. 13/458,508, mailed Jul. 24, 2012, 13 pages.
Office Action for U.S. Appl. No. 13/675,295, mailed May 23, 2013, 15 pages.
Office Action for U.S. Appl. No. 13/952,964, mailed Mar. 20, 2015, 11 pages.
Office Action for U.S. Appl. No. 13/954,528, mailed Mar. 17, 2014, 10 pages.
Office Action for U.S. Appl. No. 14/089,267, mailed Jun. 19, 2014, 13 pages.
Office Action for U.S. Appl. No. 14/096,826, mailed Jul. 26, 2017, 12 pages.
Office Action for U.S. Appl. No. 14/096,826, mailed Mar. 8, 2018, 14 pages.
Office Action for U.S. Appl. No. 14/493,796, mailed Jan. 27, 2015, 7 pages.
Office Action for U.S. Appl. No. 14/494,208, mailed Jan. 27, 2015, 7 pages.
Office Action for U.S. Appl. No. 14/498,102, mailed Oct. 17, 2017, 20 pages.
Office Action for U.S. Appl. No. 14/498,102, mailed Sep. 24, 2018, 18 pages.
Office Action for U.S. Appl. No. 14/662,676, mailed Sep. 5, 2018, 25 pages.
Office Action for U.S. Appl. No. 14/712,437 mailed Oct. 25, 2018, 20 pages.
Office Action for U.S. Appl. No. 14/728,318, mailed Jul. 18, 2019, 27 pages.
Office Action for U.S. Appl. No. 14/926,784, mailed Jan. 15, 2019, 15 pages.
Office Action for U.S. Appl. No. 14/926,784, mailed Jan. 21, 2020, 17 pages.
Office Action for U.S. Appl. No. 14/926,784, mailed May 25, 2018, 15 pages.
Office Action for U.S. Appl. No. 15/088,842, mailed Nov. 23, 2016, 20 pages.
Office Action for U.S. Appl. No. 15/180,454, mailed Apr. 1, 2020, 28 pages.
Office Action for U.S. Appl. No. 15/180,454, mailed Jan. 21, 2021, 24 pages.
Office Action for U.S. Appl. No. 15/180,454, mailed Jul. 25, 2019, 27 pages.
Office Action for U.S. Appl. No. 15/432,310, mailed Apr. 12, 2017, 14 pages.
Office Action for U.S. Appl. No. 15/435,684, mailed Jun. 12, 2017, 19 pages.
Office Action for U.S. Appl. No. 15/448,891, mailed Jun. 16, 2017, 25 pages.
Office Action for U.S. Appl. No. 15/457,082, mailed Jun. 15, 2017, 22 pages.
Office Action for U.S. Appl. No. 15/829,015, mailed Feb. 6, 2018, 24 pages.
Office Action for U.S. Appl. No. 15/829,018, mailed Feb. 16, 2018, 13 pages.
Office Action for U.S. Appl. No. 15/829,023, mailed Feb. 7, 2018, 25 pages.
Office Action for U.S. Appl. No. 15/832,055, mailed Feb. 8, 2018, 21 pages.
Office Action for U.S. Appl. No. 15/832,087, mailed Feb. 7, 2018, 24 pages.
Office Action for U.S. Appl. No. 15/832,091, mailed Feb. 22, 2018, 16 pages.
Office Action for U.S. Appl. No. 15/854,273, mailed Jan. 13, 2020, 13 pages.
Office Action for U.S. Appl. No. 15/854,273, mailed Mar. 15, 2019, 19 pages.
Office Action for U.S. Appl. No. 15/854,273, mailed Sep. 7, 2018, 15 pages.
Office Action for U.S. Appl. No. 15/925,159, mailed May 14, 2019, 15 pages.
Office Action for U.S. Appl. No. 15/925,159, mailed Nov. 26, 2018, 11 pages.
Office Action for U.S. Appl. No. 16/004,955, mailed Feb. 16, 2021, 28 pages.
Office Action for U.S. Appl. No. 16/129,066, mailed Sep. 3, 2020, 13 pages.
Office Action for U.S. Appl. No. 16/213,005, mailed Feb. 3, 2021, 15 pages.
Office Action for U.S. Appl. No. 16/255,055, mailed Mar. 18, 2019, 16 pages.
Office Action for U.S. Appl. No. 16/255,058, mailed Mar. 30, 2021, 16 pages.
Office Action for U.S. Appl. No. 16/274,835, mailed Feb. 12, 2021, 17 pages.
Office Action for U.S. Appl. No. 16/299,962, mailed Dec. 26, 2019, 14 pages.

(56)                    References Cited

OTHER PUBLICATIONS

Office Action for U.S. Appl. No. 16/299,962, mailed Dec. 9, 2020, 15 pages.
Office Action for U.S. Appl. No. 16/299,962, mailed Jun. 15, 2021, 17 pages.
Office Action for U.S. Appl. No. 16/299,962, mailed May 2, 2019, 14 pages.
Office Action for U.S. Appl. No. 16/376,745, mailed May 14, 2021, 13 pages.
Office Action for U.S. Appl. No. 16/379,128, mailed Apr. 26, 2022, 14 pages.
Office Action for U.S. Appl. No. 16/426,380, mailed May 7, 2021, 28 pages.
Office Action for U.S. Appl. No. 16/426,380, mailed Oct. 30, 2020, 29 pages.
Office Action for U.S. Appl. No. 16/789,034, mailed Feb. 9, 2023, 11 pages.
Office Action for U.S. Appl. No. 16/815,526, mailed Aug. 18, 2022, 13 pages.
Office Action for U.S. Appl. No. 16/934,975, mailed Oct. 6, 2022, 18 pages.
Office Action for U.S. Appl. No. 17/136,882, mailed Dec. 31, 2024, 6 pages.
Office Action for U.S. Appl. No. 17/136,882, mailed Jun. 9, 2023, 11 pages.
Office Action for U.S. Appl. No. 17/136,882, mailed Nov. 8, 2023, 11 pages.
Office Action for U.S. Appl. No. 17/138,056, mailed Dec. 21, 2022, 11 pages.
Office Action for U.S. Appl. No. 17/193,930, mailed Mar. 17, 2025, 15 pages.
Office Action for U.S. Appl. No. 17/388,971, mailed Nov. 23, 2021, 19 pages.
Office Action for U.S. Appl. No. 17/388,979, mailed Dec. 8, 2021, 21 pages.
Office Action for U.S. Appl. No. 17/390,249, mailed Nov. 8, 2023, 9 pages.
Office Action for U.S. Appl. No. 17/403,500, mailed Jul. 28, 2023, 28 pages.
Office Action for U.S. Appl. No. 17/403,500, mailed Nov. 13, 2024, 27 pages.
Office Action for U.S. Appl. No. 17/403,500, mailed Sep. 27, 2022, 29 pages.
Office Action for U.S. Appl. No. 17/516,887, mailed Jan. 13, 2025, 42 pages.
Office Action for U.S. Appl. No. 17/525,682, mailed Feb. 7, 2022, 12 pages.
Office Action for U.S. Appl. No. 17/532,382 mailed Feb. 7, 2022, 10 pages.
Office Action for U.S. Appl. No. 17/583,791, mailed Dec. 23, 2024, 19 pages.
Office Action for U.S. Appl. No. 17/591,237, dated May 3, 2022, 20 pages.
Office Action for U.S. Appl. No. 17/591,237, mailed Aug. 25, 2023, 25 pages.
Office Action for U.S. Appl. No. 17/591,237, mailed Aug. 4, 2022, 26 pages.
Office Action for U.S. Appl. No. 17/591,237, mailed Feb. 16, 2023, 34 pages.
Office Action for U.S. Appl. No. 17/591,237, mailed Jan. 24, 2025, 34 pages.
Office Action for U.S. Appl. No. 17/591,239, mailed Aug. 23, 2023, 23 pages.
Office Action for U.S. Appl. No. 17/591,239, mailed Aug. 4, 2022, 26 pages.
Office Action for U.S. Appl. No. 17/591,239, mailed Feb. 17, 2023, 34 pages.
Office Action for U.S. Appl. No. 17/591,239, mailed Jan. 24, 2025, 32 pages.

Office Action for U.S. Appl. No. 17/591,239, mailed May 3, 2022, 21 pages.
Office Action for U.S. Appl. No. 17/684,920, mailed Jan. 31, 2023, 9 pages.
Office Action for U.S. Appl. No. 17/684,920, mailed Jul. 11, 2022, 12 pages.
Office Action for U.S. Appl. No. 17/710,389, mailed Jun. 16, 2022, 25 pages.
Office Action for U.S. Appl. No. 17/710,401, mailed Jul. 6, 2022, 22 pages.
Office Action for U.S. Appl. No. 17/710,411, mailed Jul. 6, 2022, 22 pages.
Office Action for U.S. Appl. No. 17/863,605, mailed Nov. 28, 2023, 15 pages.
Office Action for U.S. Appl. No. 17/869,256, mailed May 5, 2025, 24 pages.
Office Action for U.S. Appl. No. 18/380,259, mailed Jan. 29, 2024, 33 pages.
Office Action for U.S. Appl. No. 18/381,369, mailed Nov. 28, 2023, 16 pages.
Office Action for U.S. Appl. No. 18/680,331, mailed Mar. 25, 2025, 8 pages.
Office Action for U.S. Appl. No. 18/680,348, mailed Mar. 25, 2025, 7 pages.
Office Action for U.S. Appl. No. 18/680,377, mailed Mar. 26, 2025, 12 pages.
Office Action for U.S. Appl. No. 18/680,439, mailed Mar. 31, 2025, 8 pages.
Office Action for U.S. Appl. No. 18/680,466, mailed Dec. 30, 2024, 7 pages.
Office Action for U.S. Appl. No. 18/960,441, mailed Jan. 17, 2025, 8 pages.
Office Action for U.S. Appl. No. 18/990,547, mailed Jan. 31, 2025, 10 pages.
Order Granting Request for Ex Parte Reexamination for U.S. Appl. No. 90/019,177, mailed Apr. 26, 2023, 16 pages.
Order Granting Request for Ex Parte Reexamination for U.S. Appl. No. 90/019,823, dated Feb. 24, 2025, 16 pages.
Order Granting Request for Ex Parte Reexamination for U.S. Appl. No. 90/019,824, dated Feb. 24, 2025, 18 pages.
Order Granting Request for Ex Parte Reexamination for U.S. Appl. No. 90/019,825, dated Feb. 25, 2025, 15 pages.
Povroznik, "Initial Specimen Diversion Device Utilization Mitigates Blood Culture Contamination Across Regional Community Hospital and Acute Care Facility," Am. J. Medical Quality, vol. 37, No. 5, 405 (Mar. 2022), 8 pages.
Rupp et al., "Reduction in Blood Culture Contamination Through Use of Initial Specimen Diversion Device," Clinical Infectious Diseases, vol. 65, No. 2, 201 (Jul. 15, 2017), 19 pages.
Shen, H., et al.; "A microfluidic chip based sequential injection system with trapped droplet liquid-liquid extraction and chemiluminescence detection," Lab Chip; 6(10):1387-1389 (Oct. 2006).
Skoglund et al., "Estimated Clinical and Economic Impact through Use of a Novel Blood Collection Device to Reduce Blood Culture Contamination in the Emergency Department: a Cost-Benefit Analysis," J Clin Microbiol. (Jan. 2019); 57(1):e01015-18, 10 pages.
Steed et al., "Study Demonstrates Reduction in Blood Culture Contamination Rates with Novel Blood Culture Collection Device," Clinical Lab Products Magazine (Feb. 2018), 2 pages.
Supplementary European Search Report for European Application No. 13797732.8, mailed Dec. 7, 2015, 5 pages.
Supplementary European Search Report for European Application No. 13860741.1, mailed Jun. 7, 2016, 5 pages.
Tompkins et al., "Getting to Zero: Impact of a Device to Reduce Blood Culture Contamination and False-Positive Central-Line-Associated Bloodstream Infection," Infection Control & Hospital Epidemiology, pp. 1-5 (Nov. 2022).
Tongma et al., "Significant Reduction of Blood Culture Contamination in the Emergency Department (ED) Using the Steripath® Blood Diversion Device," Open Forum Infectious Diseases, vol. 4, Supp. 1, 2035 (Oct. 2017), 1 page.

(56)            References Cited

OTHER PUBLICATIONS

Zimmerman et al., "Reducing Blood Culture Contamination Using an Initial Specimen Diversion Device," Am. J. Infection Control, vol. 47, No. 7, pp. 822-826 (Jan. 2019).
Extended European Search Report for European Application No. 25164992.7, mailed Aug. 26, 2025, 8 pages.
Office Action for Australian Application No. 2020234829, mailed Sep. 11, 2025, 3 pages.
Office Action for Australian Application No. 2024205062, mailed Sep. 8, 2025, 2 pages.
Office Action for Canadian Application No. 3132981, mailed Aug. 22, 2025, 5 pages.
Office Action for Chinese Application No. 201811146373.4, mailed Jul. 28, 2025, with English translation, 36 pages.
Office Action for European Application No. 21715060.6, mailed Sep. 1, 2025, 10 pages.
Office Action for European Application No. 23182529.0, mailed Jul. 29, 2025, 6 pages.
Office Action for Ex Parte Reexamination for U.S. Appl. No. 90/019,823, mailed Aug. 25, 2025, 30 pages.
Office Action for Israeli Application No. 286263, mailed Aug. 5, 2025, 3 pages.
Office Action for Israeli Application No. 309638, mailed Aug. 11, 2025, 3 pages.
Office Action for Japanese Application No. 2024-153369, mailed Sep. 5, 2025, with English translation, 10 pages.
Office Action for U.S. Appl. No. 14/838,794, mailed Aug. 3, 2017, 8 pages.
Office Action for U.S. Appl. No. 17/516,887, mailed Aug. 13, 2025, 24 pages.
Office Action for U.S. Appl. No. 17/591,237, mailed Aug. 20, 2025, 24 pages.
Office Action for U.S. Appl. No. 18/680,466, mailed Aug. 20, 2025, 10 pages.
Office Action for U.S. Appl. No. 19/175,765, mailed Aug. 8, 2025, 11 pages.
Patent Trial and Appeal Board Decision in Ex Parte Reexamination U.S. Appl. No. 90/019,177, dated May 20, 2025, Exhibit 1003, 22 pages.
Request for Ex Parte Reexamination for U.S. Pat. No. 10,039,483 Under 35 U.S.C. § 302 and 37 C.F.R. § 1.510, filed Jul. 21, 2025, 66 pages.
Request for Ex Parte Reexamination for U.S. Pat. No. 10,039,483 Under 35 U.S.C. § 302 and 37 C.F.R. § 1.510 filed Mar. 22, 2023, 84 pages.
Becton, Dickinson and Company "BD Bactec™ Blood Culture System," [Retrieval Date Unknown] available online URL:https:// www.bd.com/en-us/products-and-solutions/products/product-families/ bd-bactec-blood-culture-system; 9 pages (Publication Date Unknown).
Biomerieux "Bact/Alert® Culture Media: Strong Outside, Strong Inside," PRN 054364 Rev.01A; [Online Retrieval Date Unknown]; URL: https://www.biomerieux.com/US/en/our-offer/clinical-products/ bact-alert-culture-media-bottles.html; 10 pages (Publication Date Unknown ).
Buzard, B.A., et al.; "Evaluation of an Initial Specimen Diversion Device (ISDD) on Rates of Blood Culture Contamination in the Emergency Department," Jun. 22, 2020; Kans J Med.; 14(1):73-76 (Mar. 19, 2021).
Callado, G.Y., et al.; "Diagnostic Stewardship: A Systematic Review and Meta-analysis of Blood Collection Diversion Devices Used to Reduce Blood Culture Contamination and Improve the Accuracy of Diagnosis in Clinical Settings," Open Forum Infect Dis.; 10(9):ofad433; pp. 1-10. doi: 10.1093/ofid/ofad433 (Aug. 11, 2023).
ENA (Emergency Nurses Association) "Clinical Practice Guideline: Synopsis—Prevention of Blood Culture Contamination," last updated Jan. 9, 2023 [Retrieval Date Unknown] accessed online URL:https:// www.guidelinecentral.com/guideline/308349/#section-420; 1 page (May 8, 2018).

Ex Parte Reexamination Interview Summary for U.S. Appl. No. 90/019,756, mailed Sep. 17, 2025, 7 pages.
Ex Parte Reexamination Interview Summary for U.S. Appl. No. 90/019,757, mailed Sep. 17, 2025, 7 pages.
Kurin "Changing Blood Culture Collection in Hospitals Across America, Clinical Evidence, Studies" [Retrieved online Sep. 15, 2025] URL:https://www.kurin.com/studies/; 22 pages (Publication Date Unknown).
Kurin "Changing Blood Culture Collection in Hospitals Across America," [Retrieved online Sep. 15, 2025] URL:https://www.kurin. com/clinical-guidelines/; 11 pages (Publication Date Unknown).
Kurin "False Positive Blood Cultures—Improve the accuracy of blood culture," [Retrieved online Sep. 15, 2025] URL:https://www. kurin.com/false-positive-blood-cultures/; 5 pages (Publication Date Unknown).
Kurin "Kurin® Jet™ Blood Culture Collection Ordering Information," Brochure [Retrieval Date Unknown] available online URL: https://www.kurin.com/kurin-jet/ 2 pages (Publication Date Unknown).
Kurin "Kurin Launches Kurin Jet, Redefining the Blood Culture Contamination Device Market," [Retrieval Date Unknown] URL:https:// www.kurin.com/kurin-launches-kurin-jet-redefining-the-blood-culture- contamination-device-market/; 5 pages (Publication Date Unknown).
Kurin "Kurin Lock® with Flash Technology: Better than conventional diversion," [Retrieved online Sep. 26, 2025] URL:https:// www.kurin.com/kurin-jet/; 10 pages (Publication Date Unknown).
Kurin "Lowering the 3% Blood Culture Contamination Rate Benchmark," [Retrieved online Sep. 15, 2025] URL:https://www.kurin. com/3-percent-standard/; 4 pages (Publication Date Unknown).
Kurin "The Financial and Clinical Costs of False Positive Blood Cultures," [Retrieved online Sep. 15, 2025] URL:https://www.kurin. com/false-positives-blood-culture-cost/; 5 pages (Publication Date Unknown).
Magnolia Medical Technologies, Inc.; "Newly Released CLSI National Blood Culture Guidelines Identify Best Practices and Evidence-Based Technology Solutions Such as Steripath® to Improve Patient Safety and Outcomes," [Retrieved online Sep. 15, 2025] URL: https://magnolia-medical.com/news/newly-released-clsi-national- blood-culture-guidelines-identify-best-practices-and-evidence-based- technology-solutions-such-as-steripath-to-improve-patient-safety- and-outcomes/; 5 pages (May 5, 2022).
Mohajer, M.A., et al.; "The Impact of Initial Specimen Diversion Systems on Blood Culture Contamination," Open Forum Infect Dis .; 10(5): ofad182; pp. 1-6. doi: 10.1093/ofid/ofad182 (Apr. 5, 2023).
Office Action for Chinese Application No. 202180032541.0, mailed Sep. 23, 2025, with English translation, 19 pages.
Office Action for U.S. Appl. No. 17/193,930, mailed Oct. 8, 2025, 13 pages.
Snyder, S.R., et al.; "Effectiveness of practices to reduce blood culture contamination: A Laboratory Medicine Best Practices systematic review and meta-analysis," Clin Biochem.; Epub Jun. 16, 2012; 45(Issues 13-14):999-1011. doi: 10.1016/j.clinbiochem.2012. 06.007, 13 pages (Sep. 2012).
Valleywise Health Medical Center Case Study "In anticipation of CMS changes, AZ hospital identifies solution to blood culture contaminations with new Kurin Jet," Brochure; 1 page (Publication Date Unknown).
Widmer, A.F., et al.; "Sterilization of skin and catheters before drawing blood cultures," J Clin Microbiol.; 41(10):4910; 1 page (Oct. 2003).
Wilber, E.P., et al.; "Effect of an initial specimen diversion device on blood-culture contamination rates and vancomycin usage: A quasi-experimental study," Epub Aug. 3, 2023; Infect Control Hosp Epidemiol.; 45(1):100-102 (Jan. 2024).
Zwang, O., et al.; "Analysis of strategies to improve cost effectiveness of blood cultures," J Hosp Med.; 1(5):272-276. doi: 10.1002/ jhm.115 (Sep. 2006).

* cited by examiner

DEVICES AND METHODS FOR BODILY FLUID COLLECTION AND DISTRIBUTION

CROSS-REFERENCE TO RELATED APPLICATIONS

This application is a continuation of U.S. patent application Ser. No. 16/785,170 entitled, "Devices and Methods for Bodily Fluid Collection and Distribution," filed Feb. 7, 2020, which claims priority to and the benefit of U.S. Provisional Patent Application Ser. No. 62/802,999 entitled, "Devices and Methods for Bodily Fluid Collection and Distribution," filed Feb. 8, 2019, the disclosure of each of which is incorporated herein by reference in its entirety.

BACKGROUND

Embodiments described herein relate generally to the procurement of bodily fluid samples, and more particularly to devices and methods for procuring and distributing bodily fluid samples with reduced contamination.

Health care practitioners routinely perform various types of microbial as well as other broad diagnostic tests on patients using parenterally obtained bodily fluids. As advanced diagnostic technologies evolve and improve, the speed, accuracy (both sensitivity and specificity), and value of information that can be provided to clinicians continues to improve. Collecting the proper (e.g., recommended) and/or desired volume and maintaining the integrity of the bodily fluid sample during and/or after collection help to ensure analytical diagnostic results are representative of the in vivo conditions of a patient. Examples of diagnostic technologies that are reliant on high quality, non-contaminated, and/or unadulterated bodily fluid samples include but are not limited to microbial detection, molecular diagnostics, genetic sequencing (e.g., deoxyribonucleic acid (DNA), ribonucleic acid (RNA), next-generation sequencing (NGS), etc.), biomarker identification, and the like.

One source of inaccurate results from such testing is the presence of biological matter, which can include cells external to the intended source for sample procurement and/or other external contaminants inadvertently included in the bodily fluid sample being analyzed. In short, when the purity of the sample intended to be derived or collected from a specific bodily fluid source is compromised during the specimen procurement process, resultant analytical test results may be inaccurate, distorted, adulterated, falsely positive, falsely negative, and/or otherwise not representative of the actual condition of the patient, which in turn, can inform faulty, inaccurate, confused, unsure, low-confidence, and/or otherwise undesired clinical decision making.

Another source of false positive results and/or false negative results can be an incorrect and/or inappropriate volume of the patient sample for a given type of testing. For example, overfilling of volume-sensitive blood culture bottles can lead to false positive results as noted in the instructions for use and/or warning labeling from manufacturers of such culture bottles, as well as associated automated continuous monitoring microbial detection systems. On the other hand, insufficient patient sample volume within a culture medium can result in false negative results.

As such, a need exists for devices and methods for procuring bodily fluid samples with reduced contamination. Additionally, a need exists for devices and methods for accurately metering, measuring, and/or distributing one or more sample volume(s) of the procured bodily fluid into one or more sample reservoir(s) used, for example, in bodily fluid sample testing.

SUMMARY

Devices and methods for procuring and/or distributing a proper, appropriate, and/or recommended volume of a bodily fluid sample with reduced contamination are described herein. In some embodiments, an apparatus includes a housing, an inlet adapter, an actuator, and a volume indicator. The housing defines a fluid reservoir and includes a port that is in fluid communication with the fluid reservoir. The inlet adapter is removably coupleable to the housing and places the port in fluid communication with a bodily fluid source when coupled to the housing. The actuator includes a plunger disposed within and defining at least a part of the fluid reservoir. A portion of the actuator is configured to be engaged by a user to move the plunger within the housing from a first position in which the fluid reservoir has a first volume, to a second position in which the fluid reservoir has a second volume greater than the first volume. The increase in volume is operable to draw bodily fluid into the fluid reservoir via the inlet adapter. The actuator modulates a rate of motion of the plunger below a threshold as the plunger is moved from the first position to the second position. The volume indicator is configured to transition from a first state to a second state in response to a predetermined volume of bodily fluid being disposed in the fluid reservoir. The inlet adapter is configured to be removed from the housing after the predetermined volume of bodily fluid is transferred into the fluid reservoir to allow transfer of the predetermined volume to a sample bottle external to the housing via the port.

DETAILED DESCRIPTION

Figure 1C:
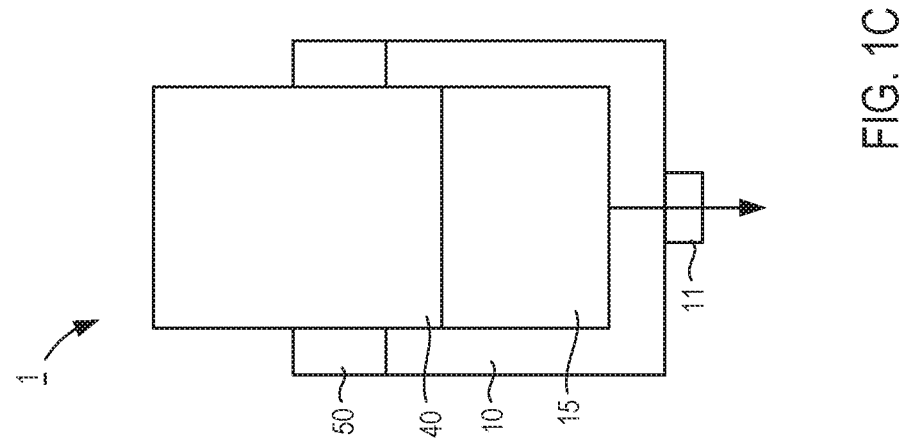
FIGS. 1A-1C are schematic illustrations of a bodily fluid collection and distribution device according to an embodiment and shown in a first state, a second state, and a third state, respectively.

In some instances, patient samples are tested for the presence of one or more potentially undesirable microbes, such as bacteria, fungi, or yeast (e.g., *Candida*). Various technologies can be employed to assist in the detection of the presence of microbes as well as other types of biological matter, specific types of cells, biomarkers, proteins, antigens, enzymes, blood components, and/or the like during diagnostic testing. Examples include but are not limited to molecular polymerase chain reaction (PCR), magnetic resonance and other magnetic analytical platforms, automated microscopy, spatial clone isolation, flow cytometry, whole blood ("culture free") specimen analysis (e.g., NGS) and associated technologies, morphokinetic cellular analysis, and/or other common or evolving and advanced technologies utilized in the clinical laboratory environment to characterize patient specimens and/or to detect, identify, type, categorize, and/or characterize specific organisms, antibiotic susceptibilities, and/or the like.

In some instances, microbial testing may include incubating patient samples in one or more vessels that may contain culture media, common additives, and/or other types of solutions conducive to microbial growth for a period of time (e.g., a variable amount of time from less than an hour to a few hours to several days—which can be longer or shorter depending on the diagnostic technology employed). Microbes and/or organisms present in the patient sample flourish and/or grow over time in the culture medium, which can be detected by automated, continuous monitoring, and/or other methods specific to the analytical platform and technology used for detection, identification, and/or the like. The presence of microbes and/or organisms in the culture medium (as indicated by observation of carbon dioxide and/or via other detection methods) suggests the presence of the same microbes and/or organisms in the patient sample which, in turn, suggests the presence of the same microbes and/or organisms in the bodily fluid of the patient from whom the sample was obtained. In other instances, a bodily fluid sample may be analyzed directly (i.e., not incubated) for the presence of microbes and/or organisms. Accordingly, when microbes are determined to be present in the sample used for testing, the patient may be diagnosed and prescribed one or more antibiotics or other treatments specifically designed to treat or otherwise remove the undesired microbes and/or organisms from the patient.

Patient samples, however, can become contaminated during procurement and/or otherwise can be susceptible to false positive or false negative results. For example, microbes from a bodily surface (e.g., dermally residing microbes) that are dislodged during the specimen procurement process (e.g., either directly or indirectly via tissue fragments, hair follicles, sweat glands, and other skin adnexal structures) can be subsequently transferred to a culture medium, test vial, or other suitable specimen collection or transfer vessel with the patient sample and/or otherwise included in the specimen that is to be analyzed. Another possible source of contamination is from the person drawing the patient sample (e.g., a doctor, phlebotomist, nurse, technician, etc.). Specifically, equipment, supplies, and/or devices used during a patient sample procurement process often include multiple fluidic interfaces (by way of example, but not limited to, patient to needle, needle to transfer adapter, transfer adapter to sample vessel, catheter hub to syringe, syringe to transfer adapter, needle/tubing to sample vessels, and/or any other fluidic interface or any combination thereof), each of which can introduce points of potential contamination. In some instances, such contaminants may thrive in a culture medium and/or may be identified by another non-culture based diagnostic technology and eventually may yield a false positive microbial test result, which may inaccurately reflect the presence or lack of such microbes within the patient (i.e., in vivo).

In some instances, false positive results and/or false negative results can be attributed to an incorrect and/or inappropriate volume of the patient sample for a given type of testing. For example, overfilling of volume-sensitive blood culture bottles can lead to false positive results as noted in the instructions for use and/or warning labeling from manufacturers of such culture bottles, as well as associated automated continuous monitoring microbial detection systems. On the other hand, insufficient patient sample volume within a culture medium can result in false negative results (e.g., failing to identify microbes actually present within the patient).

Such inaccurate results because of contamination, adulteration, and/or inaccurate sample volume are a concern when attempting to diagnose or treat a wide range of suspected illnesses, diseases, infections, patient conditions, and/or other maladies of concern. For example, false negative results from microbial tests may result in a misdiagnosis and/or delayed treatment of a patient illness, which, in some cases, could result in the death of the patient. Conversely, false positive results from microbial tests may result in the patient being unnecessarily subjected to one or more antimicrobial therapies, which may cause serious side effects to the patient including, for example, death, as well as produce an unnecessary burden and expense to the health care system due to extended length of patient stay and/or other complications associated with erroneous treatments. The use of diagnostic imaging equipment to arrive at these false results is also a concern from both a cost perspective and a patient safety perspective as unnecessary exposure to concentrated radiation associated with a variety of imaging procedures (e.g., CT scans) has many known adverse impacts on long-term patient health. Moreover, challenges exist with training medical professionals to withdraw accurate, desired, and/or recommended sample volumes and/or otherwise with ensuring accurate, desired, and/or recommended sample volumes are used according to the specific testing to be performed.

In some embodiments, an apparatus includes a housing, an inlet adapter, an actuator, and a volume indicator. The housing defines a fluid reservoir and includes a port that is in fluid communication with the fluid reservoir. The inlet adapter is removably coupleable to the housing and places the port in fluid communication with a bodily fluid source when coupled to the housing. The actuator includes a plunger disposed within and defining at least a part of the fluid reservoir. A portion of the actuator is configured to be engaged by a user to move the plunger within the housing from a first position in which the fluid reservoir has a first volume, to a second position in which the fluid reservoir has a second volume greater than the first volume. The increase in volume is operable to draw bodily fluid into the fluid reservoir via the inlet adapter. The actuator modulates a rate of motion of the plunger below a threshold as the plunger is moved from the first position to the second position. The volume indicator is configured to transition from a first state to a second state in response to a predetermined volume of bodily fluid being disposed in the fluid reservoir. The inlet adapter is configured to be removed from the housing after the predetermined volume of bodily fluid is transferred into the fluid reservoir to allow transfer of the predetermined volume to a sample bottle external to the housing via the port.

In some embodiments, an apparatus includes a housing, an inlet adapter, an actuator, and a volume indicator. The housing defines a fluid reservoir and includes a port that is in fluid communication with the fluid reservoir. The inlet adapter is removably coupleable to the housing and places the port in fluid communication with a bodily fluid source when coupled to the housing. The actuator includes a plunger disposed within and defining at least a part of the fluid reservoir. The actuator is configured to move the plunger within the housing between a first position and a second position. The fluid reservoir has a first volume when the plunger is in the first position and a second volume greater than the first volume when the plunger is in the second position. An increase in the volume of the fluid reservoir is operable to draw bodily fluid into the fluid reservoir via the inlet adapter. The volume indicator transitions from a first state to a second state associated with a predetermined volume of bodily fluid being transferred into the fluid reservoir. The predetermined volume is less than the second volume of the fluid reservoir. The volume indicator is configured to at least temporarily stop the plunger from being moved toward the second position when in the second state.

In some embodiments, a method includes placing an inlet adapter of a fluid transfer device in fluid communication with a bodily fluid source. The inlet adapter is removably coupleable to a housing of the fluid transfer device such that a port fluidically couples the inlet adapter to a fluid reservoir defined by the housing. An actuator of the fluid transfer device is engaged to move a plunger disposed within and defining at least a part of the fluid reservoir from a first position toward a second position. The movement of the plunger produces a negative pressure operable to draw bodily fluid into the fluid reservoir via the inlet adapter. A volume indicator is transitioned from a first state to a second state when a predetermined volume of bodily fluid is transferred into the fluid reservoir. The plunger is stopped prior to the plunger being moved to the second position in response to the transitioning of the volume indicator from the first state to the second state. The inlet adapter is removed from the housing and from the housing and the predetermined volume of bodily fluid is transferred from the fluid reservoir to a sample bottle external to the fluid transfer device via the port.

In some embodiments, an apparatus includes a housing, an inlet adapter, an actuator, and a volume indicator. The housing defines a fluid reservoir and includes a port in fluid communication with the fluid reservoir. The inlet adapter is at least temporarily coupled to the housing and is in fluid communication with the port. The inlet adapter is configured to place the port in fluid communication with a bodily fluid source. The actuator includes a plunger disposed within and defining at least a part of the fluid reservoir and an engagement member configured to be engaged by a user to move the plunger within the housing. The actuator is configured to modulate a rate at which the plunger is moved from a first position, in which the fluid reservoir has a first volume, to a second position, in which the fluid reservoir has a second volume greater than the first volume. The increase in volume of the fluid reservoir is operable to draw a volume of bodily fluid into the fluid reservoir. The volume indicator is configured to transition from a first state to a second state in response to a predetermined volume of bodily fluid being disposed in the fluid reservoir.

In some embodiments, a bodily fluid collection and distribution device can be configured to procure a proper, appropriate, and/or recommended volume of a bodily fluid sample with reduced contamination. In some embodiments, the bodily fluid collection and distribution device and/or a diversion device coupled thereto can divert an initial volume of a bodily fluid into a pre-sample reservoir. The initial volume of bodily fluid is sequestered in or by the bodily fluid collection and distribution device and/or the diversion device before permitting a subsequent volume of bodily fluid to flow into a fluid reservoir defined, at least in part, by the bodily fluid collection and distribution device. In some instances, the initial volume of bodily fluid can include microbes and/or other contaminants and sequestering the initial volume can reduce or substantially prevent microbes and/or other contaminants in the subsequent volume of bodily fluid (e.g., a sample volume of bodily fluid). In this manner, the subsequent volume of bodily fluid can be used for diagnostic or other testing, while the initial volume of bodily fluid can be discarded, reinfused into the patient, and/or used for diagnostic and/or other testing that is not sensitive to the potential microbes and/or other contaminants.

In some embodiments, a bodily fluid collection and distribution device can include an actuator that can be engaged and/or manipulated by a user to draw a volume of bodily fluid (e.g., after an initial volume of the bodily fluid is diverted). For example, one or more portions of the actuator can be moved within and/or relative to a fluid reservoir of the bodily fluid collection and distribution device to draw the volume of bodily fluid into the fluid reservoir. In some instances, the actuator can be configured to control, modulate, and/or limit a rate at which one or more portions of the actuator can be moved, which in turn, can allow the user to control the volume of bodily fluid transferred into the fluid reservoir and/or a magnitude of a negative pressure or suction force exerted on or at the bodily fluid source (e.g., within the vein of the patient).

In some embodiments, a bodily fluid collection and distribution device can include a volume indicator configured to ensure the proper and/or desired volume of bodily fluid is collected and/or transferred into the fluid reservoir defined by the bodily fluid collection and distribution device. The bodily fluid collection and/or distribution device can be configured to automatically divert and/or control the fluid flow into and/or out of the fluid reservoir. For example, after a first metered or predetermined volume of bodily fluid is collected, the volume indicator can be configured to transition from a first state to a second state. In some embodiments, the volume indicator can provide an indication to a user when placed in the second state that is indicative of the metered and/or predetermined volume of bodily fluid being disposed in the fluid reservoir. In addition or as an alternative, the volume indicator can be configured to gate, control, limit, and/or substantially prevent an additional amount of bodily fluid from being conveyed into the fluid reservoir until and/or unless the user engages and/or manipulates the volume indicator to transition the volume indicator away from the second state (e.g., toward the first state or a third state different from the first state and the second state). For example, in some instances, the user may transition the volume indicator away from the second state to convey an additional amount of bodily fluid into the fluid reservoir.

In some embodiments, the bodily fluid collection and distribution device can be configured to convey the volume of bodily fluid contained in the fluid reservoir into one or more sample vessels, culture bottles, sample reservoirs and/or vials, testing assays, and/or the like. For example, the user can manipulate the bodily fluid collection and distribution device (e.g., the actuator and/or other suitable portion of the device) to convey a predetermined and/or desired volume of bodily fluid from the fluid reservoir into, for example, a culture bottle. In some embodiments, the volume indicator can control, regulate, and/or distribute the bodily fluid flowing from the fluid reservoir to the culture bottle. For example, in some embodiments, the volume indicator can automatically transition to a state in which a flow of bodily fluid is substantially gated and/or prevented from being conveyed from the fluid reservoir in response to a predetermined and/or desired volume of bodily fluid being conveyed into the culture bottle. As such, the bodily fluid collection and distribution device can ensure that a known, predetermined, and/or desired volume of bodily fluid is conveyed into the culture bottle.

These concepts, features, and/or aspects—along with other concepts, features, and/or aspects—are described in further detail herein and/or are shown in the drawings with respect to specific embodiments.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about," "approximate," and/or "substantially" when used in connection with a stated value and/or other geometric relationships is intended to convey that the structure so defined is nominally the value stated and/or the geometric relationship described. In some instances, the terms "about," "approximately," and/or "substantially" can generally mean and/or can generally contemplate plus or minus 10% of the value or relationship stated. For example, about 0.01 would include 0.009 and 0.011, about 0.5 would include 0.45 and 0.55, about 10 would include 9 to 11, and about 1000 would include 900 to 1100. While a value stated may be desirable, it should be understood that some variance may occur as a result of, for example, manufacturing tolerances, physiology and/or physical characteristics, or other practical considerations (such as, for example, the pressure or force applied through a portion of a device, conduit, lumen, etc.). Accordingly, the terms "about," "approximately," and/or "substantially" can be used herein to account for such tolerances and/or considerations.

As described in further detail herein, any of the devices and methods can be used to procure bodily fluid samples with reduced contamination by, for example, diverting a "pre-sample" volume of bodily fluid prior to collecting a "sample" volume of bodily fluid. As used herein, "bodily fluid" can include any fluid obtained directly or indirectly from a body of a patient. For example, "bodily fluid" includes, but is not limited to, blood, cerebrospinal fluid, urine, bile, lymph, saliva, synovial fluid, serous fluid, pleural fluid, amniotic fluid, mucus, sputum, vitreous, air, and the like, or any combination thereof.

The terms "pre-sample," "first," and/or "initial," can be used interchangeably to describe and/or refer to an amount, portion, or volume of bodily fluid that is transferred, diverted, and/or sequestered prior to procuring the "sample" volume. In some embodiments, the terms "pre-sample," "first," and/or "initial" can refer to a predetermined, defined, desired, or given volume, portion, or amount of bodily fluid. For example, in some embodiments, a predetermined and/or desired pre-sample volume of bodily fluid can be about 0.1 milliliter (mL), about 0.2 mL, about 0.3 mL, about 0.4 mL, about 0.5 mL, about 1.0 mL, about 2.0 mL, about 3.0 mL, about 4.0 mL, about 5.0 mL, about 10.0 mL, about 20 mL, about 50 mL, and/or any volume or fraction of a volume therebetween. In other embodiments, the pre-sample volume can be greater than 50 mL or less than 0.1 mL. In some specific embodiments, a predetermined and/or desired pre-sample volume can be between about 0.1 mL and about 5.0 mL. In other embodiments, the pre-sample volume can be, for example, a drop of bodily fluid, a few drops of bodily fluid, a combined volume of any number of lumen that form, for example, a flow path (or portion thereof) from the bodily fluid source to an initial collection chamber, portion, reservoir, etc. (e.g., a sequestration chamber).

On the other hand, the terms "sample," "second," and/or "subsequent" when used in the context of a volume of bodily fluid can refer to a volume, portion, or amount of bodily fluid that is either a random volume or a predetermined or desired volume of bodily fluid collected after transferring, diverting, sequestering, and/or isolating the pre-sample volume of bodily fluid. For example, in some embodiments, a desired sample volume of bodily fluid can be about 10 mL to about 60 mL. In other embodiments, a desired sample volume of bodily fluid can be less than 10 mL or greater than 60 mL. In some embodiments, for example, a sample volume can be at least partially based on one or more tests, assays, analyses, and/or processes to be performed on the sample volume. In some embodiments, multiple sample volumes having a known, predetermined, and/or desired volume can be distributed from a fluid reservoir containing an amount of bodily fluid (e.g., an amount of bodily fluid that is greater than the known, predetermined, and/or desired volume of a single sample volume).

When describing a relationship between a predetermined volume of bodily fluid and a collected volume of bodily fluid it is to be understood that the values include a suitable tolerance such as those described above. For example, when stating that a collected volume of bodily fluid is substantially equal to a predetermined volume of bodily fluid, the collected volume and the predetermined volume are nominally equal within a suitable tolerance. In some instances, the tolerances can be determined by the intended use of the collected volume of bodily fluid. For example, in some instances, an assay of a blood culture can be about 99% accurate when the collected volume of blood is within 1.0% to 5.0% of the manufacturer's (or evidence-based best practices) recommended volume. By way of an example, a manufacturer's recommended volume for an assay of a bodily fluid can be 10 milliliters (mL) per sample collection bottle, with a total of four or six collection bottles used (i.e., an aggregate volume of 40 ml to 60 ml) plus or minus 5% for about 99% confidence. Thus, a collected volume of 10.5 mL would provide results with over about 99% confidence, while a collected volume of 11 mL would provide results with less than about 99% confidence. In other instances, a suitable tolerance can be 0.1%, 0.5%, 1.0%, 2.0%, 3.0%, 4.0%, 5.0%, 6.0%, 7.0%, 8.0%, 9.0%, 10.0%, or any fraction of a percent therebetween. In still other instances, a tolerance can be greater than 10.0%. Any of the embodiments described herein can include and/or can be used in conjunction with any suitable flow-metering mechanism and/or device that is configured to meter a flow and/or otherwise measure a volume of bodily fluid within a suitable tolerance. In some implementations, the flow-metering mechanism and/or device can be arranged such as to minimize or eliminate tolerance stacking that can result from a combination of inaccurate measurement(s), human error(s), and/or the like.

The embodiments described herein can be configured to selectively transfer bodily fluid to one or more fluid collection device(s). In some embodiments, a fluid collection device can include, but is not limited to, any suitable vessel, reservoir, bottle, adapter, dish, vial, microliter vial, nanoliter vial, container, microliter container, nanoliter container, syringe, device, diagnostic and/or testing machine, and/or the like. By way of specific example, in some instances, any of the embodiments and/or methods described herein can be used to transfer a sample volume into a sample reservoir such as any of those described in detail in U.S. Pat. No. 8,197,420 entitled, "Systems and Methods for Parenterally Procuring Bodily-Fluid Samples with Reduced Contamination," filed Dec. 13, 2007 ("the '420 Patent") and/or U.S. Patent Publication No. 2018/0140240 entitled, Systems and Methods for Sample Collection with Reduced Hemolysis," filed Nov. 20, 2017 ("the '240 publication"), the disclosure of each of which is incorporated herein by reference in its entirety. In other embodiments, a fluid collection device can be substantially similar to or the same as known sample containers such as, for example, a Vacutainer® (manufactured by Becton, Dickinson and Company ("BD")), a BacT/ALERT® SN or BacT/ALERT® FA (manufactured by Biomerieux, Inc.), and/or the like.

In some embodiments, a sample reservoir can be a sample or culture bottle such as, for example, an aerobic or an anaerobic culture bottle. In this manner, the culture bottle can receive a bodily fluid sample, which can then be tested (e.g., via in vitro diagnostic (IVD) tests, and/or any other suitable test) for the presence of, for example, Gram-Positive bacteria, Gram-Negative bacteria, yeast, fungi, and/or any other organism. In some instances, the culture bottle can receive a bodily fluid sample and the culture medium (disposed therein) can be tested for the presence of any suitable organism. If such a test of the culture medium yields a positive result, the culture medium can be subsequently tested using a PCR-based system to identify a specific organism. Moreover, as described in further detail herein, in some instances, diverting a pre-sample or initial volume of bodily fluid can reduce and/or substantially eliminate contaminants in the bodily fluid sample that may otherwise lead to inaccurate test results.

Any of the sample containers, reservoirs, bottles, dishes, vials, etc., described herein can be devoid of contents prior to receiving a sample volume of bodily fluid or can include, for example, any suitable additive, culture medium, substances, enzymes, oils, fluids, and/or the like. For example, in some embodiments, a sample reservoir can include an aerobic or anaerobic culture medium (e.g., a nutrient rich and/or environmentally controlled medium to promote growth, and/or other suitable medium(s)), which occupies at least a portion of the inner volume defined by the sample reservoir. In some embodiments, a sample reservoir can include, for example, any suitable additive or the like such as, heparin, citrate, ethylenediaminetetraacetic acid (EDTA), oxalate, SPS, and/or the like, which similarly occupies at least a portion of the inner volume defined by the sample reservoir. In other embodiments, a sample reservoir can be any suitable container used to collect a specimen.

While the term "culture medium" can be used to describe a substance configured to react with organisms in a bodily fluid (e.g., microorganisms such as bacteria) and the term "additive" can be used to describe a substance configured to react with portions of the bodily fluid (e.g., constituent cells of blood, serum, synovial fluid, etc.), it should be understood that a sample reservoir can include any suitable substance, liquid, solid, powder, lyophilized compound, gas, etc. Moreover, when referring to an "additive" within a sample reservoir, it should be understood that the additive could be a culture medium, such as an aerobic culture medium and/or an anaerobic culture medium contained in a culture bottle, an additive and/or any other suitable substance or combination of substances contained in a culture bottle and/or any other suitable reservoir such as those described above. That is to say, the embodiments described herein can be used with any suitable fluid reservoir or the like containing any suitable substance. Furthermore, any of the embodiments and/or methods described herein can be used to transfer a volume of bodily fluid to a reservoir (or the like) that does not contain a culture medium, additive, and/or any other substance prior to receiving a flow of bodily fluid.

While some of the embodiments are described herein as being used for procuring bodily fluid for one or more culture sample testing, it should be understood that the embodiments are not limited to such a use. Any of the embodiments and/or methods described herein can be used to transfer a flow of bodily fluid to any suitable device that is placed in fluid communication therewith. Thus, while specific examples are described herein, the devices, methods, and/or concepts are not intended to be limited to such specific examples. Moreover, a sample collected through the use of any of the devices described herein can be used in any suitable testing such as those described above.

Any of the embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-gly-colides (PLGA), polyanhydrides, polyorthoesters, polyetheresters, polycaprolactones, polyesteramides, poly (butyric acid), poly(valeric acid), polyurethanes, and/or blends and copolymers thereof. Examples of non-biodegrad-able polymers include nylons, polyesters, polycarbonates, polyacrylates, polymers of ethylene-vinyl acetates and other acyl substituted cellulose acetates, non-degradable polyure-thanes, polystyrenes, polyvinyl chloride, polyvinyl fluoride, poly(vinyl imidazole), chlorosulphonate polyolefins, poly-ethylene oxide, and/or blends and copolymers thereof.

The embodiments described herein and/or portions thereof can include components formed of one or more parts, features, structures, etc. When referring to such com-ponents it should be understood that the components can be formed by a singular part having any number of sections, regions, portions, and/or characteristics, or can be formed by multiple parts or features. For example, when referring to a structure such as a wall or chamber, the structure can be considered as a single structure with multiple portions, or multiple, distinct substructures or the like coupled to form the structure. Thus, a monolithically constructed structure can include, for example, a set of substructures. Such a set of substructures may include multiple portions that are either continuous or discontinuous from each other. A set of substructures can also be fabricated from multiple items or components that are produced separately and are later joined together (e.g., via a weld, an adhesive, a snap, and/or any suitable method).

Figure 1B:
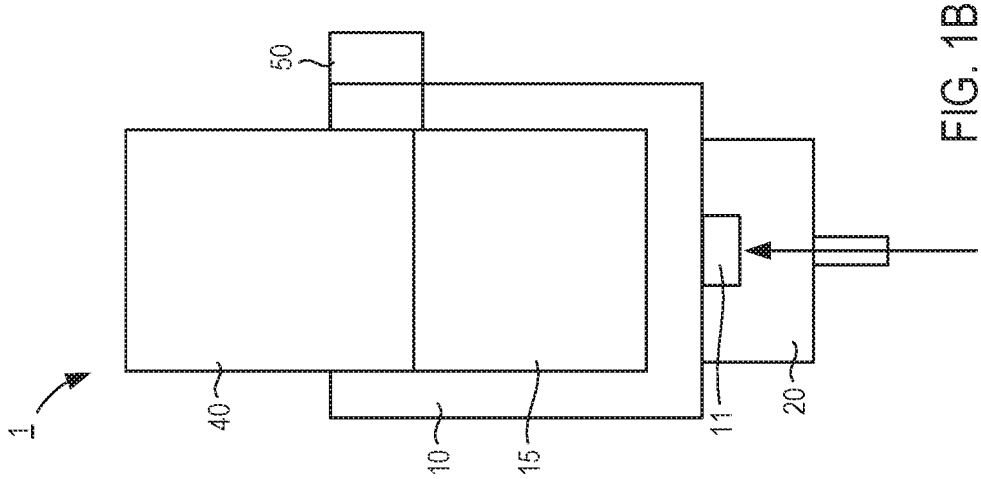
Figure 1A:
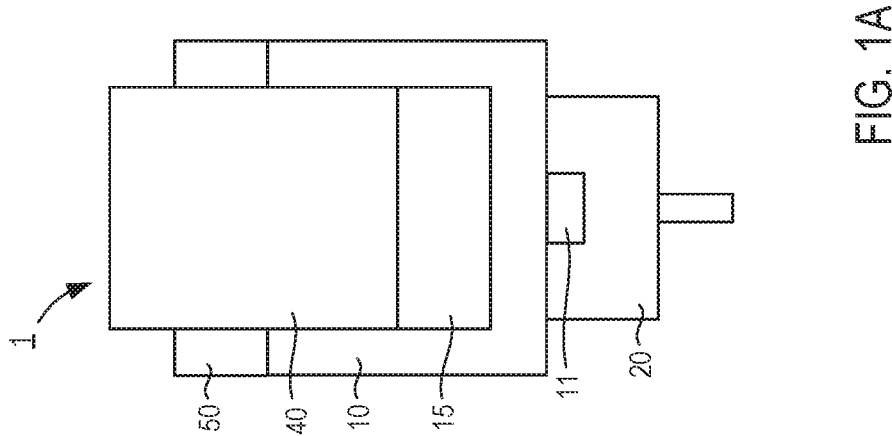
Figure 2:
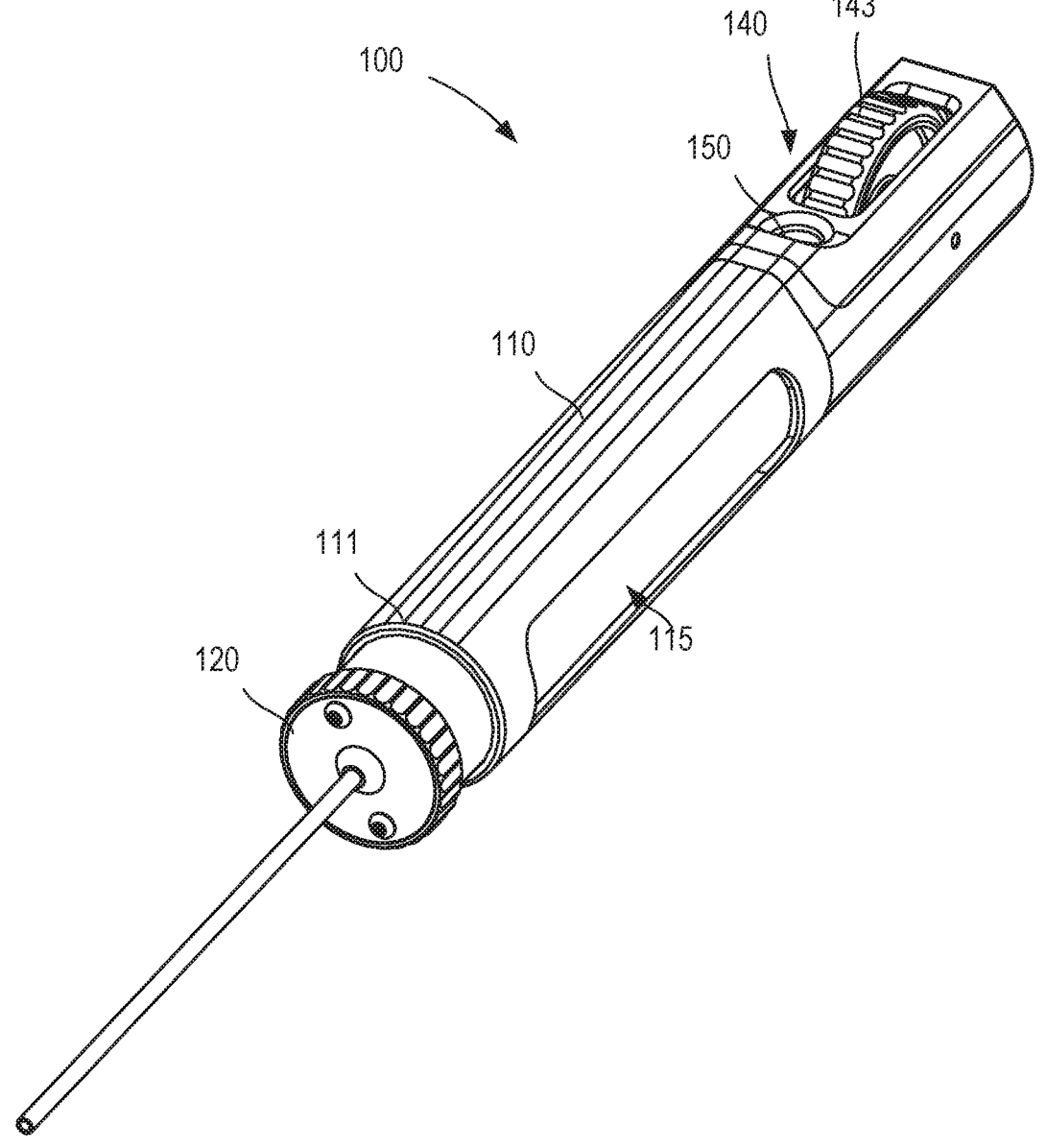
FIG. 2 is a perspective view of a bodily fluid collection and distribution device according to an embodiment.
Figure 3:
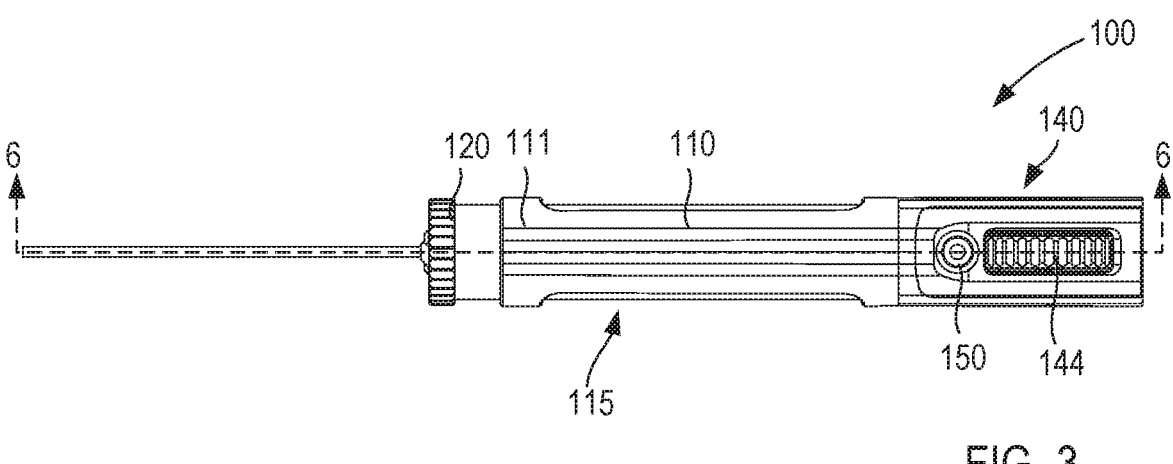
FIGS. 3-5 are a top view, a left side view, and a rear view of the bodily fluid collection and distribution device of FIG. 2.
Figure 4:
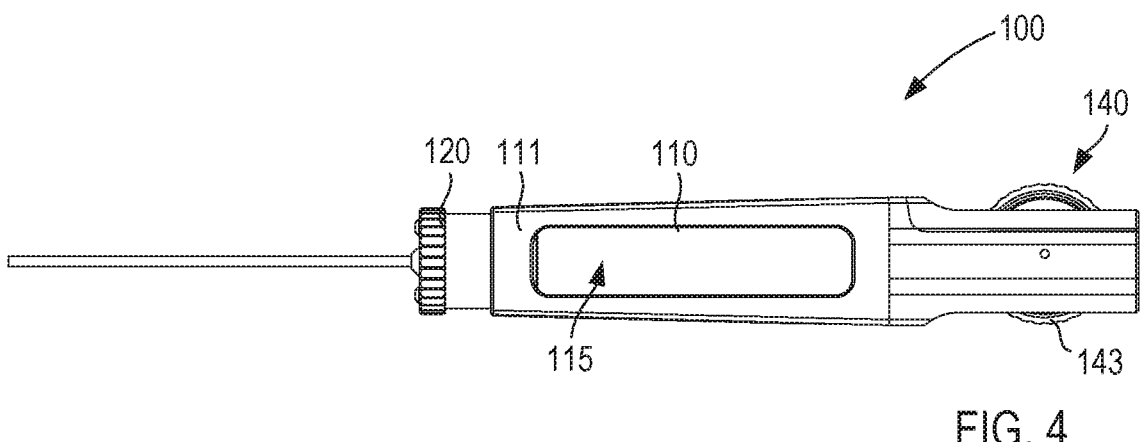

FIGS. 1A-1C are schematic illustrations of a bodily fluid collection and distribution device 1 according to an embodi-ment. The bodily fluid collection and distribution device 1 (also referred to herein as "device") can be any suitable shape size, and/or configuration. In some embodiments, the device 1 can have a size and/or shape that enhances and/or facilitates ergonomics and/or ease of use. In some embodi-ments, the device 1 and/or at least a portion thereof can be similar in form and/or function to a syringe and/or similar device configured to receive and at least temporarily contain a fluid therein. In some implementations, the device 1 can be manipulated to draw a volume of bodily fluid from a bodily fluid source (e.g., a patient) into a portion of the device 1 at a flow rate below a threshold flow rate. Although not shown in FIGS. 1A-1C, in some embodiments, the device 1 can include, can couple to, and/or can integrate with a device that can divert and at least temporarily sequester an initial volume of bodily fluid withdrawn from a bodily fluid source. In some instances, diverting and sequestering the initial volume of bodily fluid can reduce and/or substantially eliminate the presence of contaminants in a subsequent volume of bodily fluid drawn into a portion of the device 1, as described in detail in the '420 Patent.

As shown in FIGS. 1A-1C, the device 1 includes a housing 10, a fluid reservoir 15, an inlet adapter 20, an actuator 40, and a volume indicator 50. The housing 10 can be any suitable shape, size, and/or configuration. For example, in some embodiments, the housing 10 can have an elongate and/or substantially cylindrical shape similar to some known syringes. In other embodiments, the housing 10 can have any other suitable shape. In some embodiments, a size of the housing 10 can be at least partially based on a desired volume or amount of fluid to be at least temporarily contained therein. For example, in some embodiments, the housing 10 can contain and/or at least partially form the fluid reservoir 15 and a size and/or volume of the housing 10 can be based at least in part on a desired volume of fluid that can be transferred into and/or out of the fluid reservoir 15.

The housing 10 is configured to contain, house, and/or form at least a portion of the fluid reservoir 15, the actuator 40, and the volume indicator 50. The housing 10 includes a port 11 that is in fluid communication with the fluid reservoir 15 and that is physically and fluidically coupleable, at least temporarily, to the inlet adapter 20 (see e.g., FIGS. 1A and 1B). In some instances, the inlet adapter 20 can be removed or decoupled from the port 11, which in turn, can be fluidically coupled to one or more external collection res-ervoirs, sample bottles, culture bottles, etc. (see e.g., FIG. 1C).

The fluid reservoir 15 is disposed in and/or is formed by the housing 10. For example, in some embodiments, the fluid reservoir 15 can be formed independent of the housing 10 and inserted or disposed within a portion of the housing 10 during manufacturing. In other embodiments, at least a portion of the housing 10 and at least a portion of the fluid reservoir 15 can be monolithically and/or integrally formed. The fluid reservoir 15 can have and/or can define any suitable volume. For example, in some embodiments, the fluid reservoir 15 can have a volume between about 5.0 mL and about 60.0 mL, between about 10.0 mL and about 50.0 mL, between about 20.0 mL and about 40.0 mL, or about 30.0 mL. In some embodiments, the fluid reservoir 15 can have a volume of about 20.0 mL, about 25.0 mL, or about 30 mL. In other embodiments, the fluid reservoir 15 can have a volume that is less than about 5.0 mL or greater than about 60.0 mL. The fluid reservoir 15 is in fluid communi-cation with the port 11 of the housing 10 and, as such, can receive or convey a flow of fluid via the port 11, as described in further detail herein. Although not shown in FIG. 1A-1C, in some embodiments, the device 1 can include a pre-sample reservoir that is fluidically isolated from the fluid reservoir 15 and that is configured to receive an initial volume of bodily fluid transferred into the housing 10.

The actuator 40 can be any suitable shape, size, and/or configuration. For example, in some embodiments, the actuator 40 can include a syringe-like plunger and one or more portions configured to be engaged by a user to move the syringe-like plunger within the housing 10. In some embodiments, the syringe-like plunger (referred to herein for simplicity as "plunger") can include a seal that forms a fluid tight seal with an inner surface of the fluid reservoir 15 (or an inner surface of the housing 10 defining a portion of the fluid reservoir 15). As such, the plunger of the actuator 40 can form and/or define at least a portion of the fluid reservoir 15. For example, the fluid reservoir 15 can be and/or can have a volume that is collectively defined by and/or between the inner surface of the housing 10, the port 11, and the plunger of the actuator 40.

The actuator 40 can be manipulated to move the plunger within the housing 10 to increase or decrease a volume of the fluid reservoir 15. In some instances, increasing the volume of the fluid reservoir 15 can result in a decrease in pressure (e.g., a negative pressure, vacuum, suction force, etc.) within the fluid reservoir 15 that is operable in drawing fluid (e.g., bodily fluid) through the port 11 and into the fluid reservoir 15. Conversely, decreasing the volume of the fluid reservoir 15 can result in an increase in pressure within the fluid reservoir 15 that is operable in expelling fluid out of the fluid reservoir 15 through the port 11, as described in further detail herein.

In some embodiments, the arrangement of the actuator 40 can be such that the actuator 40 and/or a portion thereof is configured to control and/or modulate a rate of change in the volume of the fluid reservoir 15. For example, in some embodiments, a first portion of the actuator 40 can be engaged and/or manipulated by a user to transition and/or move a second portion of the actuator 40 that includes, for example, the plunger. In some implementations, the first portion of the actuator 40 (e.g., an engagement portion or the like) can be directly or indirectly coupled to the second portion of the actuator 40 (e.g., at least the plunger of the actuator 40) and can be configured to use and/or transfer at least a portion of a force exerted by a user of the first portion of the actuator 40 into a known, predetermined, and/or modulated force to transition and/or move the second portion of the actuator 40. Said another way, in some implementations, the actuator 40 and/or one or more portions thereof can be configured to control and/or modulate a rate of change in volume of the fluid reservoir 15, which in turn, can control and/or modulate a flow rate of fluid into and/or out of the fluid reservoir 15. In some implementations, such control and/or modulation can result in a user having an increased amount of control of a flow rate of fluid into and/or out of the fluid reservoir 15, which can allow a user to more accurately control a volume of fluid that is transferred into and/or out of the fluid reservoir 15, as described in further detail herein.

For example, in some embodiments, the first portion of the actuator 40 can be one or more wheels, dials, pinions, levers, pneumatic or hydraulic actuators, rods, etc., that can be directly or indirectly coupled to the second portion of the actuator 40 (e.g., the plunger 40). In some embodiments, the first portion of the actuator 40 can be coupled to the second portion of the actuator 40 via one or more racks, tracks, channels, flow paths, energy storage members and/or bias members (e.g., one or more springs), kinematic linkages, and/or the like. In some implementations, the direct or indirect coupling between the first portion of the actuator 40 (e.g., an engagement portion or member) and the second portion of the actuator 40 (e.g., the plunger) can be selected and/or designed to modulate a transfer of energy and/or force therebetween. For example, in some implementations, the first portion of the actuator 40 can be a wheel that is indirectly coupled to the second portion of the actuator 40 via one or more racks and pinions. In such implementations, a force exerted on the second portion of the actuator 40 can be modulated, tuned, and/or controlled by, for example, increasing or decreasing a gear ratio between the wheel, the pinion, and/or the rack.

In other embodiments, a transfer of energy and/or force can be modulated and/or controlled via any suitable mechanism such as, for example, increasing and/or decreasing a size and/or shape of a track, channel, flow path, etc.; increasing or decreasing a spring constant and/or strength of one or more components; increasing or decreasing a size and/or number of components in a kinematic linkage; increasing or decreasing a flow rate of a gas or fluid; and/or via any other suitable mechanism or method, such as any of those described herein. While specific examples and/or methods of controlling and/or modulating a rate of change in volume of the fluid reservoir 15 and/or a flow rate of fluid into and/or out of the fluid reservoir 15, in other embodiments, a transfer and distribution device can control and/or modulate the rate of change in volume of a fluid reservoir include any suitable manner and is not intended to be limited to the specific examples and/or methods described herein.

The volume indicator 50 can be any suitable shape, size, and/or configuration. For example, in some embodiments, the volume indicator 50 is a button, knob, dial, lever, pointer, and/or any other suitable indicator. The volume indicator 50 can be configured to transition or to be transitioned from a first state to a second state to provide an indication associated with a volume of fluid disposed in the fluid reservoir 15. For example, the volume indicator 50 can be transitioned (e.g., automatically) from the first state to the second state in response to a known, desired, and/or predetermined volume of bodily fluid being disposed in the fluid reservoir 15. In some embodiments, the known, desired, and/or predetermined volume of bodily fluid can be based at least in part on a volume of bodily fluid (e.g., blood) suitable for one or more tests or the like configured to be performed on or using the bodily fluid such as, for example, blood culture testing and/or the like. In some embodiments, the known, desired, and/or predetermined volume can be, for example, 1.0 mL, 2.0 mL, 3.0 mL, 4.0 mL, 5.0 mL, 6.0 mL, 7.0 mL, 8.0 mL, 9.0 mL, 10.0 mL, 15.0 mL, 20.0 mL, or any suitable volume or fraction of a volume therebetween. In other embodiments, the known, desired, and/or predetermined volume can be less than 1.0 mL or greater than 20.0 mL.

As an example, a known, desired, and/or predetermined volume can be 10.0 mL. As such, the volume indicator 50 can transition and/or can be transitioned from the first state to the second state in response to 10.0 mL of bodily fluid being transferred into and/or disposed in the fluid reservoir 15. In some embodiments, the volume indicator 50 can be transitioned from the first state in which the volume indicator 50 (e.g., a button or the like) is depressed or substantially disposed in the housing 10 to the second state in which the volume indicator 50 is raised relative to the housing 10 (e.g., at least a portion of the button extends out of or from the housing 10). When in the second state, the volume indicator 50 can provide an indication to the user that 10.0 mL has been disposed in the fluid reservoir 10. In response, the user can decide whether to continue to draw additional amounts of bodily fluid into the fluid reservoir 15 (e.g., by continuing to engage the actuator 40) or to stop or end the procurement process.

In some embodiments, the volume indicator 50 can also be configured to at least temporarily place the device 1 and/or the actuator 40 in a state or configuration that limits and/or substantially prevents movement of at least a portion of the actuator 40 (e.g., movement of the plunger within the housing 10). For example, as described above, the volume indicator 50 can be a button (or the like) that can be moved or transitioned to the second state such that the button extends out of or from a surface of the housing 10. In some embodiments, the volume indicator 50 can selectively engage, for example, any suitable portion of the actuator 40 to limit and/or substantially prevent movement of the plunger while the volume indicator 50 is in the second state. As such, the user can manipulate the volume indicator 50 and/or can exert a force on the volume indicator 50 that is operable to transition the volume indicator 50 away from the second state. In some embodiments, for example, the volume indicator 50 can be transitioned toward and/or returned to the first state. In other embodiments, the volume indicator 50 can be transitioned toward and/or to a third state, different from the first state and the second state.

The inlet adapter 20 is configured to at least temporarily couple to the port 11 of the housing 10. The inlet adapter 20 can be any suitable shape, size, and/or configuration. The inlet adapter 20 can include a lumen-containing device configured to be in fluid communication with a bodily fluid source. For example, in some embodiments, the inlet adapter 20 can include a needle or catheter configured to be inserted into a vein or artery of a patient. In other embodiments, the inlet adapter 20 can include a catheter and/or other conduit configured to establish fluid communication between the inlet adapter 20 and a bodily fluid source and/or an intermediate device (e.g., a diversion device, a placed intravenous catheter, and/or any other suitable device).

As shown in FIGS. 1A and 1B, the inlet adapter 20 is fluidically coupled to the port 11 when the inlet adapter 20 is coupled to the housing 10. In some embodiments, the port 11 of the housing 10 can include a needle or other puncture member configured to be advanced through a pierceable, sealable, and/or frangible portion of the inlet adapter 20. For example, the inlet adapter 20 can include a self-sealing port or the like that is pierced by the needle or puncture member of the port 11 when the inlet adapter 20 is coupled thereto and that returns to a sealed state or the like when the inlet adapter 20 is removed from the housing 10. In such embodiments, the needle and/or puncture member can place an internal portion of the inlet adapter 20 in fluid communication with the fluid reservoir 15, thereby allowing fluid (e.g., bodily fluid) to be transferred from the inlet adapter 20 into the fluid reservoir 15. In other embodiments, the inlet adapter 20 and port 11 can include and/or can collectively form a luer-style connection and/or any other suitable physical and/or fluidic interface.

As shown in FIG. 1C, in some instances, the inlet adapter 20 can be decoupled and/or otherwise removed from the housing 10 after a desired volume of fluid has been transferred into the fluid reservoir 15. In some embodiments, decoupling of the inlet adapter 20 from the port 11 can be such that the needle and/or puncture member coupled to the port 11 is exposed, which in turn, can allow the port 11 to be physically and/or fluidically coupled to any suitable external device and/or reservoir. For example, in some embodiments, the port 11 can be configured to physically and/or fluidically couple to a culture bottle or other sample reservoir. In other embodiments, the port 11 can be coupled to and/or can include any suitable transfer adapter such as, for example, those described in U.S. Pat. No. 10,123,783 entitled, "Apparatus and Methods for Disinfection of a Specimen Container," filed Mar. 3, 2015 (referred to herein as "the '783 patent"), the disclosure of which is incorporated herein by reference in its entirety.

In some embodiments, the inlet adapter 20 can be configured to collect, divert, and/or sequester an initial volume of bodily fluid received from a bodily fluid source (e.g., a patient). For example, in some embodiments, the inlet adapter 20 can have a first state or configuration in which the initial volume of bodily fluid is transferred into a first portion of the inlet adapter 20 (e.g., via a first flow path or the like) and can be transitioned from the first state or configuration to a second state and/or configuration in which (1) the initial volume of bodily fluid is sequestered by or in the first portion of the inlet adapter 20 and (2) a subsequent volume of bodily fluid can be transferred, via a second flow path or the like, through the inlet adapter 20 and into the fluid reservoir 15. As such, the subsequent volume of bodily fluid can be substantially free from contaminants or the like that may otherwise be contained in the initial volume of bodily fluid. In other embodiments, the inlet adapter 20 can be configured to couple to a diversion device or the like configured to divert and sequester the initial volume of bodily fluid. In still other embodiments, the diversion device or the like can be integrated and/or included in the device 1 (e.g., at least partially disposed in the housing 10).

Collection, diversion, and/or sequestration of the initial volume of bodily fluid can be performed in any suitable manner by any suitable device or combination of devices. For example, in some embodiments, collection, diversion, and/or sequestration of the initial volume of bodily fluid can be performed using any of the devices (or portions thereof), concepts, and/or methods described in the '420 patent, the '240 publication, and/or the '783 patent; U.S. Patent Publication No. 2015/0342510 entitled, "Sterile Bodily-Fluid Collection Device and Methods," filed Jun. 2, 2015 ("the '510 publication"); U.S. Pat. No. 8,535,241 entitled, "Fluid Diversion Mechanism for Bodily-Fluid Sampling," filed Oct. 12, 2012 ("the '214 patent"); U.S. Pat. No. 9,060,724 entitled, "Fluid Diversion Mechanism for Bodily-Fluid Sampling," filed May 29, 2013 ("the '724 patent"); U.S. Pat. No. 9,155,495 entitled, "Syringe-Based Fluid Diversion Mechanism for Bodily-Fluid Sampling," filed Dec. 2, 2013 ("the '495 patent"); U.S. Patent Publication No. 2016/0361006 entitled, "Devices and Methods for Syringe-Based Fluid Transfer for Bodily-Fluid Sampling," filed Jun. 13, 2016 ("the '006 publication"); U.S. Pat. No. 9,950,084 entitled, "Apparatus and Methods for Maintaining Sterility of a Specimen Container," filed Sep. 6, 2016 ("the '084 patent"); U.S. Patent Publication No. 2018/0353117 entitled, "Fluid Control Devices and Methods of Using the Same," filed Jun. 11, 2018 ("the '117 publication"); U.S. Patent Publication No. 2019/0076074 entitled, "Fluid Control Devices and Methods of Using the Same," filed Sep. 12, 2018 ("the '074 publication"); and/or U.S. Patent Publication No. 2019/0175087 entitled, "Fluid Control Devices and Methods of Using the Same," filed Dec. 7, 2018 ("the '087 publication"), the disclosure of each of which is incorporated herein by reference in its entirety.

In some instances, a user can use the device 1 to obtain an amount of bodily fluid that is substantially free from contaminants and then can use device 1 to deliver at least one desired and accurate (e.g., proper, appropriate, and/or recommended) volume of the procured bodily fluid to a corresponding sample reservoir such as, for example, an aerobic or an anaerobic culture bottle. For example, as described above, a user can establish fluid communication between the fluid reservoir 15 and a bodily fluid source via the inlet adapter 20 and the port 11 of the housing 10. In some instances, the user can engage the device 1, the inlet adapter 20, and/or a device coupled to the inlet adapter 20 to divert and sequester an initial volume of bodily fluid. In other instances, a user can divert and sequester the initial volume of bodily fluid via a connected or separate diversion device. In still other instances, the user need not divert an initial volume of bodily fluid.

After establishing fluid communication with the bodily fluid source, the user can engage and/or manipulate the actuator 40 to transition the actuator 40 from a first state to or toward a second state. For example, the actuator 40 can be engaged and/or manipulated to move the plunger of the actuator 40 from a first position in which the fluid reservoir 15 has a first volume (FIG. 1A), to (or toward) a second position in which the fluid reservoir 15 has a second volume greater than the first volume (FIG. 1B). The movement of the plunger from the first position to the second position can result in an increase in a volume of the fluid reservoir 15, which in turn, can generate a negative pressure differential and/or a suction force operable in drawing a volume of bodily fluid into the fluid reservoir 15. In some instances, diverting the initial volume of bodily fluid can be such that the volume of bodily fluid transferred into the fluid reservoir 15 is substantially free of contamination that may result in false results during testing.

After drawing a predetermined volume of bodily fluid into the fluid reservoir 15, the volume indicator 50 can transition (e.g., automatically) from its first state (FIG. 1A) to its second state (FIG. 1B) to provide the user with an indication that the predetermined volume is contained in the fluid reservoir 15. In some instances, the predetermined volume can be based on a desired volume configured to be transferred into an aerobic culture bottle (e.g., 10.0 mL of bodily fluid). In other embodiments, the predetermined volume can be any suitable volume. In some instances, the user can stop collecting bodily fluid after the predetermined volume is disposed in the fluid reservoir 15. In other embodiments, the user can continue to engage and/or manipulate the actuator 40 to draw additional amounts of bodily fluid into the fluid reservoir 15. For example, in some embodiments, the user can engage and/or transition the volume indicator 50 to move the volume indicator 50 away from its second state, thereby enabling additional amounts of bodily fluid to be transferred into the fluid reservoir 15.

In some implementations, the arrangement of the actuator 40 can be configured to control, meter, and/or modulate a rate at which bodily fluid is transferred into the fluid reservoir 15 (e.g., controlling, limiting, and/or modulating a rate at which the plunger can be moved within or relative to the fluid reservoir 15). As such, a negative pressure differential and/or suction force within the fluid reservoir 15 can be modulated and/or limited. In addition, limiting a rate of fluid transfer into the fluid reservoir 15 can enhance and/or facilitate the collection of a proper, appropriate, recommended, desired, and/or otherwise accurate volume of bodily fluid.

As shown in FIG. 1C, after transferring the desired amount of bodily fluid, for example, the user can remove the inlet adapter 20 from the port 11. The inlet adapter 20 and/or a volume of bodily fluid disposed therein can then be discarded and/or used for any other suitable process and/or purpose. In some instances, the user can then couple the port 11 to any suitable collection or sample reservoir such as, for example, a culture bottle (and/or any collection device described herein). Accordingly, the port 11 of the housing 10 can be used to transfer fluid into the fluid reservoir 15 (e.g., acting as an inlet port) and to transfer fluid out of the fluid reservoir 15 (e.g., acting as an outlet port).

In some instances, for example, it may be desirable to transfer a predetermined and/or desired volume of bodily fluid into an anaerobic culture bottle for use in the testing of samples incubated in an anaerobic culture medium, which can be relatively sensitive to false negatives as a result of insufficient sample volume. Moreover, in some embodiments, the volume indicator 50 can be configured to transition to and/or can automatically be placed in its second state in response to the predetermined and/or desired volume of bodily fluid being transferred into the collection or sample reservoir (e.g., the anaerobic culture bottle). In some embodiments, the predetermined and/or desired volume of bodily fluid can be about 10.0 mL. In some instances, additional amounts or volumes of the bodily fluid contained in the fluid reservoir 15 can be distributed into one or more additional collection and/or sample reservoirs based at least in part on a desired and/or predetermined volume of bodily fluid intended to be conveyed into that specific type of collection and/or sample reservoir (e.g., per a manufacturer's indication, instruction, and/or recommendation). Thus, the device 1 can be configured to obtain bodily fluid that is substantially free from contaminants and configured to distribute, into one or more collection or sample reservoirs and in desired volumes, the obtained bodily fluid.

FIGS. 2-8 illustrate a bodily fluid collection and distribution device 100 according to an embodiment. The bodily fluid collection and distribution device 100 (also referred to herein as "device") can be any suitable shape size, and/or configuration. In some embodiments, the device 100 can have a size and/or shape that enhances and/or facilitates ergonomics and/or ease of use. In some embodiments, the device 100 and/or at least a portion thereof can be similar in form and/or function to a syringe and/or similar device configured to receive and at least temporarily contain a fluid therein.

As described in further detail herein, the device 100 can be manipulated to draw a volume of bodily fluid into a portion of the device 100 at a flow rate below a threshold flow rate. Although not shown in FIGS. 2-8, the device 100 can include a portion and/or can be coupled to a device that is configured to divert and at least temporarily sequester an initial volume of bodily fluid withdrawn from a bodily fluid source (e.g., a patient). As described herein, diverting and sequestering the initial volume of bodily fluid can reduce and/or substantially eliminate the presence of contaminants in a subsequent volume of bodily fluid drawn into a portion of the device 100.

In some embodiments, the device 100 can be configured to provide one or more indications to a user regarding a volume or an amount of bodily fluid that has been transferred into the portion of the device 100. In some embodiments, after a known, predetermined, and/or desired volume of bodily fluid has been drawn into the portion of the device 100, the device 100 and/or a portion thereof can be configured to pause, inhibit, limit, and/or substantially prevent further use of the device 100 until a user provides an input that enables further use of the device 100. In some embodiments, the device 100 can be configured to couple to one or more sample reservoirs, bottles, containers, etc. after a volume of bodily fluid is drawn into the portion of the device 100. In such embodiments, the device 100 can be configured to distribute at least one portion of the volume of bodily fluid having a known, predetermined, and/or desired volume into at least one sample reservoir, bottle, and/or container, as described in further detail herein.

As shown in FIGS. 2-5, the device 100 includes a housing 110, a fluid reservoir 115, an inlet adapter 120, an actuator 140, and a volume indicator 150. The housing 110 can be any suitable shape, size, and/or configuration. For example, in some embodiments, the housing 110 can have an elongate and/or substantially cylindrical shape. In some embodiments, a size of the housing 110 can be at least partially based on a desired volume or amount of fluid to be at least temporarily contained therein. The housing 110 is configured to contain, house, and/or form at least a portion of the fluid reservoir 115, actuator 140, and volume indicator 150. The housing 110 includes a port 111 in fluid communication with the fluid reservoir 115 and configured to be physically and fluidically coupled, at least temporarily, to the inlet adapter 120 (see e.g., FIGS. 6 and 7). In some instances, the inlet adapter 120 can be removed or decoupled from the port 111, which in turn, can be physically and fluidically coupled to one or more collection reservoirs, sample bottles, culture bottles, etc., as described in further detail herein.

Figures 6, 7:
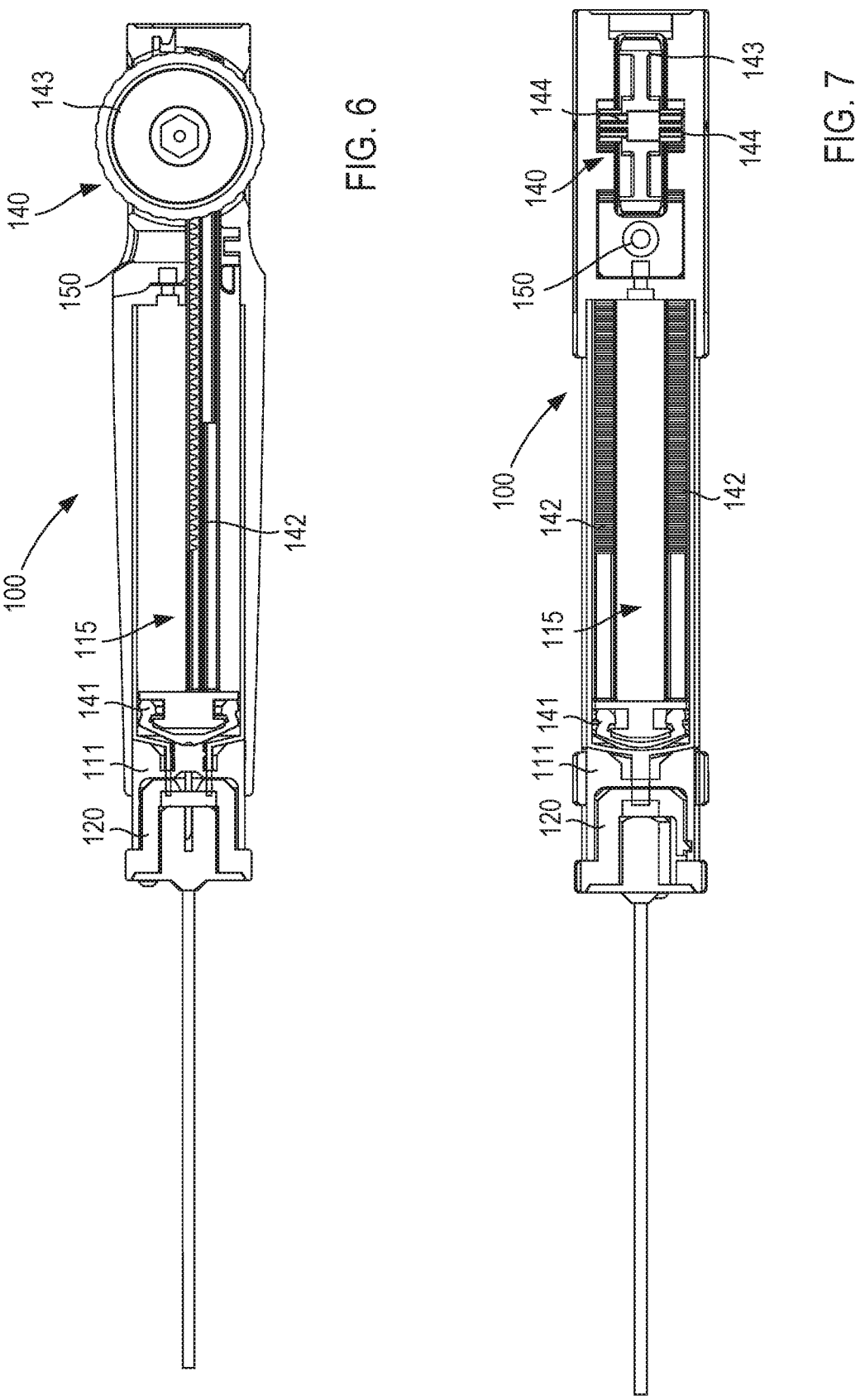
FIGS. 6 and 7 are each a cross-sectional view of the bodily fluid collection and distribution device of FIG. 2, taken along the line 6-6 in FIG. 3 and the line 7-7 in FIG. 5, respectively.

The fluid reservoir 115 is disposed in and/or is formed by the housing 110. For example, in some embodiments, the fluid reservoir 115 can be formed independent of the housing 110 and inserted or disposed within a portion of the housing 110 during manufacturing. In other embodiments, at least a portion of the housing 110 and at least a portion of the fluid reservoir 115 can be monolithically and/or integrally formed. In some embodiments, the housing 110 can form and/or can define the fluid reservoir 115. The fluid reservoir 115 can have and/or can define any suitable volume. For example, in some embodiments, the fluid reservoir 115 can have a volume between about 5.0 mL and about 60.0 mL, between about 10.0 mL and about 50.0 mL, or between about 20.0 mL and about 40.0 mL. In some embodiments, the fluid reservoir 115 can have a volume of about 20.0 mL. In other embodiments, the fluid reservoir 115 can have a volume that is less than about 5.0 mL or greater than about 60.0 mL. As shown in FIGS. 6 and 7, the fluid reservoir 115 is in fluid communication with the port 111 of the housing 110 and, as such, can receive or convey a flow of fluid via the port 111, as described in further detail herein.

Figure 5:
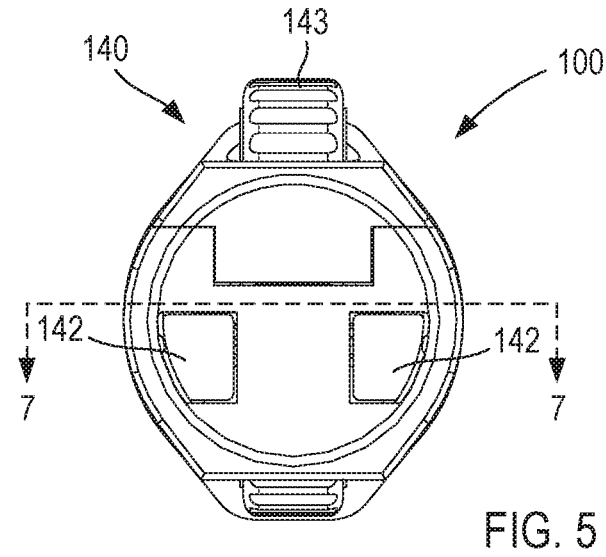

The actuator 140 can be any suitable shape, size, and/or configuration. For example, as shown in FIGS. 5-7, the actuator 140 includes a plunger 141, one or more racks 142, a wheel 143, and one or more pinions 144. The plunger 141 is movably disposed in fluid reservoir 115. In some embodiments, the plunger 141 can include a seal that forms a fluid tight seal with an inner surface of the fluid reservoir 115 (or housing 110) and that is configured to form at least a portion of the fluid reservoir 115. For example, the fluid reservoir 115 can be and/or can have a volume that is collectively defined by and/or between the inner surface, the seal of the plunger 141, and the port 111. In some instances, the actuator 140 can be manipulated to move the plunger 141 within the fluid reservoir 115, which in turn, can increase or decrease a volume of the fluid reservoir 115.

As shown in FIGS. 6 and 7, the one or more racks 142 are included in, formed by, and/or coupled to the plunger 141. In the embodiment shown in FIGS. 2-8, the actuator 140 includes a set of two racks 142. In other embodiments, an actuator 140 can include any number of racks. The racks 142 include and/or form a number of teeth, protrusions, ribs, etc. that extend along at least a portion of the racks 142. As shown in FIG. 5, a portion of the racks 142 can be disposed in and/or can extend through one or more openings defined by a rear surface of the housing 110. In some embodiments, such an arrangement can allow the racks 142—and there-fore, the plunger 141—to move relative to the housing 110, as described in further detail herein. While shown as includ-ing racks 142, in other embodiments, an actuator can include any suitable feature, member, and/or device operable to move the plunger 141 relative to the housing 110.

The wheel 143 of the actuator 140 is rotatably coupled to the housing 110 and is fixedly coupled to the one or more pinions 144, as shown in FIG. 6. The wheel 143 can be any suitable shape, size, and/or configuration. In some embodi-ments, the wheel 143 can be manipulated by a user (e.g., by a user's thumb) to rotate relative to the housing 140. The wheel 143 can have and/or can include any surface feature, contour, grip, and/or the like configured to facilitate and/or enhance contact between the user (e.g., the user's thumb) and the wheel 143.

The one or more pinions 144 are fixedly coupled to the wheel 143 and are in contact with and/or configured to rotate along the one or more racks 142. More specifically, the pinion(s) 144 can include a set of teeth, protrusions, ribs, gears, and/or the like that correspond with and/or that are configured to mesh with the teeth, protrusions, ribs, etc. of the rack(s) 142. In other words, the actuator 140 and/or at least a portion thereof forms and/or has a rack and pinion arrangement and/or configuration. The pinions 144 can have any suitable size and/or diameter to achieve and/or result in a desired ratio (e.g., gear ratio) with or relative to the wheel 143. That is to say, the wheel 143 and the pinion(s) 144 can have and/or can define any suitable gear ratio such that an amount of rotation of the wheel 143 (e.g., produced by a user manipulating the wheel) results in a known, desired, and/or predetermined amount of rotation of the pinion(s) 144. In some embodiments, for example, the wheel 143 can have a diameter of about 34 millimeters (mm) (about 1.34 inches (in.)) and the pinion(s) 144 can have a diameter of about 6.5 mm (about 0.26 in.). In some embodiments, the pinion(s) can have, for example, eight (8) teeth. In other embodi-ments, the pinion(s) can have fewer than eight teeth or more than eight teeth. In some embodiments, the relationship between the rack(s) 142, the wheel 143, and the pinion(s) 144 can at least partially control an effective pressure (negative pressure) generated by the device 100, a sensitivity of the wheel 143, an amount of tactile feedback associated with actuating the wheel 143, and/or the like. Moreover, the pinions 144 can have any suitable orientation relative to the racks 142, which in turn, can control a resulting direction associated with movement of the plunger 141 for a given direction associated with rotating the wheel 143.

The wheel 143 and the pinion(s) 144 are coupled to the housing 110 and allowed to rotate relative to the housing 110 without substantially changing a translational position rela-tive to the housing 110. In other words, the wheel 143 and the pinion(s) 144 are configured to rotate about an axis having a substantially fixed position relative to the housing 110. With the pinion(s) 144 being in contact with and/or meshed with the rack(s) 142, rotation of the wheel results in the pinion(s) 142 being advanced along the teeth or protru-sions of the rack(s) 142. Said another way, rotation of the wheel 143 results in rotation of the pinion(s) 143 at a known, predetermined, and/or anticipated rotational velocity, which in turn, results in the plunger 141 being translated within the housing 110 and/or fluid reservoir 115 with a known, pre-determined, and/or anticipated translational velocity. Accordingly, the device 100 can be similar in at least function to a syringe but can be configured to modulate a rate at which fluid is drawn into the fluid reservoir 115 and/or configured to provide an indication of and/or control of an amount or volume of bodily fluid contained in the fluid reservoir 115, as described in further detail herein.

The volume indicator 150 can be any suitable shape, size, and/or configuration. For example, in some embodiments, the volume indicator 150 is a button, knob, dial, lever, pointer, and/or any other suitable indicator. The volume indicator 150 can be configured to transition or to be transitioned from a first state to a second state to provide an indication associated with a volume of fluid disposed in the fluid reservoir 115. For example, the volume indicator 150 can be transitioned (e.g., automatically) from the first state to the second state in response to a known, desired, and/or predetermined volume of bodily fluid being disposed in the fluid reservoir 115. In some embodiments, the known, desired, and/or predetermined volume can be, for example, any of those described above with reference to the device 1 shown in FIGS. 1A-1C. By way of example, the volume indicator 150 can be transitioned from the first state in which the volume indicator 150 (e.g., a button or the like not shown in FIGS. 2-8) is depressed or substantially disposed in the housing 110 to the second state in which the volume indicator 150 is raised relative to the housing 110 (e.g., at least a portion of the button extends out of or from the housing 110). As such, the volume indicator 150 can provide an indication to the user that 10.0 mL has been disposed in the fluid reservoir 110. In response, the user can decide whether to continue to draw additional amounts of bodily fluid into the fluid reservoir 115 (e.g., by continuing to engage the actuator 140) or to stop or end the procurement process.

In some embodiments, the volume indicator 150 can also be configured to at least temporarily place the device 100 and/or the actuator 140 in a state or configuration that limits and/or substantially prevents movement of the plunger 141 within the fluid reservoir 110. For example, as described above, the volume indicator 150 can be a button (or the like) that can be moved or transitioned to the second state such that the button is raised relative to the housing 110 (e.g., at least a portion of the button extends out of or from a surface of the housing 110). In some embodiments, the volume indicator 150 can selectively engage, for example, the rack(s) 142 and/or any other suitable portion of the actuator 140 to limit and/or substantially prevent movement of the plunger 141 while the volume indicator 150 is in the second state. As such, the user can manipulate the volume indicator 150 and/or can exert a force on the volume indicator 150 that is operable to transition the volume indicator 150 away from the second state. In some embodiments, for example, the volume indicator 150 can be transitioned toward and/or returned to the first state. In other embodiments, the volume indicator 150 can be transitioned toward and/or to a third state, different from the first state and the second state.

Figure 8:
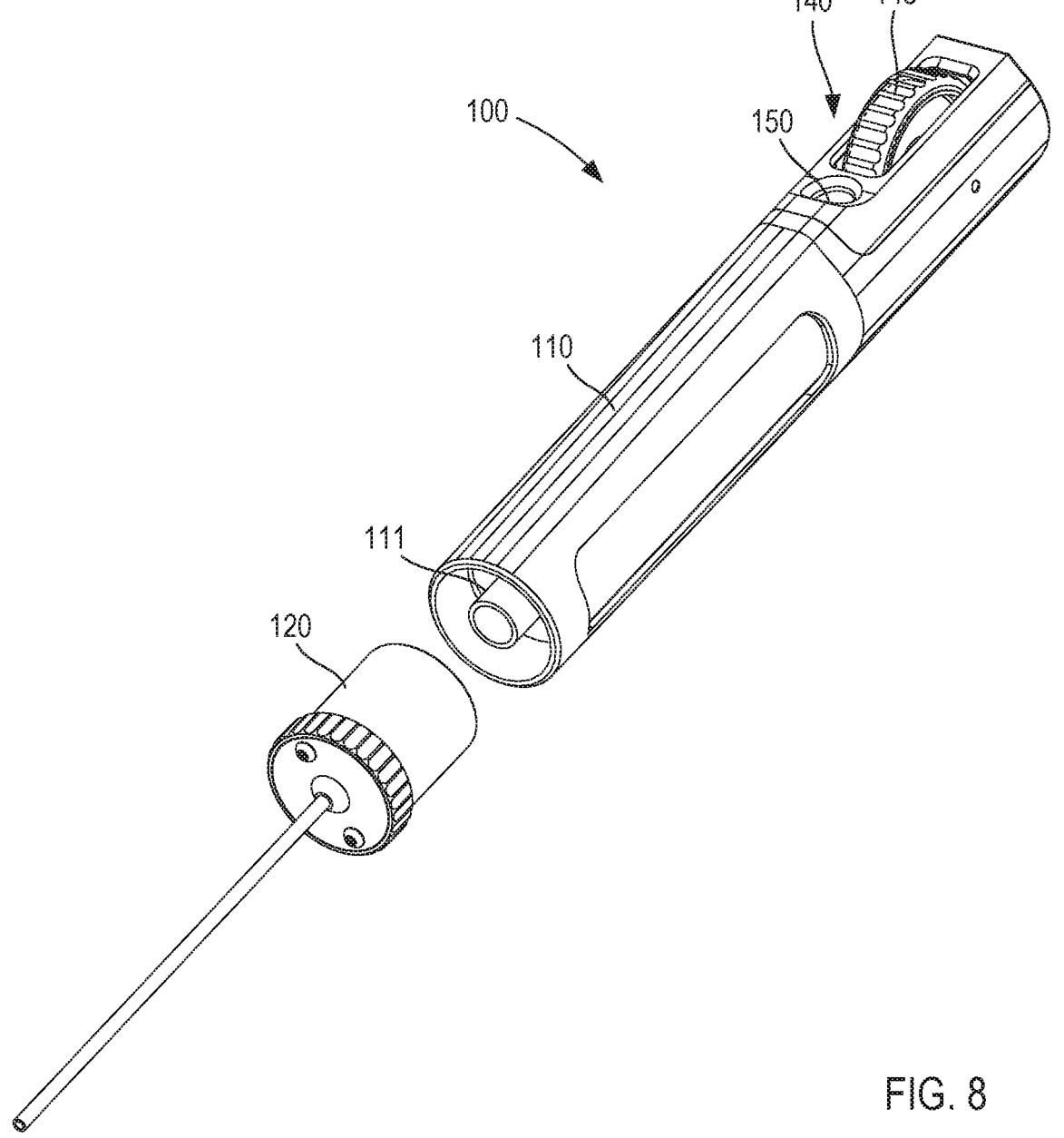
FIG. 8 is a partially exploded perspective view of the bodily fluid collection and distribution device of FIG. 2.

As shown in FIGS. 6-8, the inlet adapter 120 is configured to be at least temporarily coupled to the port 111 of the housing 110. The inlet adapter 120 can be any suitable shape, size, and/or configuration. The inlet adapter 120 can include a lumen-containing device configured to be in fluid communication with a bodily fluid source. For example, in some embodiments, the inlet adapter 120 can include a needle or catheter configured to be inserted into a vein or artery of a patient. In other embodiments, the inlet adapter 120 can include a catheter and/or other conduit configured to establish fluid communication between the inlet adapter 120 and an intermediate device (e.g., a diversion device, a placed intravenous catheter, and/or any other suitable device).

As shown in FIGS. 6 and 7, the inlet adapter 120 is fluidically coupled to the port 111 when the inlet adapter 120 is coupled to the housing 110. For example, in some embodiments, the port 111 of the housing 110 can include a needle or other puncture member configured to be advanced through a pierceable, sealable, and/or frangible portion of the inlet adapter 120. For example, the inlet adapter 120 can include a self-sealing port or the like that is pierced by the needle or puncture member of the port 111 when the inlet adapter 120 is coupled thereto and that returns to a sealed state or the like when the inlet adapter 120 is removed from the housing 110. In such embodiments, the needle and/or puncture member can place an internal portion of the inlet adapter 120 in fluid communication with the fluid reservoir 115, thereby allowing fluid (e.g., bodily fluid) to be transferred from the inlet adapter 120 into the fluid reservoir 115.

As shown in FIG. 8, in some instances, the inlet adapter 120 can be decoupled and/or otherwise removed from the housing 110 after a desired volume of fluid has been transferred into the fluid reservoir 115. Although not shown in FIG. 8, in some embodiments, decoupling of the inlet adapter 120 from the port 111 can be such that the needle and/or puncture member coupled to the port 111 is exposed, which in turn, can allow the port 111 to be physically and/or fluidically coupled to any suitable device and/or reservoir. For example, in some embodiments, the port 111 can be configured to physically and/or fluidically couple to a culture bottle or other sample reservoir. In other embodiments, the port 111 can be coupled to and/or can include any suitable transfer adapter such as, for example, those described in the '783 patent.

Although not shown in FIGS. 2-8, in some embodiments, the inlet adapter 120 can be configured to collect, divert, and/or sequester an initial volume of bodily fluid received from a bodily fluid source (e.g., a patient). For example, in some embodiments, the inlet adapter 120 can have a first state or configuration in which the initial volume of bodily fluid is transferred into a first portion of the inlet adapter 120 (e.g., via a first flow path or the like) and can be transitioned from the first state or configuration to a second state and/or configuration in which (1) the initial volume of bodily fluid is sequestered by or in the first portion of the inlet adapter 120 and (2) a subsequent volume of bodily fluid can be transferred, via a second flow path or the like, through the inlet adapter 120 and into the fluid reservoir 115. As such, the subsequent volume of bodily fluid can be substantially free from contaminants or the like that may otherwise be contained in the initial volume of bodily fluid. In other embodiments, the inlet adapter 120 can be configured to couple to a diversion device or the like configured to divert and sequester the initial volume of bodily fluid. In still other embodiments, the diversion device or the like can be integrated and/or included in the device 100 (e.g., at least partially disposed in the housing 110).

Collection, diversion, and/or sequestration of the initial volume of bodily fluid can be performed in any suitable manner by any suitable device or combination of devices. For example, in some embodiments, collection, diversion, and/or sequestration of the initial volume of bodily fluid can be performed using any of the devices (or portions thereof), concepts, and/or methods described above with reference to the device 1 shown in FIGS. 1A-1C and/or in the '420 patent, the '783 patent, the '241 patent, the '724 patent, the '495 patent, the '084 patent, the '240 publication, the '510 publication, the '006 publication, the '117 publication, the '074 publication, and/or the '087 publication, incorporated by reference hereinabove.

In some instances, a user can use the device 100 to obtain an amount of bodily fluid that is substantially free from contaminants and then can use device 100 to deliver at least one desired and accurate (e.g., proper, appropriate, and/or recommended) volume of the procured bodily fluid to a corresponding sample reservoir such as, for example, an aerobic or an anaerobic culture bottle. For example, as described above, a user can establish fluid communication between the fluid reservoir 115 and a bodily fluid source via the inlet adapter 120 and the port 111 of the housing 110. In some instances, the user can engage the device 100, the inlet adapter 120, and/or a device coupled to the inlet adapter 120 to divert and sequester an initial volume of bodily fluid. After diverting the initial volume of bodily fluid, the user can rotate the wheel 143 to transition and/or move the plunger 141 from a first state, configuration, and/or position (e.g., a distal position as shown in FIGS. 6 and 7) to a second state, configuration, and/or position (e.g., a proximal position not shown in FIGS. 2-8). The movement of the plunger 141 from the first state or position to the second state or position can result in an increase in a volume of the fluid reservoir 115, which in turn, can generate a negative pressure differential and/or a suction force operable in drawing a subsequent volume of bodily fluid—substantially free from contaminants otherwise contained in the sequestered initial volume—into the fluid reservoir 115.

After drawing a predetermined volume of bodily fluid into the fluid reservoir 115, the volume indicator 150 can transition (e.g., automatically) from its first state to its second state to provide the user with an indication that the predetermined volume is contained in the fluid reservoir 115. In some instances, the predetermined volume can be based on a desired volume configured to be transferred into an aerobic culture bottle (e.g., 10.0 mL of bodily fluid). In other embodiments, the predetermined volume can be any suitable volume. In some instances, the user can stop collecting bodily fluid after the predetermined volume is disposed in the fluid reservoir 115. In other embodiments, the user can continue to rotate the wheel 143 to draw additional amounts of bodily fluid into the fluid reservoir 115. In some embodiments, the user can engage and/or transition the volume indicator 150 to move the volume indicator 150 away from its second state, thereby enabling additional amounts of bodily fluid to be transferred into the fluid reservoir 115. As described above, in some embodiments, the arrangement of the actuator 140 can be configured to control, meter, and/or modulate a rate at which bodily fluid is transferred into the fluid reservoir 115, for example, by controlling, limiting, and/or modulating a rate at which the plunger 141 can be moved within or relative to the fluid reservoir 115. As such, a negative pressure differential and/or suction force within the fluid reservoir 115 can be modulated and/or limited. In addition, limiting a rate of fluid transfer into the fluid reservoir 115 can enhance and/or facilitate the collection of a proper, appropriate, recommended, and/or otherwise accurate volume of bodily fluid.

After transferring the desired amount of bodily fluid the user, for example, can remove the inlet adapter 120 from the port 111. The inlet adapter 120 and/or a volume of bodily fluid disposed therein can then be discarded and/or used for any other suitable process and/or purpose. In some instances, the user can then couple the port 111 to any suitable collection or sample reservoir such as, for example, a culture bottle (and/or any collection device described herein). Accordingly, the port 111 of the housing 110 can be used to transfer fluid into the fluid reservoir (e.g., acting as an inlet port) and to transfer fluid out of the fluid reservoir (e.g., acting as an outlet port).

In some instances, for example, it may be desirable to transfer a predetermined and/or desired volume of bodily fluid into an anaerobic culture bottle for use in the testing of samples incubated in an anaerobic culture medium, which can be relatively sensitive to false negatives as a result of insufficient sample volume. Moreover, in some embodiments, the volume indicator 150 can be configured to transition to and/or can automatically be placed in its second state in response to the predetermined and/or desired volume of bodily fluid being transferred into the collection or sample reservoir (e.g., the anaerobic culture bottle). In some embodiments, the predetermined and/or desired volume of bodily fluid can be about 10.0 mL. In some instances, additional amounts or volumes of the bodily fluid contained in the fluid reservoir 115 can be distributed into one or more additional collection and/or sample reservoirs based at least in part on a desired and/or predetermined volume of bodily fluid intended to be conveyed into that specific type of collection and/or sample reservoir (e.g., per a manufacturer's indication, instruction, and/or recommendation). Thus, the device 100 can be configured to obtain bodily fluid that is substantially free from contaminants and configured to distribute, into one or more collection or sample reservoirs and in desired volumes, the obtained bodily fluid.

Figure 9:
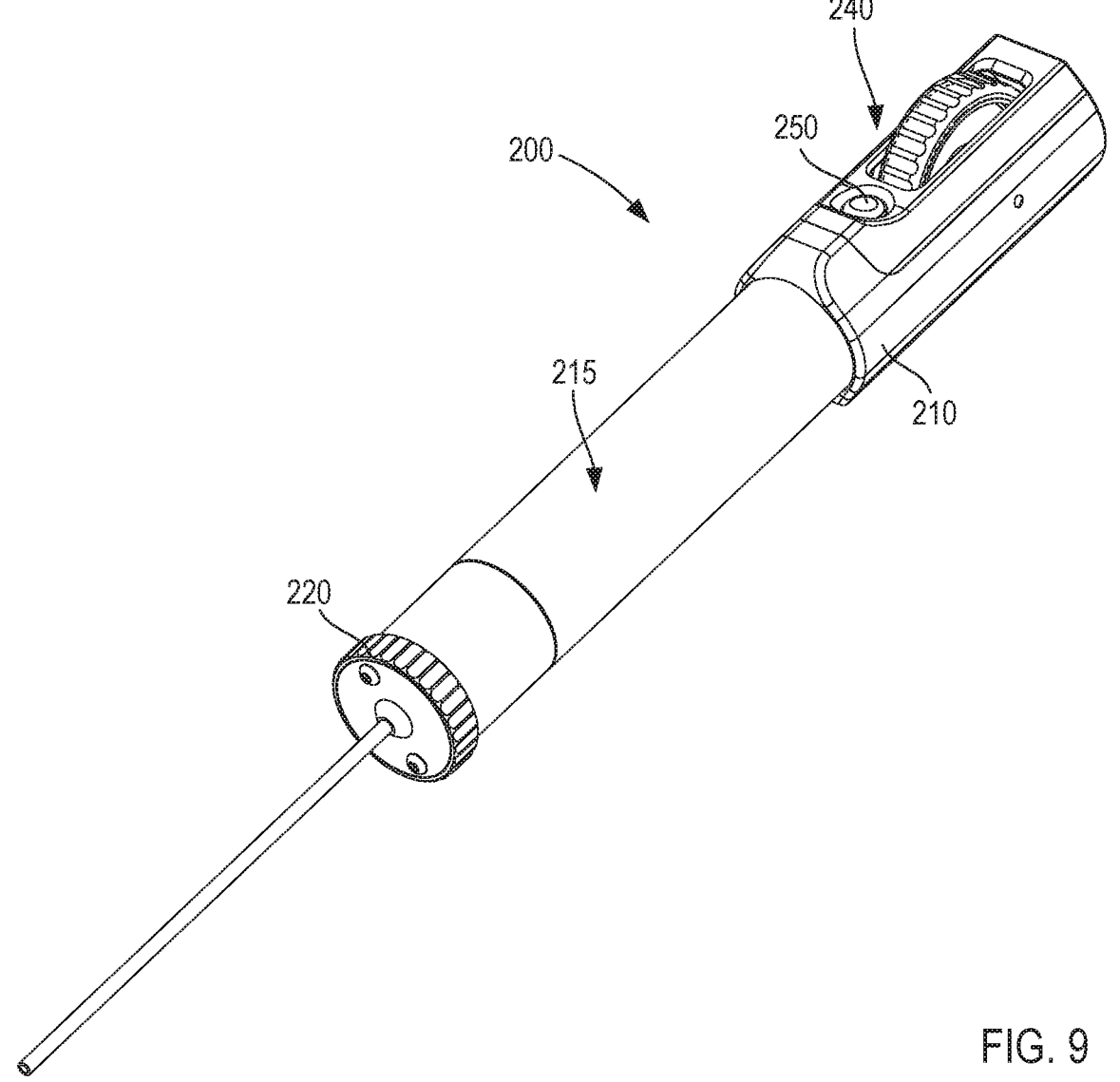
FIGS. 9-11 are a perspective view, a top view, and a left side view, respectively, of a bodily fluid collection and distribution device according to an embodiment.
Figures 10, 11:
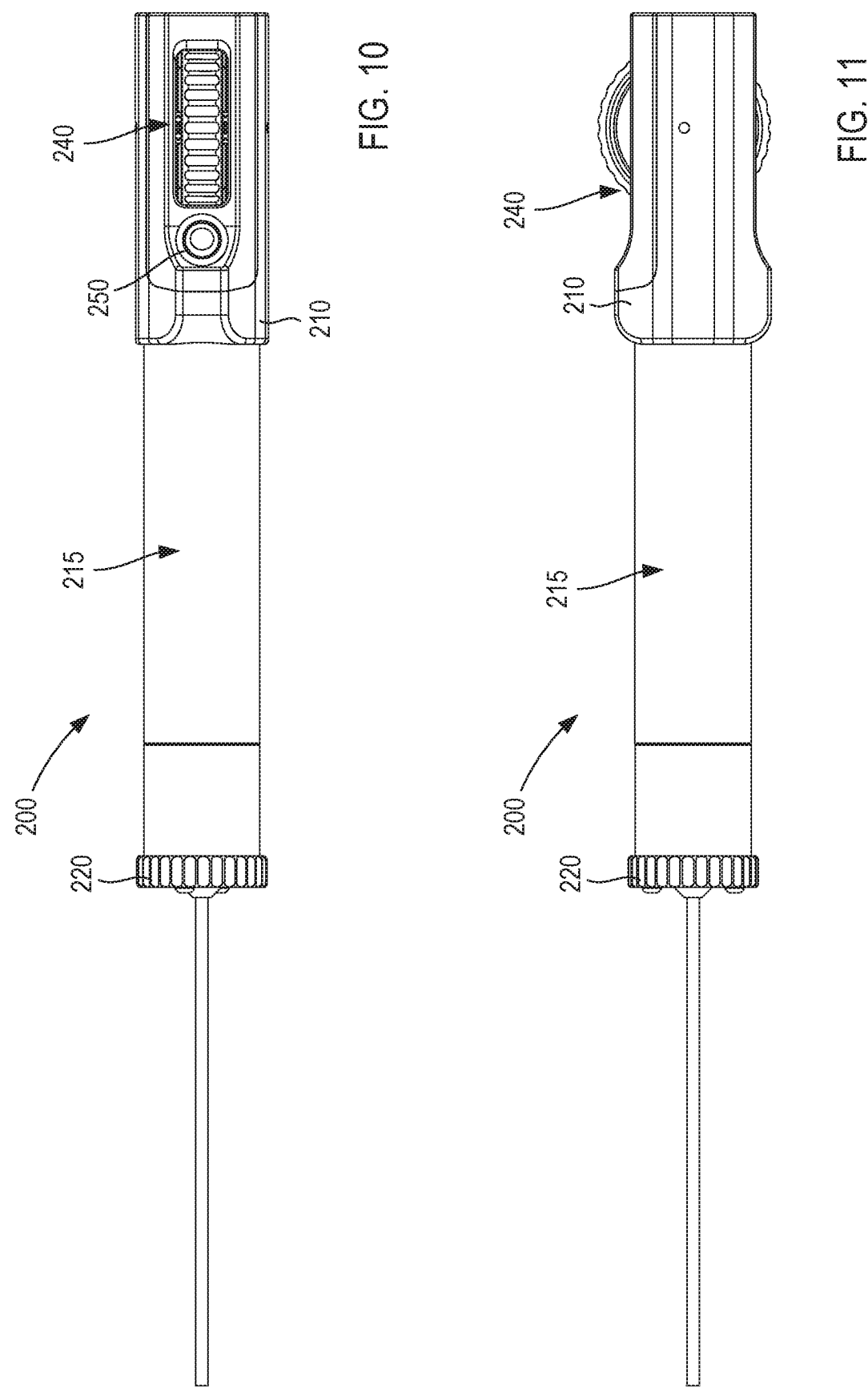

While the device 100 is particularly shown in FIGS. 2-8, in other embodiments, any suitable changes in form may be made without departing from the function described above. For example, FIGS. 9-11 illustrate a bodily fluid collection and distribution device 200 according to an embodiment. The bodily fluid collection and distribution device 200 (also referred to herein as "device" 200) includes a housing 210, a fluid reservoir 215, an inlet adapter 220, an actuator 240, and a volume indicator 250. The device 200 is substantially similar in form and/or function to the device 100 described above with reference to FIGS. 2-8. The device 200 can differ, however, in the arrangement and/or configuration of the housing 210. For example, the housing 110 included in the device 100 is configured to extend from a distal end portion of the device 100 to a proximal end portion of the device 100 (e.g., adjacent to the inlet adapter 120). As shown in FIGS. 9-11, the housing 210 extends from a distal end portion of the device 200 toward a proximal end portion of the 200 but is shorter than the housing 110 of the device 100. More particularly, the housing 210 is configured to stop in a position along a length of the device that is proximally adjacent to the volume indicator 250. In other aspects, the device 200 can be substantially similar to the device 100 and thus, is not described in further detail herein.

While the actuator 140 of the device 100 is particularly shown in FIGS. 2-8 and described above, in other embodiments, a bodily fluid collection and distribution device can include an actuator having any suitable configuration and/or arrangement without substantially departing from the function of the actuator 140 described above (unless expressly described otherwise). More particularly, the actuator 140 is configured to transition and/or move the plunger 141 between a first state and/or position (e.g., a distal position) to a second state and/or position (e.g., a proximal position) while controlling, limiting, and/or modulating a rate at which the plunger 141 can be moved within and/or relative to the fluid reservoir 115. In other embodiments, a bodily fluid collection device can include an actuator having any suitable arrangement and/or configuration that can similarly transition and/or move a plunger while controlling, limiting, and/or modulating a rate at which the plunger can be moved.

Figures 12, 13:
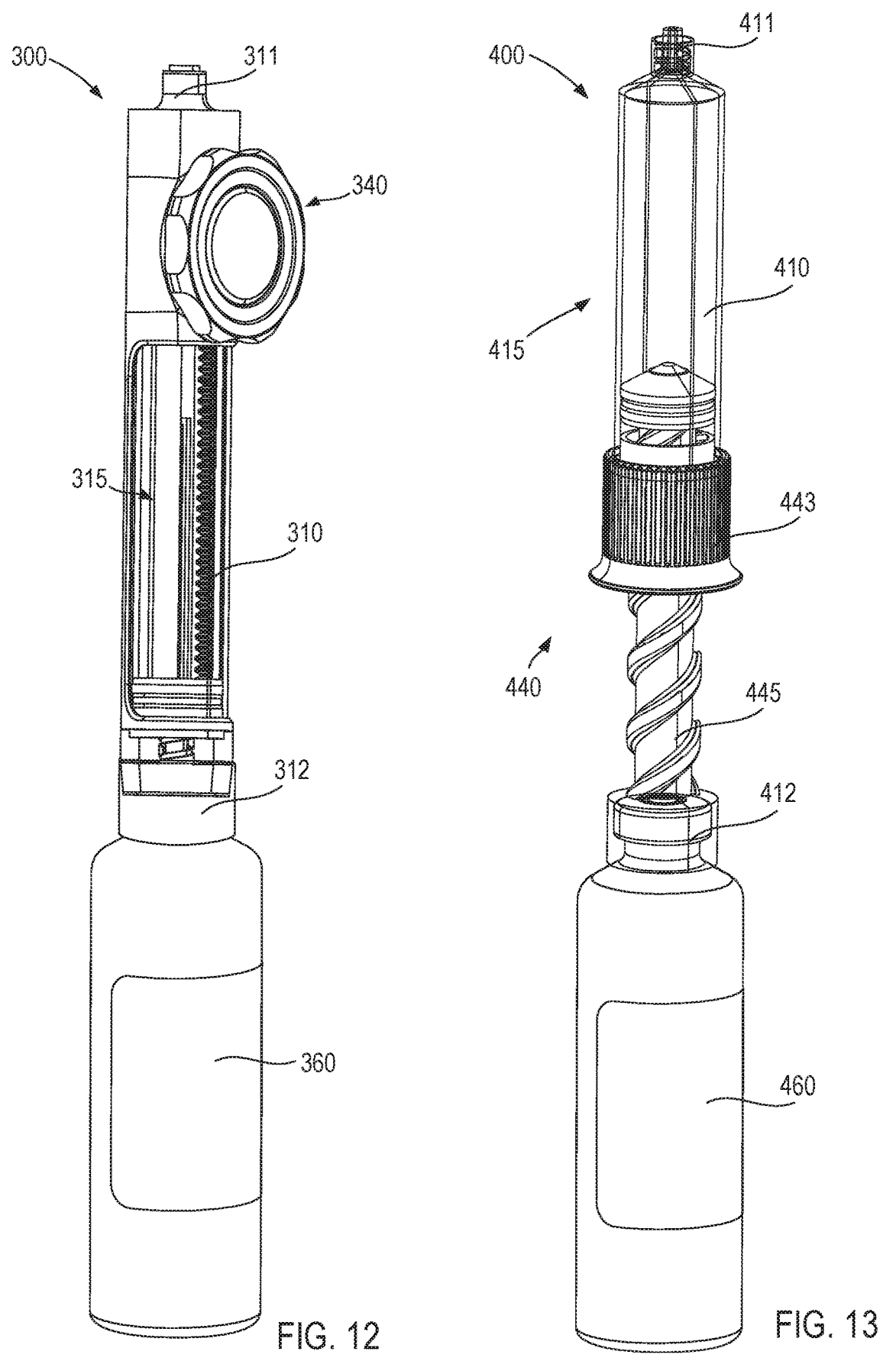
FIGS. 12-15 are various perspective views of bodily fluid collection and distribution devices each according to a different embodiment.

For example, FIG. 12 illustrates a bodily fluid collection and distribution device 300 according to an embodiment. The bodily fluid collection and distribution device 300 (also referred to herein as "device" 300) can be substantially similar in at least form and/or function to the devices 1, 100, and/or 200 described above. The device 300 can differ, however, in the arrangement and/or configuration of a housing and an actuator while still being configured to, among other things, control, limit, meter, and/or modulate a rate of fluid transfer into and/or out of the device 300.

As shown in FIG. 12, the device 300 includes at least a housing 310, a fluid reservoir 315, and an actuator 340. The housing 310 includes an inlet port 311 and an outlet port 312. The housing 310 can be similar in form and/or function to the housing 110 described above. As such, the housing 310 includes, contains, and/or at least partially houses the fluid reservoir 315 and the actuator 340. The inlet port 311 is configured to receive a flow of fluid (e.g., from a bodily fluid source). In some embodiments, the inlet port 311 can be coupled to an inlet adapter similar, for example, to the inlet adapter 120 described above. In other embodiments, the inlet port 311 can be placed in fluid communication with a needle, catheter, and/or lumen-defining device at least partially disposed in a patient. In still other embodiments, the inlet port 311 can be placed in fluid communication with a diverter and/or a diversion device such as any of those described herein.

Although not shown in FIG. 12, in some embodiments, the inlet port 311 and/or the housing 310 can form and/or define a channel, conduit, and/or flow path configured to place the inlet port 311 in fluid communication with a desired portion of the fluid reservoir 315. For example, the inlet port 315 shown in FIG. 12 can be disposed on or at a distal end portion of the housing 310 and can include a channel, conduit, and/or flow path (not shown) that can place the inlet port 311 in fluid communication with a proximal end portion of the housing 310 and/or a proximal end portion of the fluid reservoir 315. In other embodiments, the inlet port 311 can be disposed at any suitable position on or along the housing 310.

The outlet port 312 of the housing 310 is in fluid communication with a portion of the fluid reservoir 315, as described in further detail herein. In some embodiments, the outlet port 312 can be disposed, for example, on, at, or near a proximal end portion of the housing 310. For example, as shown in FIG. 12, the outlet port 312 can be disposed at a proximal end portion of the housing 310 and can be substantially opposite the inlet port 311.

The outlet port 312 is configured to be physically and/or fluidically coupled to a collection device such as any of those described herein. For example, as shown in FIG. 12, the outlet port 312 can be physically and fluidically coupled to a sample or culture bottle. In some embodiments, the outlet port 312 can include a sheathed needle and/or other suitable puncture member configured to puncture a portion of a collection device to establish fluid communication therebetween. In other embodiments, the outlet port 312 can include any suitable feature, member, device, and/or the like configured to establish fluid communication between the outlet port 312 and the collection device.

The actuator 340 of the device is substantially similar in form and/or function to the actuator 140 described above with reference to the device 100. For example, the actuator 340 can include a wheel configured to be rotated by a user to move a plunger within and/or relative to the housing 310 and/or fluid reservoir 315 (e.g., moved between a first state and/or position and a second state and/or position). The actuator 340 can differ from the actuator 140, however, by the position and/or orientation of the wheel. For example, as shown in FIG. 12, the wheel can be configured to rotate about an axis that is substantially perpendicular to an axis about which the wheel 143 of the actuator 140 rotates. In some embodiments, the arrangement of the actuator 340 can be such that the plunger and/or a seal included in or on the plunger is disposed in a proximal position within the fluid reservoir 315 (as shown in FIG. 12) when the plunger is in the first state and/or position and can be in a distal position within the fluid reservoir 315 when the plunger is in the second state. Moreover, the actuator 340 can be configured to control, limit, meter, and/or modulate a rate at which the plunger is moved within or relative to the fluid reservoir 315, as described in detail above with reference to the device 100.

Although not shown in FIG. 12, the inlet port 311 of the housing 310 and the outlet port 312 of the housing 310 are each in fluid communication with a portion of the fluid reservoir 315 that is proximal to the plunger and/or seal of the plunger. In some instances, manipulating the wheel to move the plunger from the first state or position to the second state or position can be operable in drawing a volume of fluid into the fluid reservoir 315 (e.g., proximal to the plunger or seal thereof) via the inlet port 311 and manipulating the wheel to move the plunger from the second state or position to the first state or position can be operable in conveying at least a portion of the volume of fluid from the fluid reservoir 315 via the outlet port 312. Thus, the device 100 can be configured to obtain bodily fluid that is substantially free from contaminants and configured to distribute, into one or more collection or sample reservoirs and in desired volumes, the obtained bodily fluid, as described above with reference to the devices 1, 100, and/or 200.

FIG. 13 illustrates a bodily fluid collection and distribution device 400 according to another embodiment. The bodily fluid collection and distribution device 400 (also referred to herein as "device" 400) can be substantially similar in at least form and/or function to the devices 100, 200, and/or 300 described above. The device 400 can differ, however, in the arrangement and/or configuration of an actuator while still being configured to, among other things, control, limit, meter, and/or modulate a rate of fluid transfer into and/or out of the device 400.

As shown in FIG. 13, the device 400 includes at least a housing 410, a fluid reservoir 415, and an actuator 440. The housing 410 includes an inlet port 411 configured to convey a flow of fluid (e.g., bodily fluid) into the fluid reservoir 415 and an outlet port 412 configured to convey a flow of fluid (e.g., bodily fluid) out of the fluid reservoir 415. In some embodiments, the housing 410 can be substantially similar in form and/or function to the housing 310 described above. As such, the housing 410 is not described in further detail herein.

The actuator 440 of the device is substantially similar in at least function to at least the actuator 140 and/or 340 described above. For example, the actuator 440 can include an engagement member 443 (e.g., similar to the wheels 143, 243, and/or 343) configured to be rotated by a user to move a plunger within and/or relative to the housing 410 and/or fluid reservoir 415 (e.g., moved between a first state and/or position and a second state and/or position). The actuator 440 can differ, however, by including a plunger that includes and/or that is arranged as a lead screw, worm gear, and/or any other threaded member configured to engage a corresponding inner portion of the engagement member 443. As such, rotating the engagement member 443 can transition and/or move the plunger relative to and/or within the fluid reservoir 415. Moreover, the actuator 440 can be configured to control, limit, meter, and/or modulate a rate at which the plunger is moved within or relative to the fluid reservoir 415, as described in detail above with reference to the device 100. Thus, the device 400 can be configured to obtain bodily fluid that is substantially free from contaminants and configured to distribute, into one or more collection or sample reservoirs and in desired volumes, the obtained bodily fluid, as described above with reference to any of the devices 1, 100, 200, and/or 300.

Figure 14:
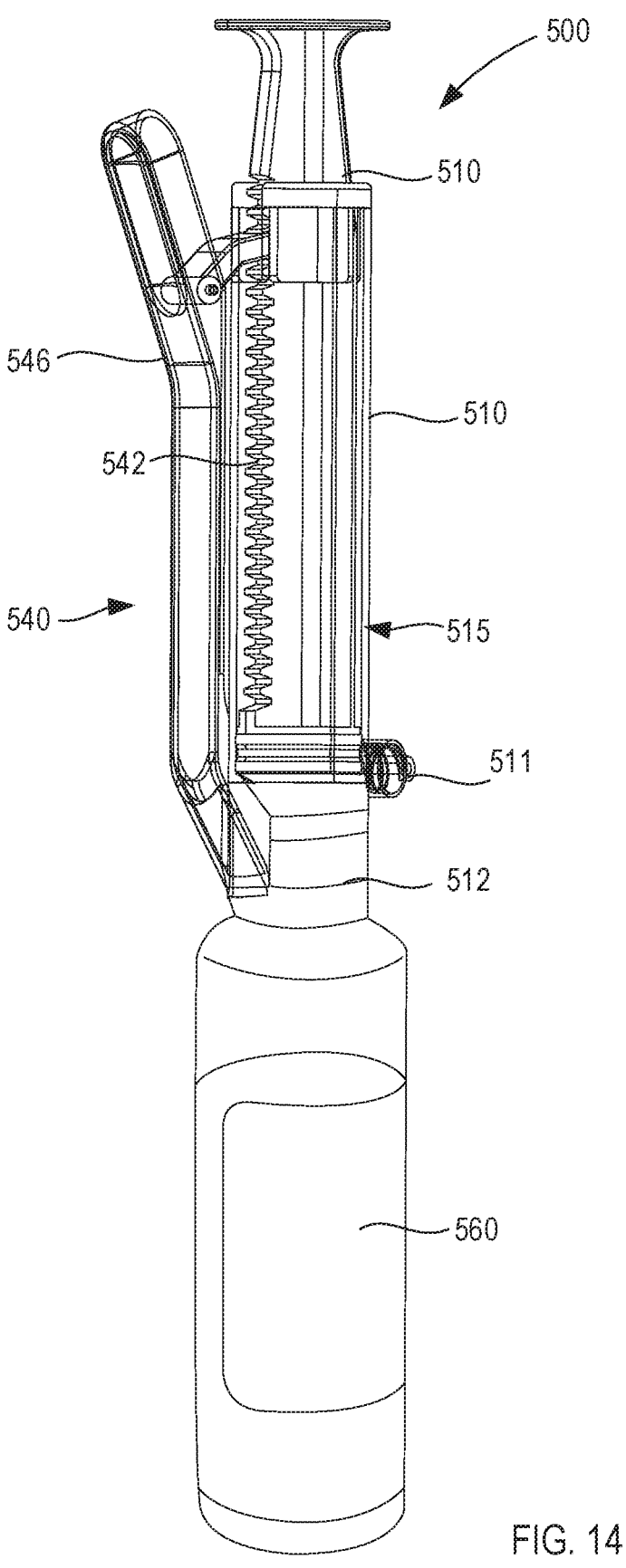

FIG. 14 illustrates a bodily fluid collection and distribution device 500 according to another embodiment. The bodily fluid collection and distribution device 500 (also referred to herein as "device" 500) can be substantially similar in at least form and/or function to the devices 1, 100, 200, 300, and/or 400 described above. The device 500 can differ, however, in the arrangement and/or configuration of an actuator while still being configured to, among other things, control, limit, meter, and/or modulate a rate of fluid transfer into and/or out of the device 500.

As shown in FIG. 14, the device 500 includes at least a housing 510, a fluid reservoir 515, and an actuator 540. The housing 510 includes an inlet port 511 configured to convey a flow of fluid (e.g., bodily fluid) into the fluid reservoir 515 and an outlet port 512 configured to convey a flow of fluid (e.g., bodily fluid) out of the fluid reservoir 515. In some embodiments, the housing 510 can be substantially similar in form and/or function to the housings 10, 110, 210, 310, and/or 410 described above. As such, the housing 510 is not described in further detail herein.

The actuator 540 of the device is substantially similar in at least function to at least the actuator 140 described above with reference to the device 100. While the actuator 140 is described above as including the wheel 143 configured to rotate one or more pinions 144 to transition and/or move the plunger 141, the actuator 540 includes a lever 546 configured to engage a rack 542 coupled to, included in or on, and/or otherwise formed by a plunger 541. In the embodiment shown in FIG. 14, a user can engage a portion of the plunger 541 to move the plunger 541 within and/or relative to the housing 510 and/or fluid reservoir 515 between a first state and/or position (FIG. 14) and a second state and/or position. Moreover, in some instances, the lever 546 can engage the rack 542 of the plunger 541 to control, limit, meter, and/or modulate a rate at which the plunger 541 is moved within or relative to the fluid reservoir 515, as described in detail above with reference to the device 100. In some instances, the user can exert a desired amount of force on the lever 546 while moving the plunger 541 to further modulate a rate at which the plunger 541 is moved and/or an ease associated with moving the plunger 541. Thus, the device 500 can be configured to obtain bodily fluid that is substantially free from contaminants and configured to distribute, into one or more collection or sample reservoirs and in desired volumes, the obtained bodily fluid, as described above with reference to any of the devices 1, 100, 200, 300, and/or 400.

Figure 15:
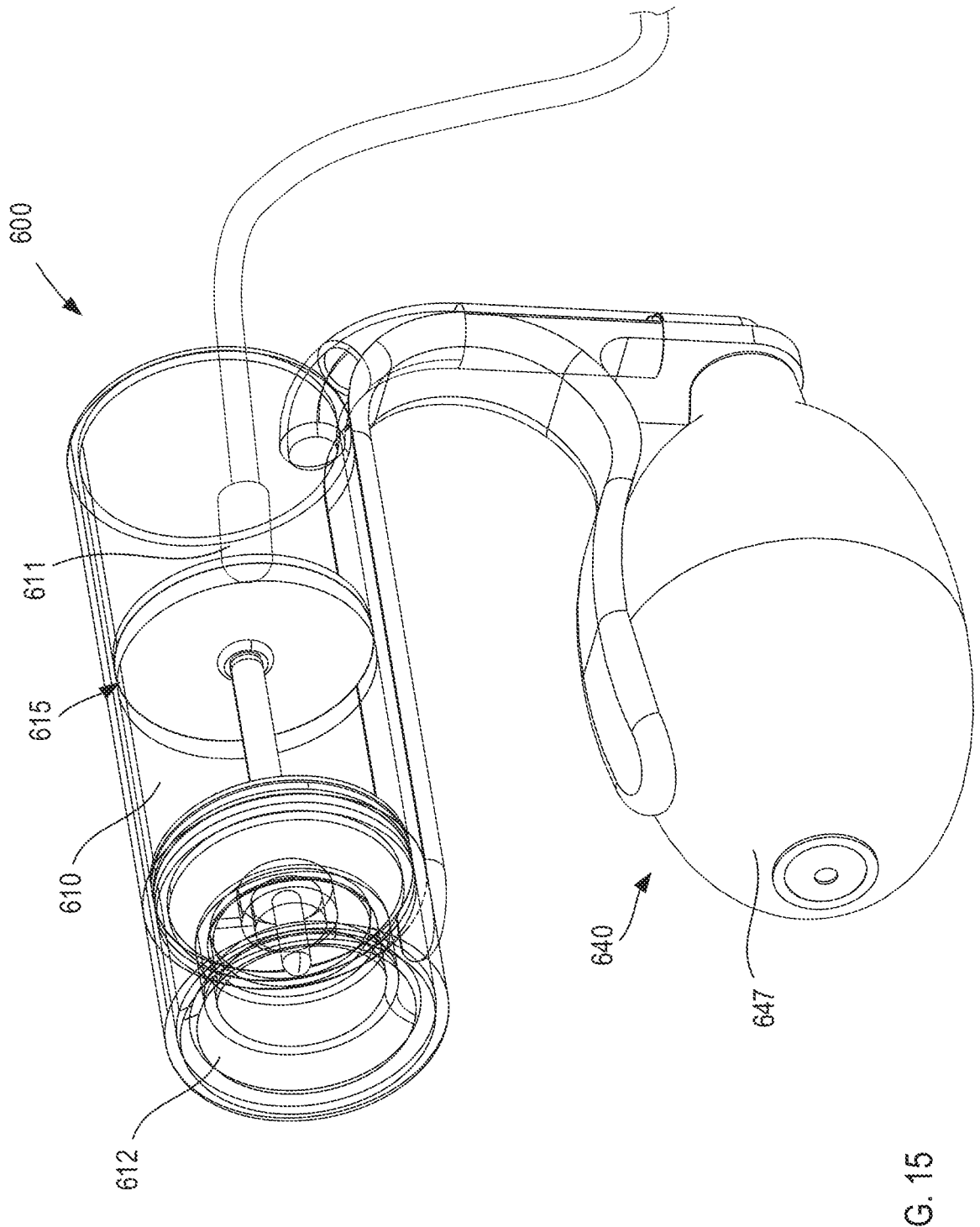
Figures 16, 17:
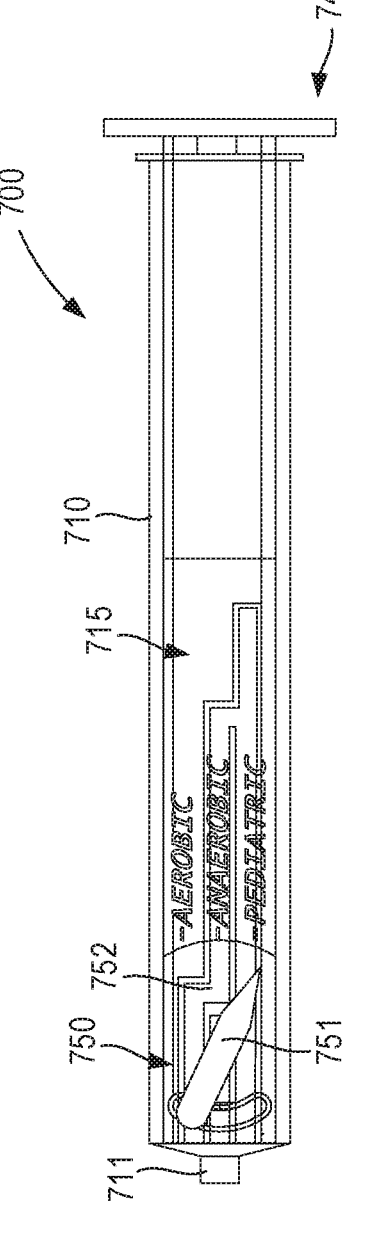
FIGS. 16-19 are each a top view of a bodily fluid collection and distribution device according to an embodiment, shown in a first state, a second state, a third state, and a fourth state, respectively.

FIG. 15 illustrates a bodily fluid collection and distribution device 600 according to another embodiment. The bodily fluid collection and distribution device 600 (also referred to herein as "device" 600) can be substantially similar in at least form and/or function to the devices 1, 100, 200, 300, 400, and/or 500 described above. The device 600 can differ, however, in the arrangement and/or configuration of an actuator while still being configured to, among other things, control, limit, meter, and/or modulate a rate of fluid transfer into and/or out of the device 600.

As shown in FIG. 15, the device 600 includes at least a housing 610, a fluid reservoir 615, and an actuator 640. The housing 610 includes an inlet port 611 configured to convey a flow of fluid (e.g., bodily fluid) into the fluid reservoir 615 and an outlet port 612 configured to convey a flow of fluid (e.g., bodily fluid) out of the fluid reservoir 615. In some embodiments, the housing 610 can be substantially similar in form and/or function to the housings 10, 110, 210, 310, and/or 410 described above. As such, the housing 610 is not described in further detail herein.

The actuator 640 of the device is substantially similar in at least function to at least the actuator 140 described above with reference to the device 100. While the actuator 140 is described above as including the wheel 143 configured to rotate one or more pinions 144 to transition and/or move the plunger 141, the actuator 640 is configured to produce, generate, and/or create a negative pressure differential and/or suction force operable to move a plunger of the actuator 640. For example, as shown in FIG. 15, the actuator 640 includes a bulb 647 that is in fluid communication with a portion of the fluid reservoir 615. In use, the bulb 647 can be squeezed by a user to transition the actuator 640 and/or plunger thereof between a first state and a second state. More particularly, in response to the bulb 647 being squeezed by the user, air and/or other contents within the bulb 647 can be expelled to the ambient environment or atmosphere (e.g., via a one-way valve or the like, not shown in FIG. 15). After expelling the contents, the user can release the bulb 647 allowing the bulb 647 to return to an uncompressed state. In turn, a volume within the bulb 647 is increased which results in a negative pressure differential and/or suction force being exerted in or on the portion of the fluid reservoir 615 in communication with the bulb 647. The negative pressure differential and/or suction force, in turn, is sufficient to move the plunger within the fluid reservoir 615.

In some embodiments, the configuration of the bulb 647 is such that an amount or magnitude of the negative pressure differential and/or suction force exerted in or on the fluid reservoir 615 is limited and/or controlled. In some instances, the bulb 647 is squeezed numerous times to move the plunger a desired amount or distance (e.g., from the first state or position to the second state or position). Accordingly, the actuator 640 can be configured to control, limit, meter, and/or modulate a rate at which the plunger is moved within or relative to the fluid reservoir 615, as described in detail above with reference to the device 100. Thus, the device 600 can be configured to obtain bodily fluid that is substantially free from contaminants and configured to distribute, into one or more collection or sample reservoirs and in desired volumes, the obtained bodily fluid, as described above with reference to any of the devices 1, 100, 200, 300, 400, and/or 500.

While the volume indicator 150 of the device 100 is particularly shown in FIGS. 2-8 and described above, in other embodiments, a bodily fluid collection and distribution device can include a volume indicator having any suitable configuration and/or arrangement without substantially departing from the function of the volume indicator 150 described above (unless expressly described otherwise). More particularly, the volume indicator 150 is configured to transition and/or move from a first state to a second state in response to a known, desired, and/or predetermined volume of bodily fluid being disposed in the fluid reservoir 115. In addition, in some embodiments, the volume indicator 150 can be configured to selectively pause, limit, and/or prevent additional amounts of bodily fluid from being transferred into the fluid reservoir 115 while the volume indicator 115 is in the second state, as described above. In other embodiments, a bodily fluid collection device can include a volume indicator having any suitable arrangement and/or configuration that can similarly transition and/or move between at least a first state and a second state to indicate and/or control a volume of bodily fluid disposed within, allowed to be disposed within, and/or configured to be dispensed from a fluid reservoir.

For example, FIGS. 16-19 illustrate a bodily fluid collection and distribution device 700 according to an embodiment, shown in a first state, a second state, a third state, and a fourth state, respectively. The bodily fluid collection and distribution device 700 (also referred to herein as "device" 700) can be substantially similar in at least form and/or function to at least the device 100 described above. The device 700 can differ, however, in the arrangement and/or configuration of a volume indicator while still being configured to, among other things, provide an indication of a volume of fluid (e.g., bodily fluid) within the device 700 and/or control, limit, and/or distribute at least a portion of the volume of the fluid within the device 700.

As shown in FIGS. 16-19, the device 700 includes at least a housing 710, a fluid reservoir 715, an actuator 740, and a volume indicator 750. The housing 710 includes a port 711 configured to convey a flow of fluid (e.g., bodily fluid) into and/or out of the fluid reservoir 715. In some embodiments, the housing 710 can be substantially similar in form and/or function to the housings 10 and/or 110 described above. In some embodiments, the housing 710 can be similar to a housing of a syringe and/or the like. As such, certain portions and/or aspects of the housing 710 are not described in further detail herein.

The actuator 740 can be any suitable shape, size, and/or configuration. In some embodiments, the actuator 740 can include at least a plunger configured to be transitioned and/or moved within and/or relative to the fluid reservoir 715. In some embodiments, for example, the actuator 740 is similar in at least form and/or function to any of the actuators 40, 140, 240, 340, 440, 540, and/or 640 described above. In other embodiments, the actuator 740 can be similar to an actuator of a syringe and/or the like. As such, certain portions and/or aspects of the actuator 740 are not described in further detail herein.

The volume indicator 750 of the device 700 can be any suitable shape, size, and/or configuration and can be configured to provide an indication of a volume of fluid (e.g., bodily fluid) within the fluid reservoir 715 and/or control, limit, and/or distribute at least a portion of the volume of the fluid within the fluid reservoir 715, as described in detail above with reference to the device 100. As shown in FIGS. 16-19, the volume indicator 750 includes an indication member 751 (e.g., an arm, arrow, rod, dial, and/or any other suitable indicator). Moreover, in some embodiments, a portion of the housing 710 (e.g., a surface such as an outer surface) can define a track 752 within which at least a portion of the indication member 751 is disposed. The indication member 751 is configured to rotate relative to the housing 710 to move a portion of the indication member 751 through one or more portions of the track 752 based at least in part on a position of the plunger within the housing 710 (and thus, a volume of fluid within the fluid reservoir 715). Furthermore, based on the portion of the track 752 in which the portion of the indication member 751 is disposed, the indication member 751 can be aligned with and/or can point to one or more indicia on the housing 710 or device 700 that is associated with and/or indicative of a known, predetermined, and/or desired volume of fluid disposed in the fluid reservoir 715.

Figure 18:
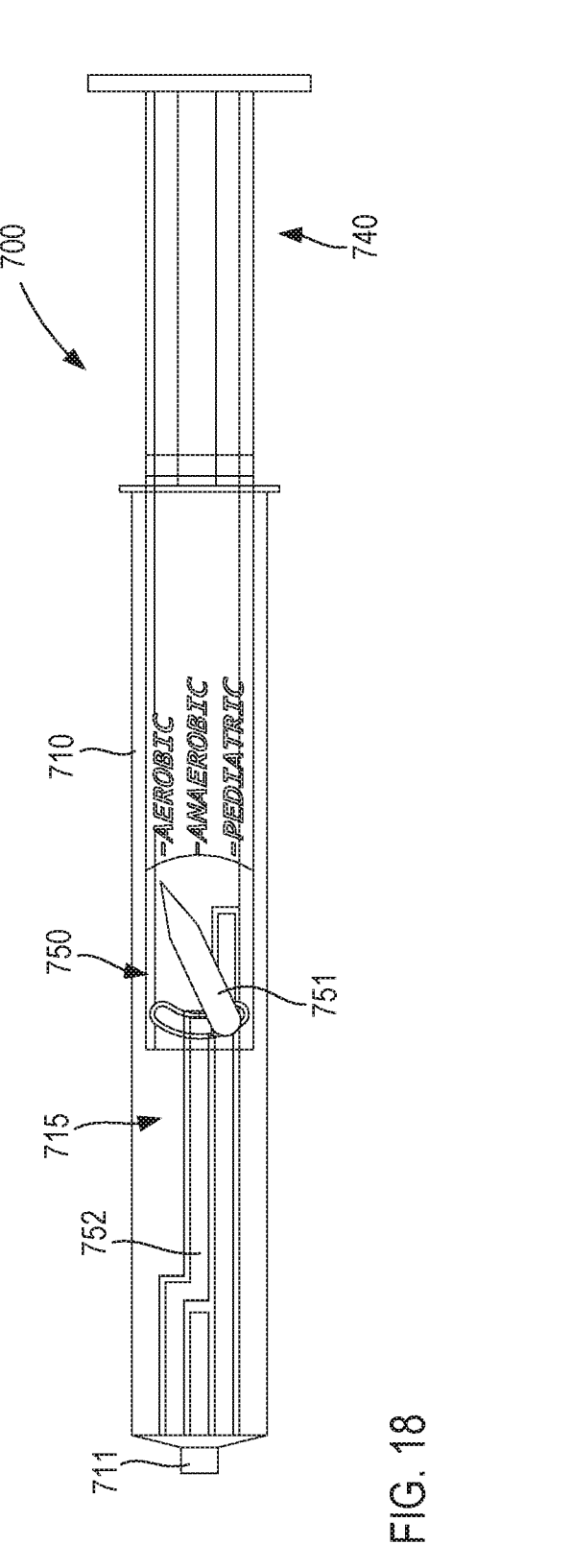
Figure 19:
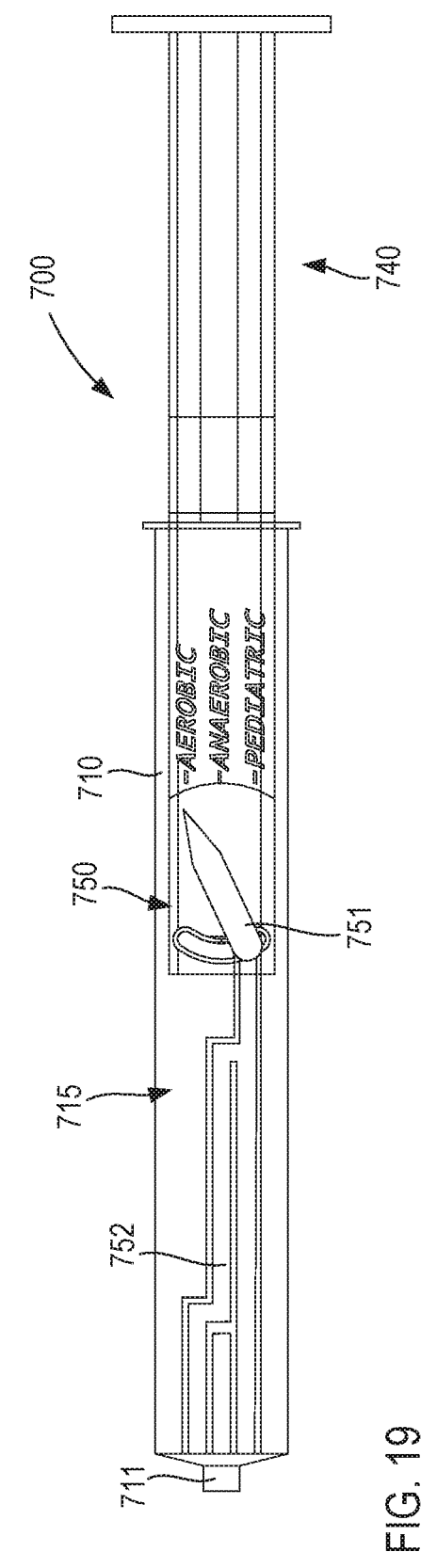

For example, the indication member 751 can be aligned with indicia such as "Pediatric" and a portion of the indication member 751 can be disposed in a first portion of the track 752 (e.g., a pediatric portion of the track 752) when the volume indicator 750 is in a first state (FIG. 16); the indication member 751 can be aligned with indicia such as "Anaerobic" and the portion the indication member 751 can be disposed in a second portion of the track 752 (e.g., an anaerobic portion of the track 752) when the volume indicator 750 is in a second state (FIG. 17); and the indication member 751 can be aligned with indicia such as "Aerobic" and the portion of the indication member 751 can be disposed in a third portion of the track 752 (e.g., an aerobic portion of the track 752) when the volume indicator 750 is in a third state (FIGS. 18 and 19).

In use, a user can manipulate the actuator 740 to draw a flow of fluid (e.g., bodily fluid) through the port 711 of the housing 710 and into the fluid reservoir 715. In some instances, the volume indicator 750 can be in the first state (FIG. 16) and the user can manipulate the actuator 740 to draw a predetermined volume of fluid suitable for testing a sample withdrawn from a pediatric patient (e.g., a relatively small volume) into the fluid reservoir 715 until the portion of the indication member 751 reaches an end of the first portion of the track 752. In some embodiments, the indication member 751 reaching the end of the first portion of the track 752 can limit and/or substantially prevent additional amounts and/or volumes of bodily fluid to be drawn into the fluid reservoir 715 until the volume indicator 750 is transitioned from the first state to the second state.

In some instances, the volume indicator 750 can be placed in the second state (FIG. 17) and the user can manipulate the actuator 740 to draw a predetermined volume of fluid suitable for anaerobic culture testing (e.g., a volume greater than the pediatric volume) into the fluid reservoir 715 until the portion of the indication member 751 reaches an end of the second portion of the track 752. In some embodiments, the indication member 751 reaching the end of the second portion of the track 752 can limit and/or substantially prevent additional amounts and/or volumes of bodily fluid to be drawn into the fluid reservoir 715 until the volume indicator 750 is transitioned from the second state to the third state.

In some instances, the volume indicator 750 can be placed in the third state (FIGS. 18 and 19) and the user can manipulate the actuator 740 to draw a predetermined volume of fluid suitable for aerobic culture testing (e.g., a volume greater than the anaerobic volume) into the fluid reservoir 715 until the portion of the indication member 751 reaches an end of the third portion of the track 752 (e.g., a fourth state as shown in FIG. 19). In some embodiments, the indication member 751 reaching the end of the portion of the track 752 can limit and/or substantially prevent additional amounts and/or volumes of bodily fluid to be drawn into the fluid reservoir 715. In other words, the end of the third portion of the track 752 can be a stop or limit to or on a range of motion of the actuator 740 relative to the housing 710. In some instances, the user can manipulate the actuator 740 to convey the volume of bodily fluid from the fluid reservoir 715 into one or more sample or culture bottles (or the like) based at least in part on the amount or volume of bodily fluid contained in the fluid reservoir. Thus, the volume indicator 750 can provide an indication associated with the amount or volume of bodily fluid disposed in the fluid reservoir 715 and can provide a means for distributing the bodily fluid into one or more collection devices based at least in part on the volume of bodily fluid disposed therein.

Figure 20:
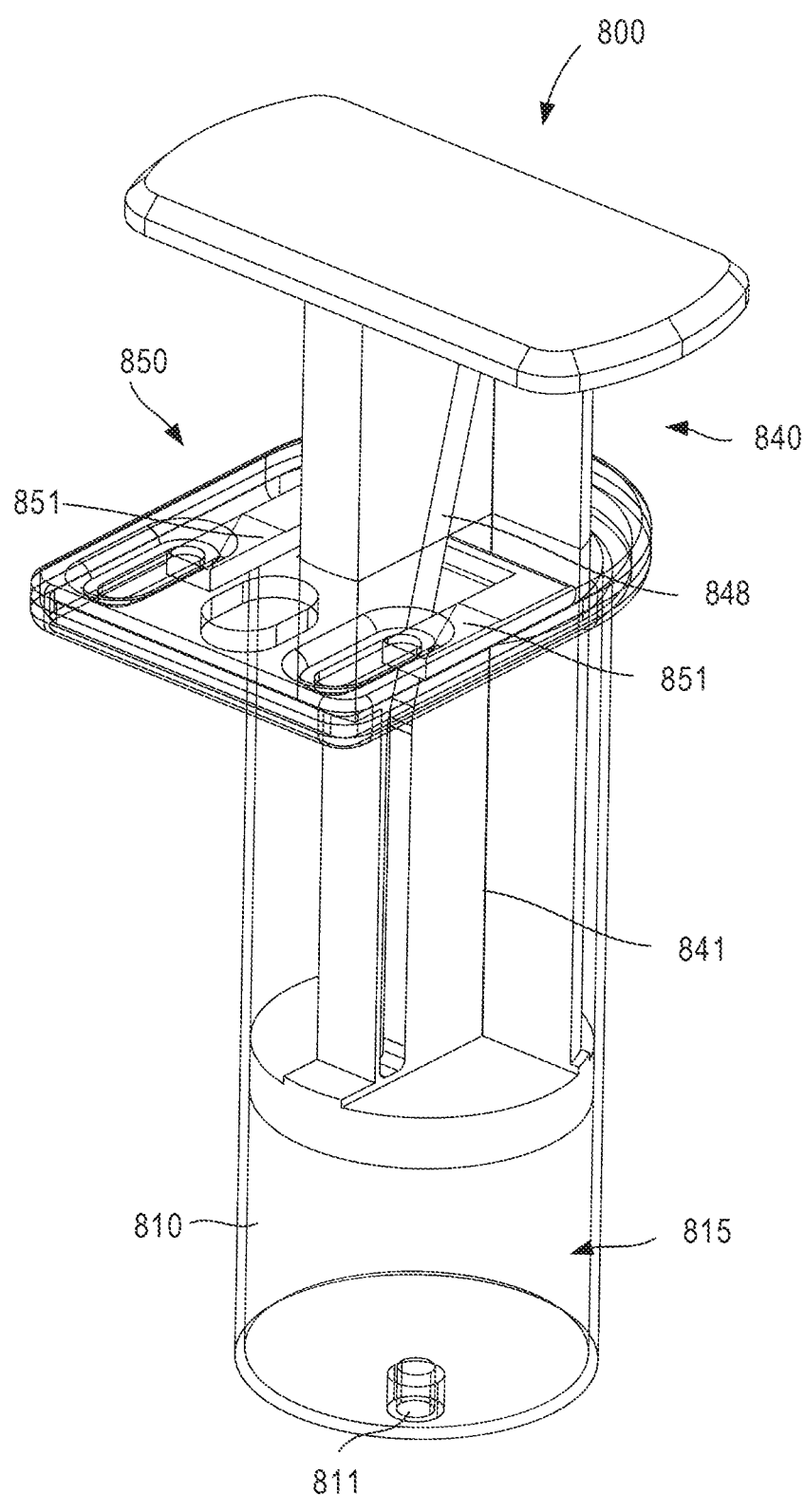
FIGS. 20-22 are each a perspective view of a bodily fluid collection and distribution device according to an embodiment, shown in a first state, a second state, and a third state, respectively.
Figure 21:
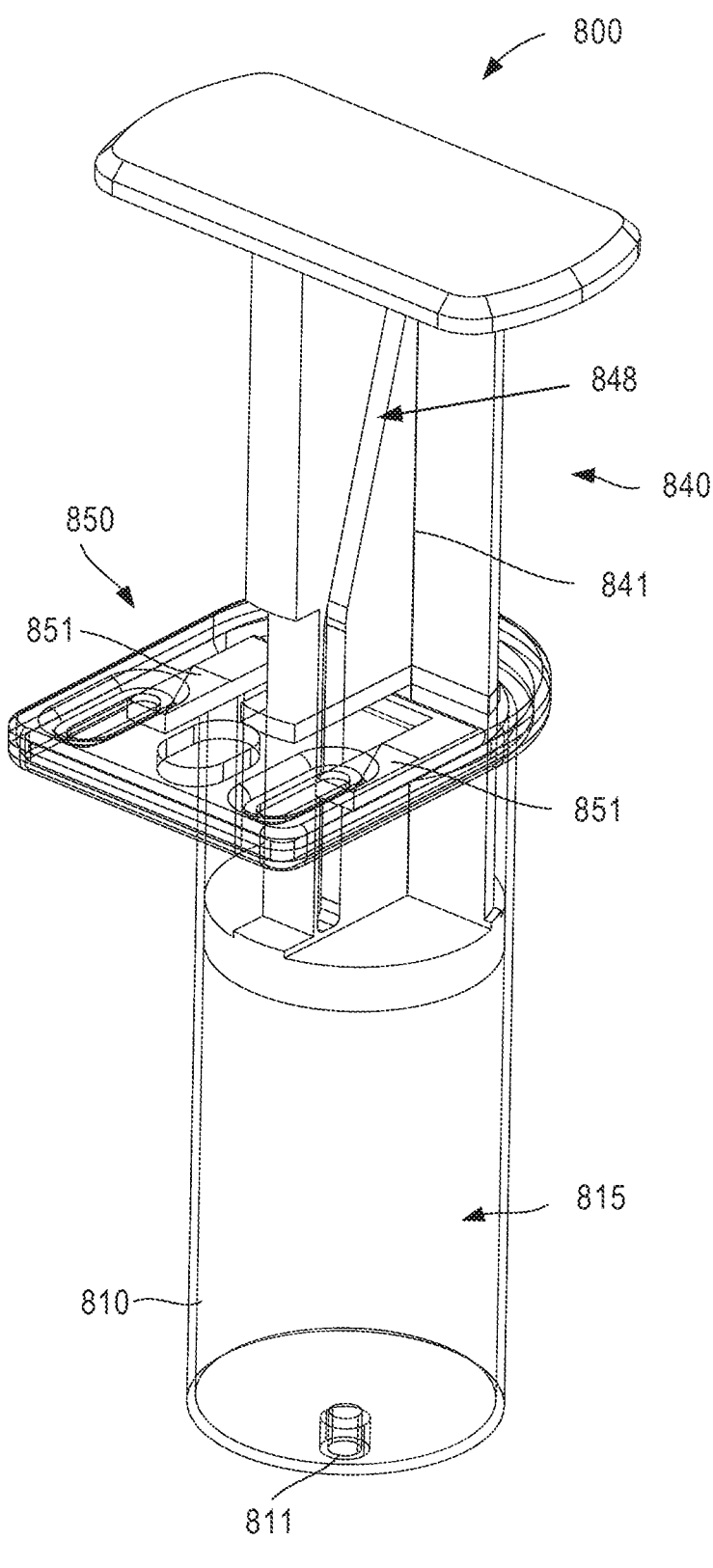
Figure 22:
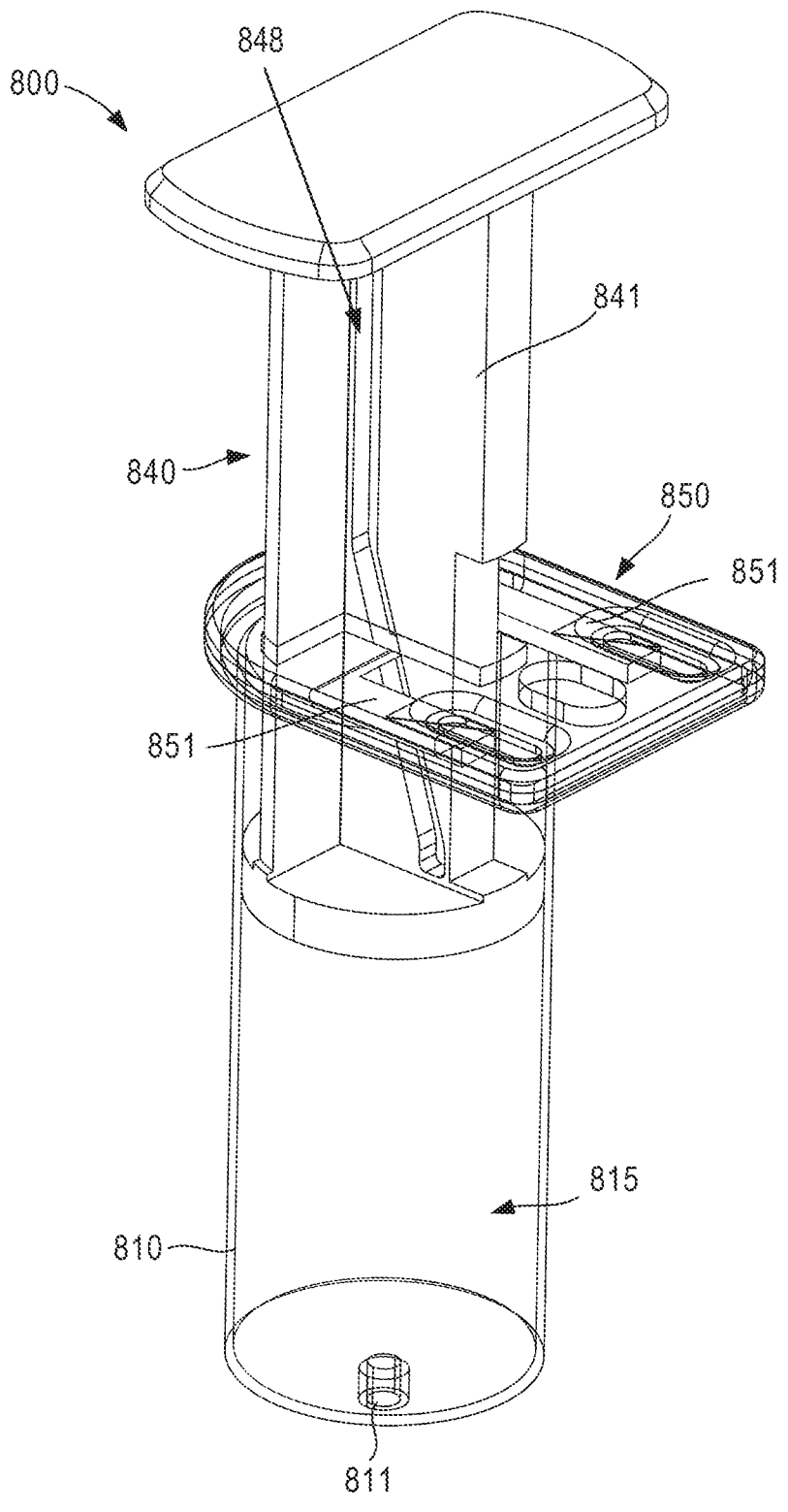

FIGS. 20-22 illustrate a bodily fluid collection and distribution device 800 according to another embodiment, shown in a first state, a second state, and a third state, respectively. The bodily fluid collection and distribution device 800 (also referred to herein as "device" 800) can be substantially similar in at least form and/or function to at least the devices 100 and/or 700 described above. The device 800 can differ, however, in the arrangement and/or configuration of a volume indicator while still being configured to, among other things, provide an indication of a volume of fluid (e.g., bodily fluid) within the device 800 and/or control, limit, and/or distribute at least a portion of the volume of the fluid within the device 800.

As shown in FIGS. 20-22, the device 800 includes at least a housing 810, a fluid reservoir 815, an actuator 840, and a volume indicator 850. The housing 810 includes a port 811 configured to convey a flow of fluid (e.g., bodily fluid) into and/or out of the fluid reservoir 815. In some embodiments, the housing 810 can be substantially similar in form and/or function to the housing 110 described above. In some embodiments, the housing 810 can be similar to a housing of a syringe and/or the like. As such, certain portions and/or aspects of the housing 810 are not described in further detail herein.

The actuator 840 can be any suitable shape, size, and/or configuration. In some embodiments, the actuator 840 can include at least a plunger 841 configured to be transitioned and/or moved within and/or relative to the fluid reservoir 815. In some embodiments, for example, the actuator 840 is similar in at least form and/or function to any of the actuators 40, 140, 240, 340, 440, 540, 640, and/or 740 described above. In other embodiments, the actuator 840 can be similar to an actuator of a syringe and/or the like. As such, certain portions and/or aspects of the actuator 840 are not described in further detail herein.

In the embodiment shown in FIGS. 20-22, the volume indicator 850 can include two indication members 851 configured to move along a corresponding track 848 (e.g., ridge, protrusion, path, and/or the like) disposed on, formed by, and/or otherwise extending from the plunger 841. In some embodiments, the indications members 851 can be configured to selectively engage the corresponding track 842 of the plunger 841. For example, in some embodiments, each track 842 can have a different shape and/or contour such that tracks 842 are brought into contact with the indication members 851 after a predetermined and/or desired amount of movement of the plunger 841. More particularly, in some embodiments, a first track 842 can be configured to engage and/or move a first indication member 851 in response to the plunger 841 being moved a first amount or distance, while the second track 842 does not engage the second indication member 851 (FIG. 21). In some embodiments, the movement and/or engagement of the first indication member 851 provides a user an indication that a first predetermined and/or known volume of bodily fluid is disposed in the fluid reservoir 815. In some instances, the user can continue to move the plunger 841 an additional amount (e.g., a second amount or distance), which in turn, can result in the second track 842 engaging and/or moving into contact with the second indication member 851 (FIG. 22). In this manner, moving the second indication member 851 can provide the user with an indication that a second predetermined and/or known volume of bodily fluid is disposed in the fluid reservoir 815.

Figure 23:
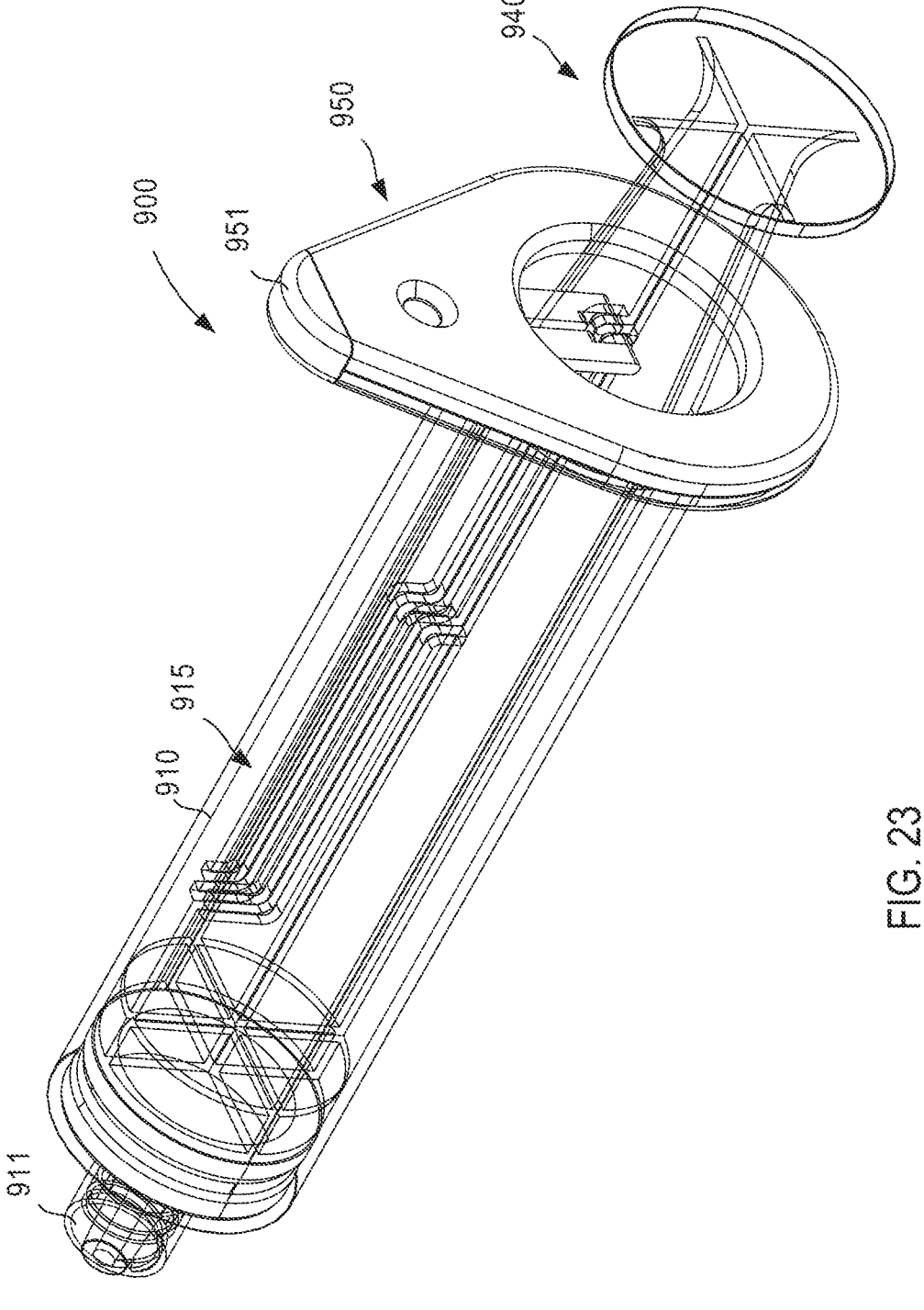
FIGS. 23-25 are each a perspective view of a bodily fluid collection and distribution device according to an embodiment, shown in a first state, a second state, and a third state, respectively.
Figure 24:
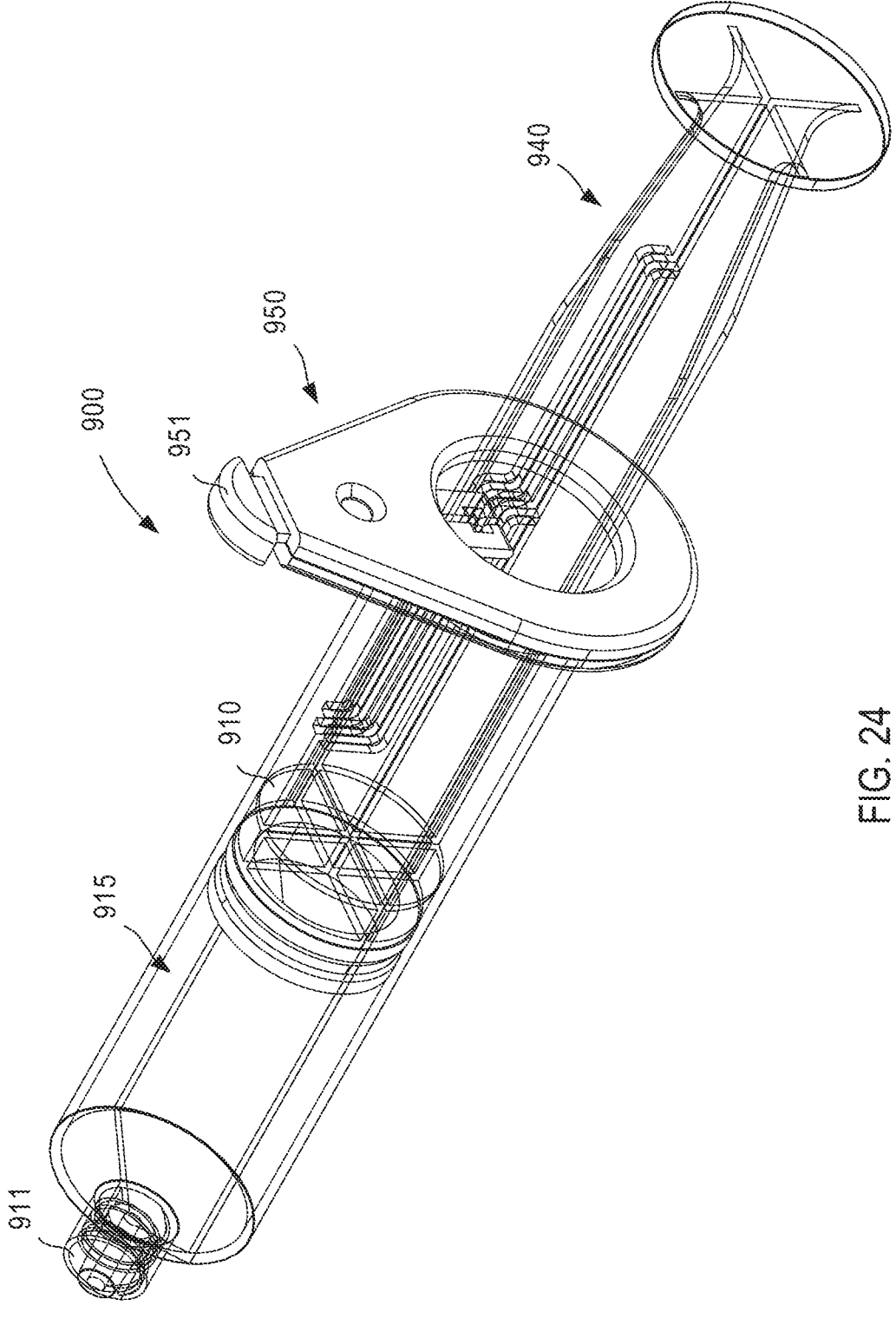
Figure 25:
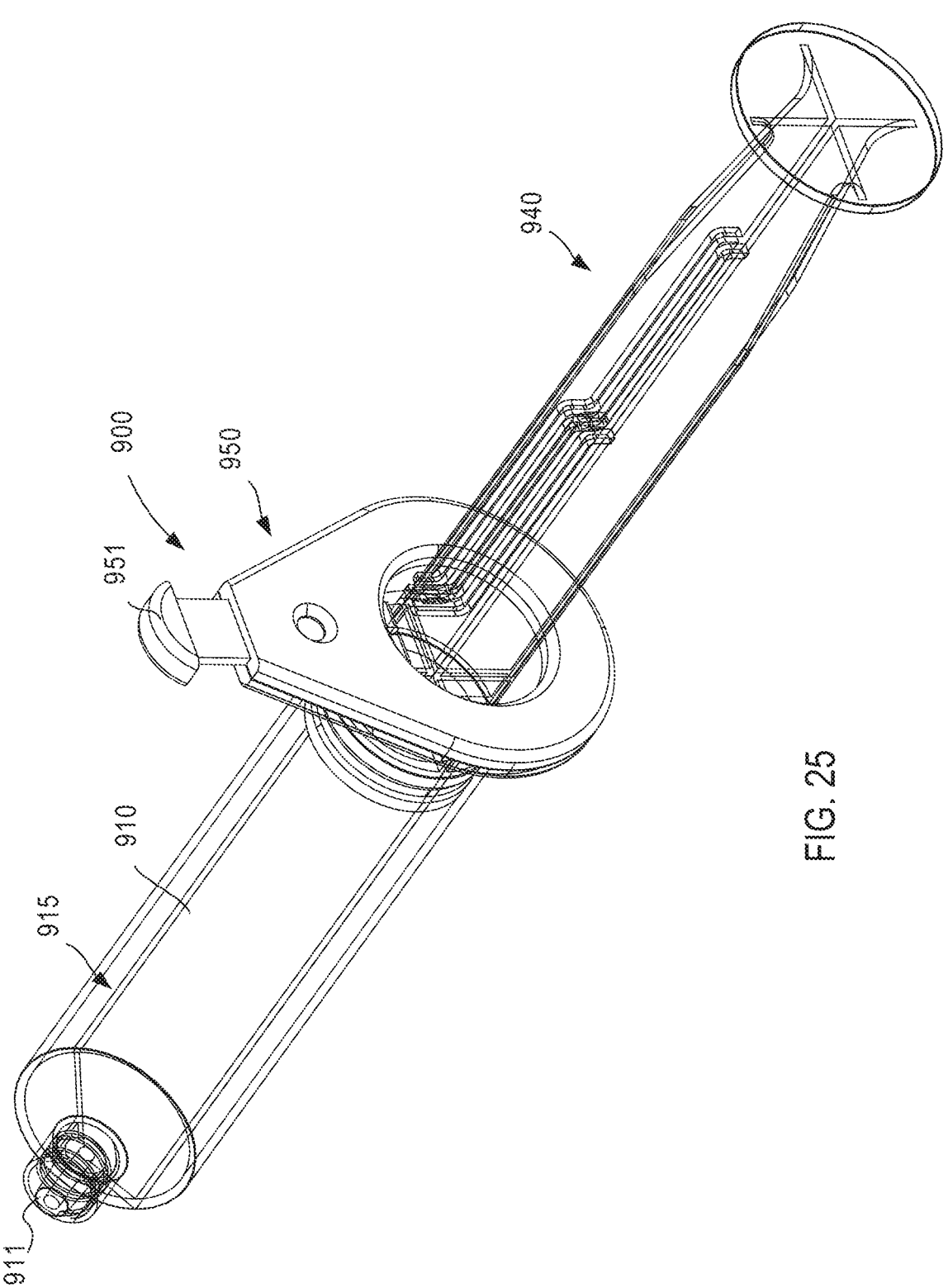

FIGS. 23-25 illustrate a bodily fluid collection and distribution device 900 according to another embodiment, shown in a first state, a second state, and a third state, respectively. The bodily fluid collection and distribution device 900 (also referred to herein as "device" 900) can be substantially similar in at least form and/or function to at least the devices 1, 100, 700, and/or 800 described above. The device 900 can differ, however, in the arrangement and/or configuration of a volume indicator while still being configured to, among other things, provide an indication of a volume of fluid (e.g., bodily fluid) within the device 900 and/or control, limit, and/or distribute at least a portion of the volume of the fluid within the device 900.

As shown in FIGS. 23-25, the device 900 includes at least a housing 910, a fluid reservoir 915, an actuator 940, and a volume indicator 950. The housing 910 includes a port 911 configured to convey a flow of fluid (e.g., bodily fluid) into and/or out of the fluid reservoir 915. In some embodiments, the housing 910 can be substantially similar in form and/or function to the housings 110, 710, and/or 810 described above. In some embodiments, the housing 910 can be similar to a housing of a syringe and/or the like. In addition, the actuator 940 can be similar in at least form and/or function to any of the actuators 40, 140, 240, 340, 440, 540, 640, 740, and/or 840 described above. In other embodiments, the actuator 940 can be similar to an actuator of a syringe and/or the like. As such, certain portions and/or aspects of the housing 910 and/or the actuator 940 are not described in further detail herein.

In the embodiment shown in FIGS. 23-25, the volume indicator 950 can include an indication members 951 configured to move along a portion of the actuator 940. In some embodiments, a portion of the actuator 940 can be configured to selectively engage the indication member 951 in response to the actuator 940 being moved a first amount or distance. More particularly, in some embodiments, the volume indicator 950 can be in a first state or position when the actuator 950 is in a first state or position, as shown in FIG. 23; the volume indicator 950 can be transitioned to a second state or position when the actuator 950 is placed in a second state or position, as shown in FIG. 24; and the volume indicator 950 can be transitioned to a third sate or position when the actuator 950 is placed in a third state or position, as shown in FIG. 25. In this manner, the volume indicator 950 can be configured to provide an indication to a user associated with and/or indicative of a volume of bodily fluid drawn into the fluid reservoir 915 in response to moving the actuator 940 a known or predetermined amount, as described above with reference to any of the devices 1, 100, 200, 300, 400, 500, 600, 700, and/or 800.

Figure 26:
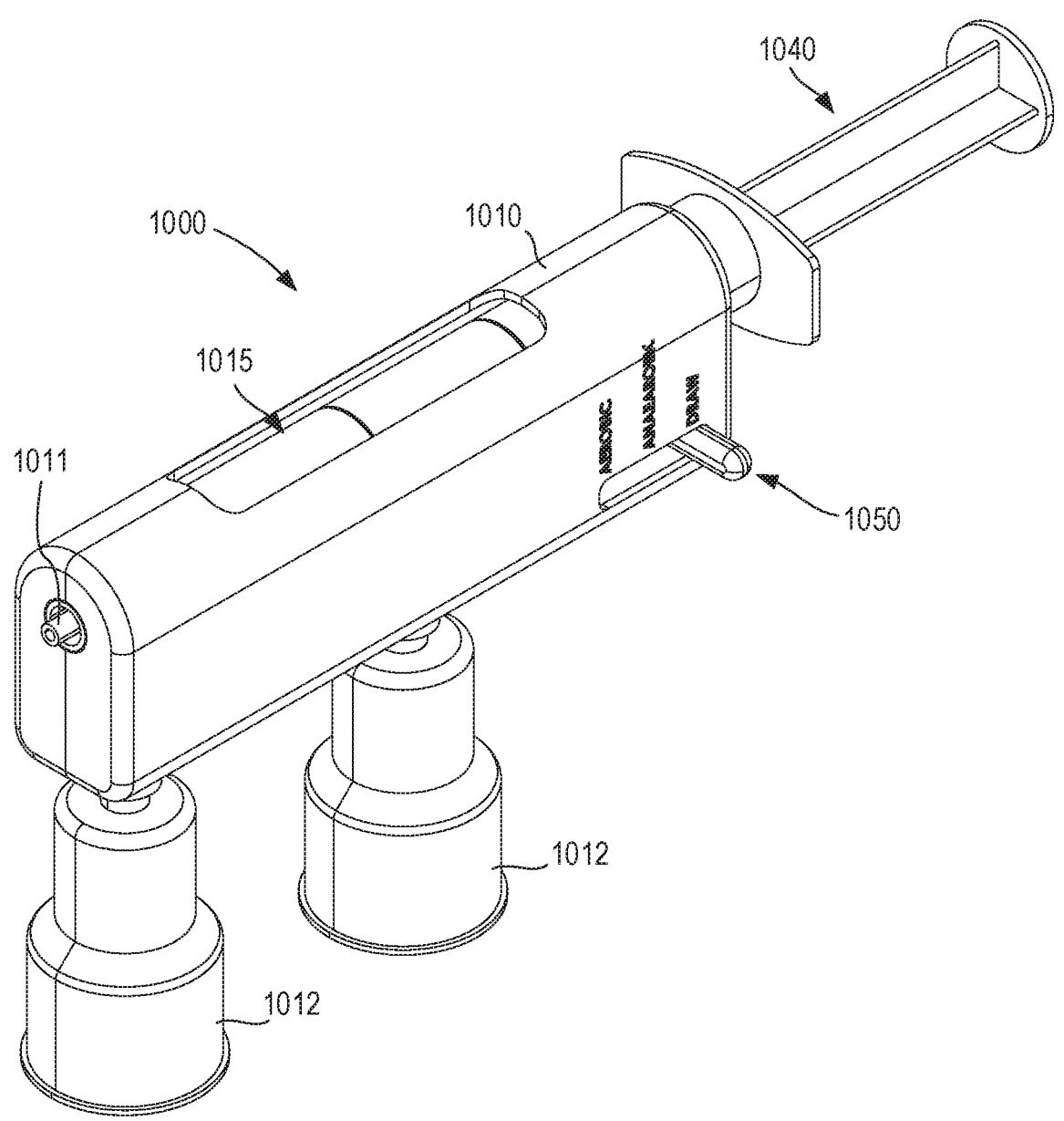
FIG. 26 is a perspective view of a bodily fluid collection and distribution device according to an embodiment.

For example, FIG. 26 illustrates a bodily fluid collection and distribution device 1000 according to an embodiment. The bodily fluid collection and distribution device 1000 (also referred to herein as "device" 1000) can be substantially similar in at least form and/or function to at least the devices 1, 100, 700, 800, and/or 900 described above. The device 1000 can differ, however, in the arrangement and/or configuration of a volume indicator while still being configured to, among other things, provide an indication of a volume of fluid (e.g., bodily fluid) within the device 1000 and/or control, limit, and/or distribute at least a portion of the volume of the fluid within the device 1000.

As shown in FIG. 26, the device 1000 includes at least a housing 1010, a fluid reservoir 1015, an actuator 1040, and a volume indicator 1050. The housing 1010 includes an inlet port 1011 configured to convey a flow of fluid (e.g., bodily fluid) into the fluid reservoir 1015 and at least one outlet port 1012 configured to convey a desired volume or portion of the bodily fluid disposed in the fluid reservoir 1015. In some embodiments, the housing 1010 can be substantially similar in form and/or function to the housings 110, 710, 810, and/or 910 described above. In some embodiments, the housing 1010 can be similar to a housing of a syringe and/or the like. In addition, the actuator 1040 can be similar in at least form and/or function to any of the actuators 40, 140, 240, 340, 440, 540, 640, 740, 840, and/or 940 described above. In other embodiments, the actuator 1040 can be similar to an actuator of a syringe and/or the like. As such, certain portions and/or aspects of the housing 1010 and/or the actuator 1040 are not described in further detail herein.

The volume indicator 1050 of the device 1000 shown in FIG. 26 can be substantially similar in at least function to the volume indicators 50, 150, 750, 850, and/or 950 of the devices 100, 700, 800, and/or 900, respectively. While the volume indicators 750, 850, and 950 are described above as including an indication member that is transitioned in response to movement of at least a portion of an actuator, the volume indicator 1050 shown in FIG. 26 can be and/or can include a switch or the like that can be transitioned between one or more states and/or configurations to control and/or distribute one or more volumes of bodily fluid drawn into the fluid reservoir 1015. For example, in some embodiments, the switch of the volume indicator 1050 can be in a first state and/or configuration in which the device 1000 is configured or enabled to a desired amount of bodily fluid into the fluid reservoir 1015. In some instances, after disposing the desired amount of bodily fluid into the fluid reservoir 1015, the user can transition the volume indicator 1050 to a second state and/or configuration in which a first known and/or predetermined volume of the bodily fluid can be conveyed and/or distributed into one or more collection devices. In some instances, the second state can enable and/or allow a user to convey and/or distribute a volume of bodily fluid associated with and/or otherwise suitable for aerobic culture testing (e.g., via one of the outlets 1012) or for anaerobic culture testing (e.g., via the other outlet 1012). As such, the device 1000 can be configured to provide an indication associated with the volume disposed in the fluid reservoir 1015 and/or to convey and/or distribute a known and/or predetermined amount of bodily fluid into one or more collection devices based at least in part on a type of testing and/or analysis to be performed.

Figure 27:
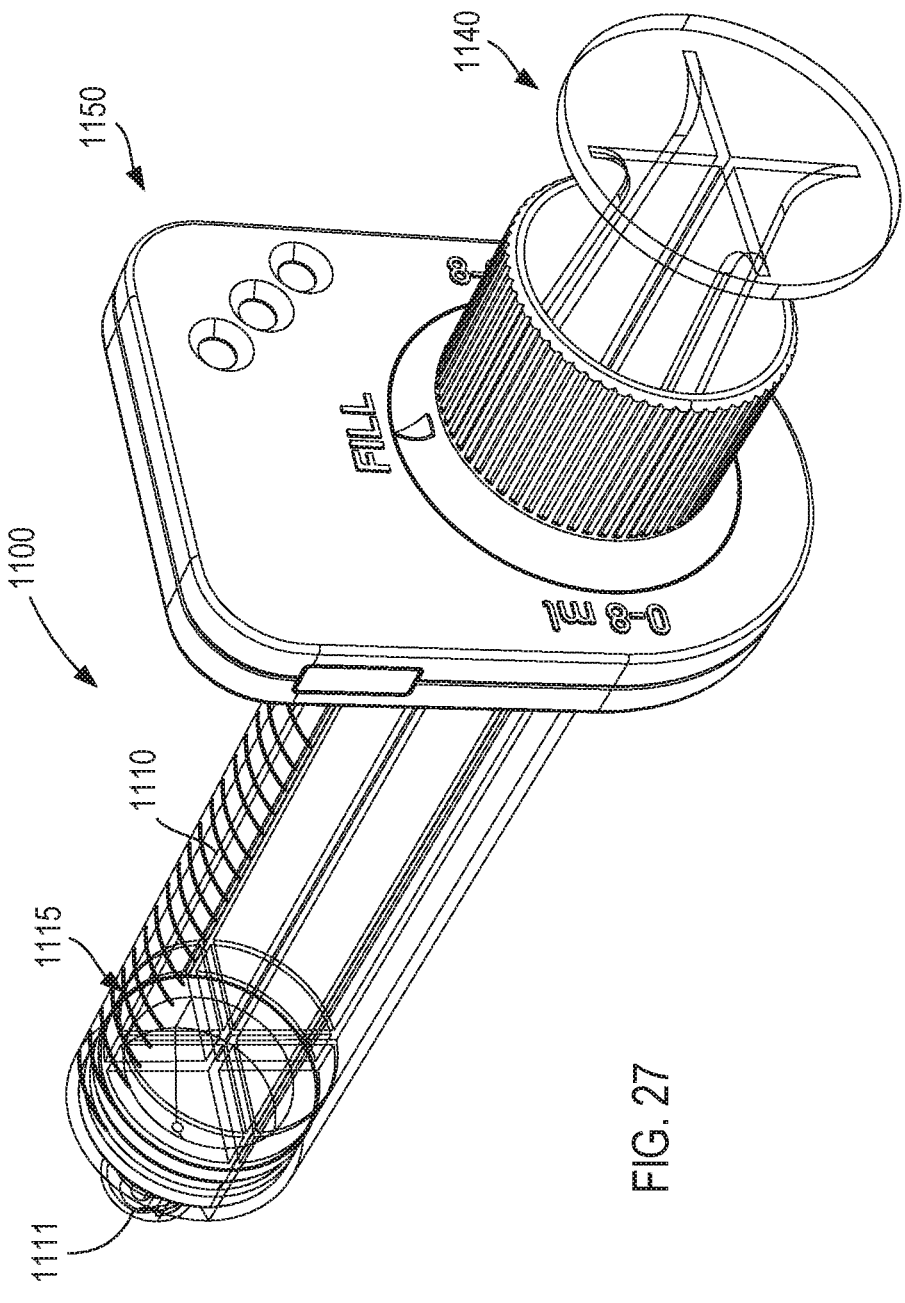
FIGS. 27 and 28 are each a perspective view of a bodily fluid collection and distribution device according to an embodiment, shown in a first state and a second state, respectively.
Figure 28:
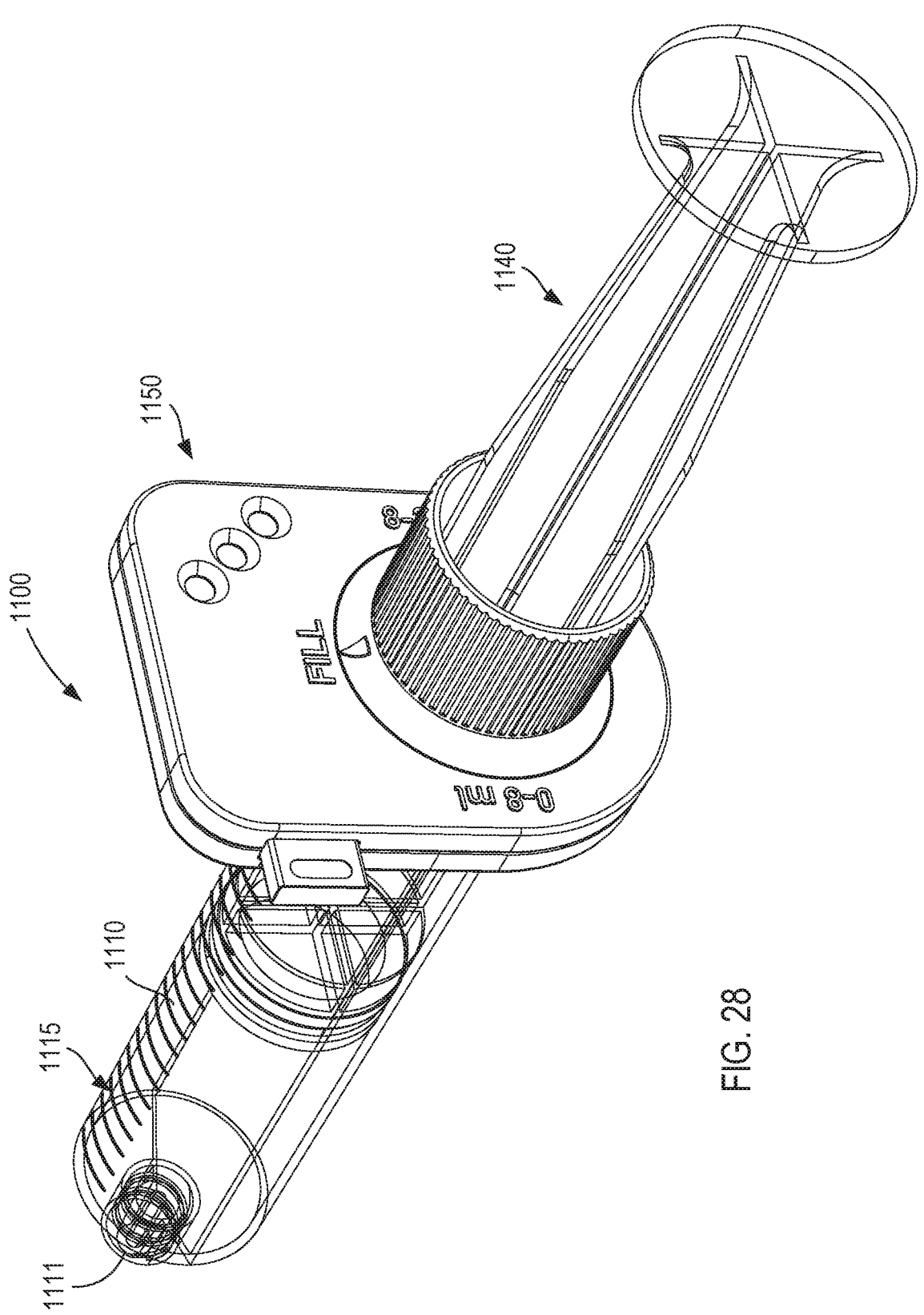

For example, FIGS. 27 and 28 illustrate a bodily fluid collection and distribution device 1100 according to an embodiment, shown in a first state and a second state, respectively. The bodily fluid collection and distribution device 1100 (also referred to herein as "device" 1100) can be substantially similar in at least form and/or function to at least the devices 1, 100, 700, 800, 900, and/or 1000 described above. The device 1100 can differ, however, in the arrangement and/or configuration of a volume indicator while still being configured to, among other things, provide an indication of a volume of fluid (e.g., bodily fluid) within the device 1100 and/or control, limit, and/or distribute at least a portion of the volume of the fluid within the device 1100.

As shown in FIGS. 27 and 28, the device 1100 includes at least a housing 1110, a fluid reservoir 1115, an actuator 1140, and a volume indicator 1150. The housing 1110 includes a port 1111 configured to convey a flow of fluid (e.g., bodily fluid) into and/or out of the fluid reservoir 1115. In some embodiments, the housing 1110 can be substantially similar in form and/or function to the housings 10, 110, 710, 810, 910, and/or 1010 described above. In some embodiments, the housing 1110 can be similar to a housing of a syringe and/or the like. In addition, the actuator 1140 can be similar in at least form and/or function to any of the actuators 40, 140, 240, 340, 440, 540, 640, 740, 840, 940, and/or 1040 described above. In other embodiments, the actuator 1140 can be similar to an actuator of a syringe and/or the like. As such, certain portions and/or aspects of the housing 1110 and/or the actuator 1140 are not described in further detail herein.

The volume indicator 1150 of the device 1100 shown in FIGS. 27 and 28 can be substantially similar in at least function to the volume indicators 50, 150, 750, 850, 950, and/or 1050 of the devices 1, 100, 700, 800, 900, and/or 1000, respectively. For example, while the volume indicator 1050 is shown as a switch, in the embodiment shown in FIGS. 27 and 28, the volume indicator 1150 is arranged and/or configured as a dial or the like that can be transitioned between one or more states and/or configurations to control and/or distribute one or more volumes of bodily fluid drawn into the fluid reservoir 1115. As such, the volume indicator 1150 can function in a manner similar to the volume indicator 1050 shown and described above with reference to FIG. 26.

Figure 29:
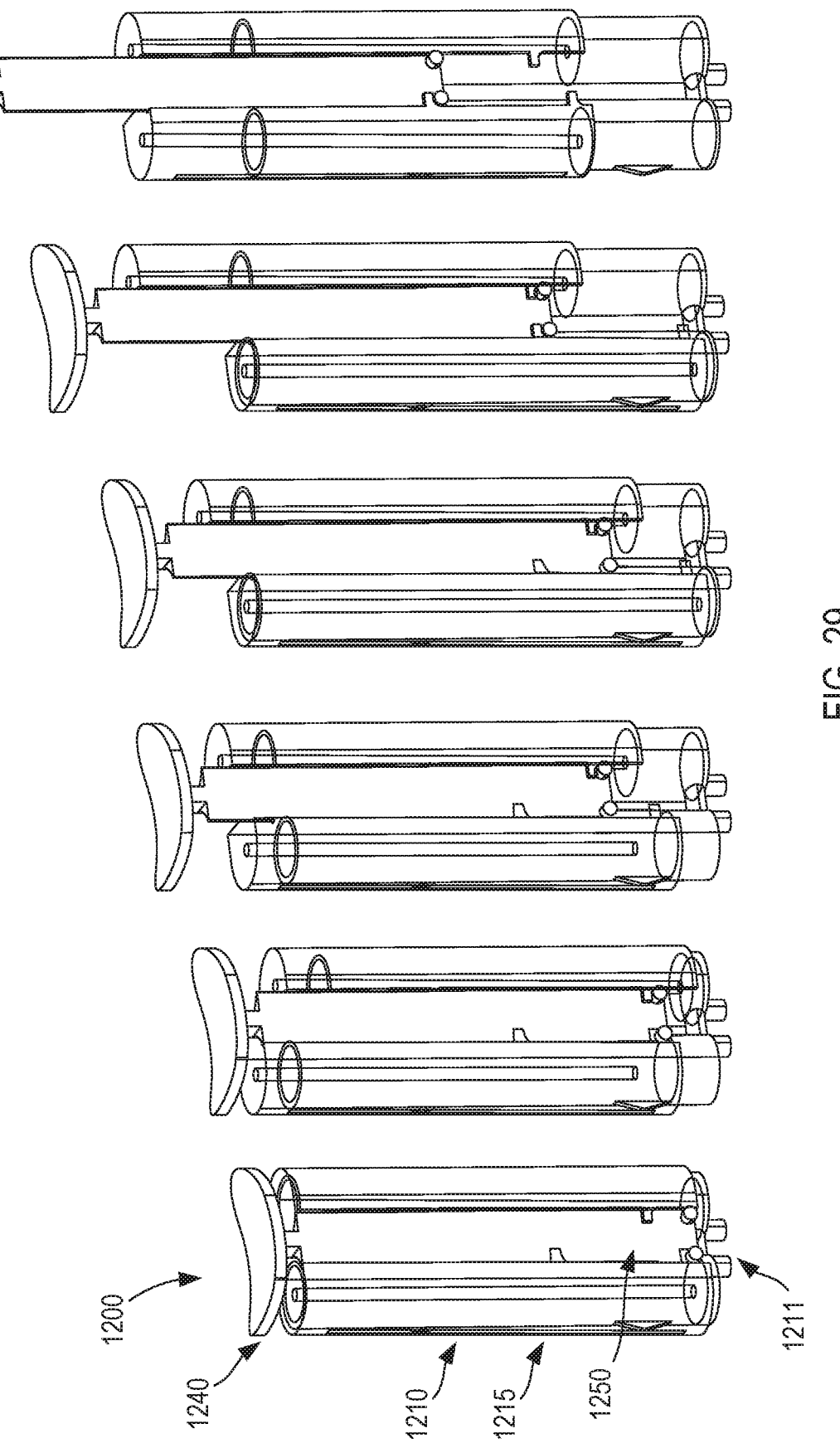
FIG. 29 is a perspective view of a bodily fluid collection and distribution device according to an embodiment, shown, for example, in various states.
Figure 30:
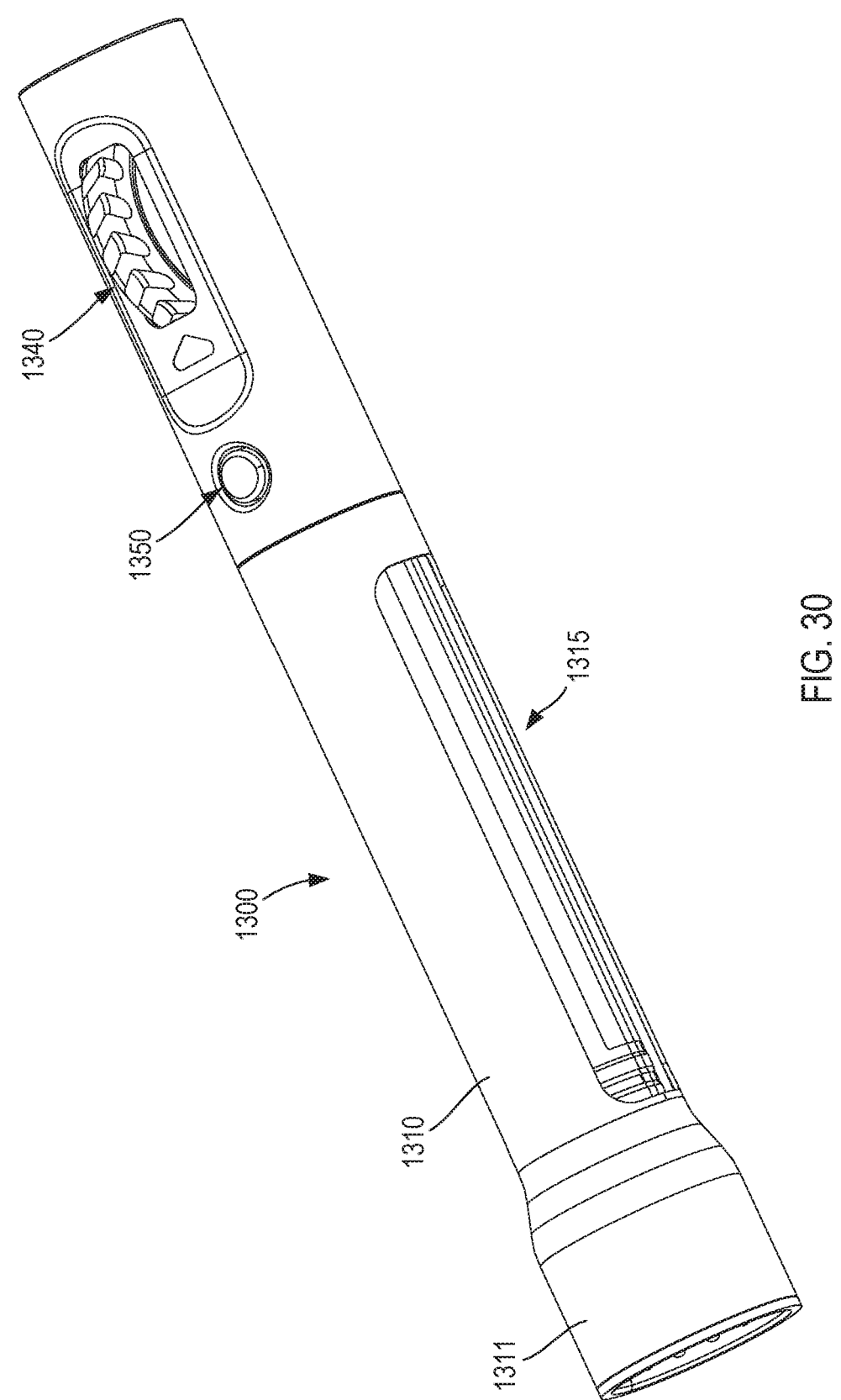
FIGS. 30 and 31 are a front and a rear perspective view, respectively, of a bodily fluid collection and distribution device according to an embodiment.
Figure 31:
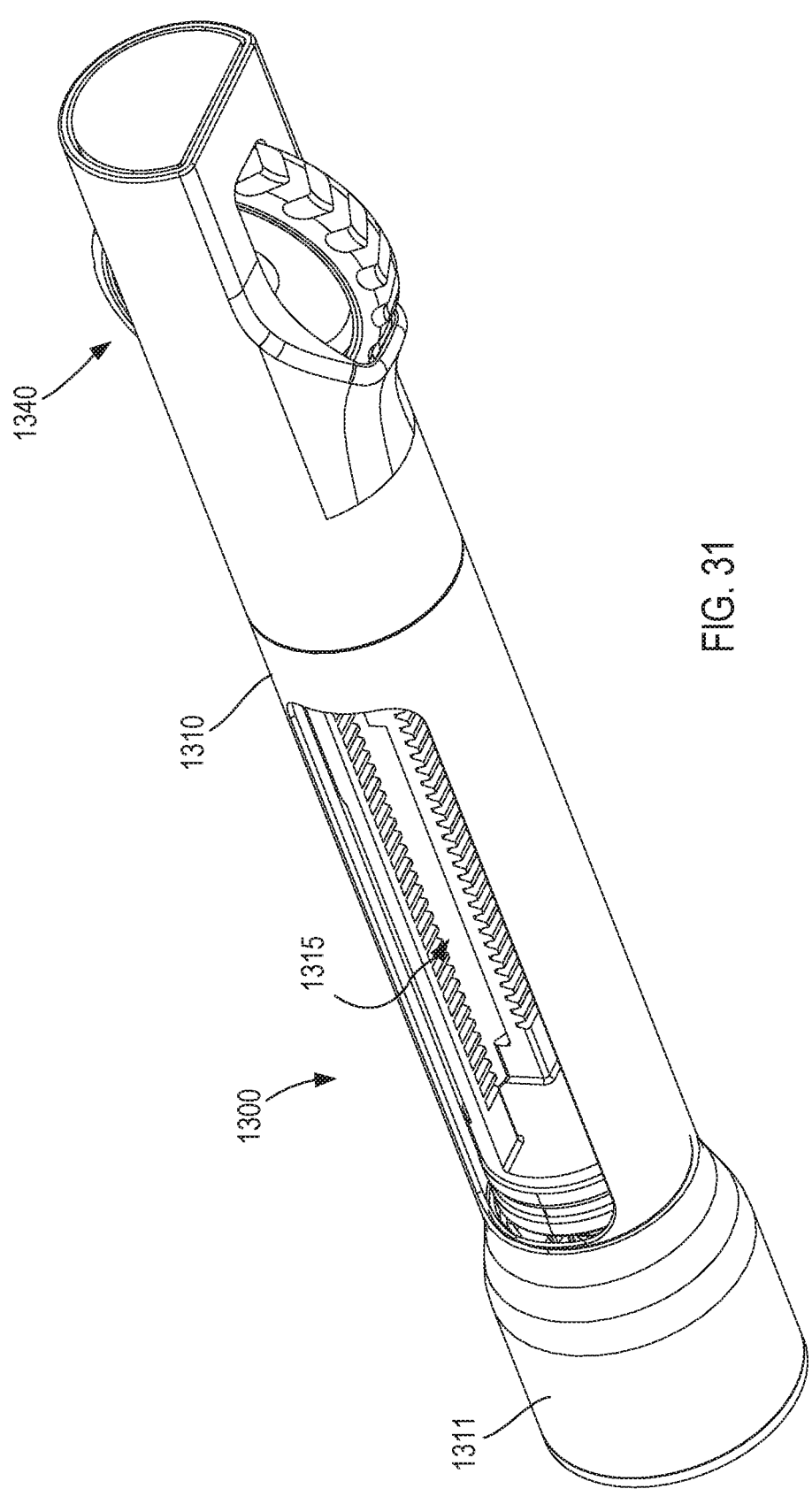

While the devices 1, 100, 200, 300, 400, 500, 600, 700, 800, 900, 1000, and/or 1100 are shown and described above as including a single fluid reservoir, in other embodiments, a bodily fluid collection and distribution device can include any number of fluid reservoirs configured to receive a volume of bodily fluid based at least in part on one or more tests intended to be performed on the bodily fluid. For example, FIG. 29 illustrates a bodily fluid collection and distribution device 1200 according to an embodiment. The bodily fluid collection and distribution device 1200 (also referred to herein as "device" 1200) can be substantially similar in at least form and/or function to any of the devices described above. The device 1200 can differ, however, by including at least two fluid reservoirs, each of which is configured to receive a predetermined and/or desired volume of bodily fluid.

As shown in FIG. 29, the device 1200 includes at least a housing 1210, a fluid reservoir 1215, an actuator 1240, and a volume indicator 1250. The housing 1210 includes a port 1211 configured to convey a flow of fluid (e.g., bodily fluid) into and/or out of the fluid reservoir 1215. In some embodiments, the housing 1210 can be substantially similar in form and/or function to any of the housings described above. In some embodiments, the housing 1210 can be similar to a housing of a syringe and/or the like. In addition, the actuator 1240 can be similar in at least form and/or function to any of the actuators described above. In other embodiments, the actuator 1240 can be similar to an actuator of a syringe and/or the like. As such, certain portions and/or aspects of the housing 1210 and/or the actuator 1240 are not described in further detail herein.

As shown in FIG. 29, the actuator 1240 can include a first portion disposed in and/or configured to engage a first fluid reservoir and a second portion disposed in and/or configured to engage a second fluid reservoir. Moreover, the volume indicator 1250 of the device 1200 can be configured to selectively engage one or more portions of the actuator 1240 to control, limit, and/or selectively enable the first portion of the actuator 1240 or the second portion of the actuator 1240 to be moved within and/or relative to the corresponding fluid reservoir 1215. As such, the volume indicator 1250 can selectively control a flow of a predetermined and/or known volume of bodily fluid into one or more of the fluid reservoirs 1215. In some embodiments, the volume indicator 1250 can similarly control and/or distribute a desired portion of the bodily fluid into any number of collection devices. In some instances, the volume indicator 1250 can be configured to distribute a predetermined volume of bodily fluid into a collection device based at least in part on a test or analysis to be performed on the bodily fluid.

While the inlet adapter 120 of the bodily fluid collection and distribution device 100 is described above as including and/or being coupled to a device configured to receive, divert, and/or sequester an initial volume of bodily fluid from a bodily fluid source, in other embodiments, a bodily fluid collection and distribution device can include a diverter having any suitable configuration and/or arrangement without substantially departing from the function of the diversion devices described above. For example, FIGS. 30-34 illustrate a bodily fluid collection and distribution device 1300 according to an embodiment. The bodily fluid collection and distribution device 1300 (also referred to herein as "device" 1300) can be substantially similar in at least form and/or function to at least the device 1 described above with reference to FIGS. 1A-1C and/or the device 100 described above with reference to FIGS. 2-8. The device 1300 can differ, however, by including a diverter and/or a diversion device or mechanism within a housing of the device 1300 and/or otherwise integrated into the device 1300.

As shown in FIG. 30-34, the device 1300 includes at least a housing 1310, a fluid reservoir 1315, an inlet adapter 1320, an actuator 1340, a volume indicator 1350, and a diverter 1370. The housing 1310 includes a port 1311 configured to convey a flow of fluid (e.g., bodily fluid) into and/or out of the fluid reservoir 1315. In some embodiments, the housing 1310 can be substantially similar in form and/or function to any of the housings described above. In some embodiments, the inlet adapter 1320 can be substantially similar in form and/or function to the inlet adapter 120 described above with reference to FIGS. 2-8. In some embodiments, the actuator 1340 can be similar in at least form and/or function to any of the actuators described above. In some embodiments, the volume indicator 1350 can be substantially similar in form and/or function to, for example, the volume indicator 150 described above with reference to FIGS. 2-8. As such, certain portions and/or aspects of the housing 1310, the inlet adapter 1320, the actuator 1340, and/or the volume indicator 1350 are not described in further detail herein.

Figures 32, 33, 34:
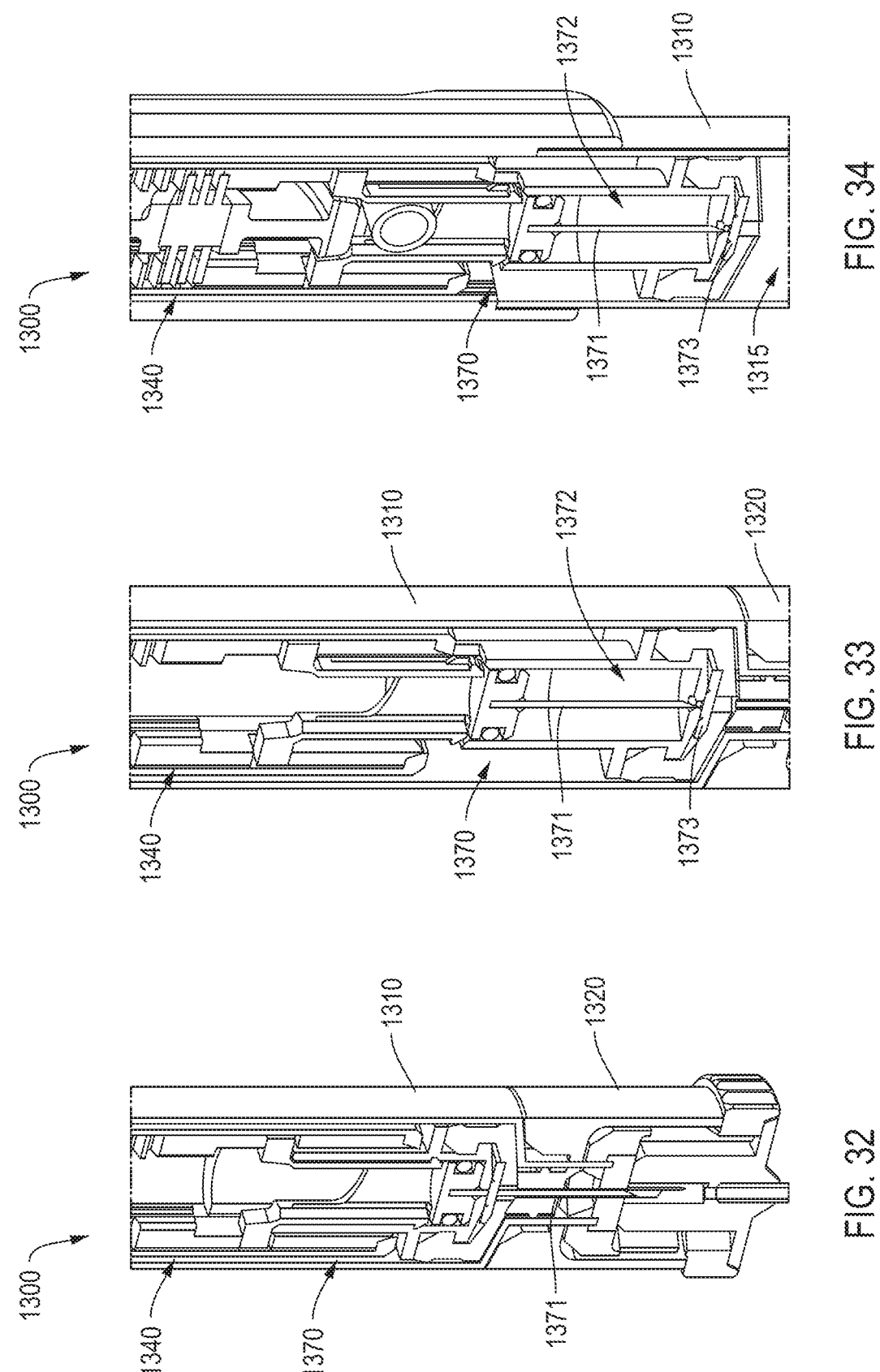
FIGS. 32-34 are cross-sectional views of the bodily fluid collection and distribution device of FIG. 30, shown in a first state, a second state, and a third state, respectively.

As described above, the diverter 1370 can be configured to (1) receive an initial volume of bodily fluid withdrawn from a bodily fluid source (e.g., the patient) and (2) sequester the initial volume of bodily fluid such that subsequent volumes of bodily fluid drawn into the fluid reservoir 1315 are substantially free from contaminants otherwise included in the initial volume. The diverter 1370 of the device 1300 can be any suitable shape, size, and/or configuration. As shown in FIGS. 32-34, the diverter 1370 is disposed in the housing 1310 and more particularly, within a portion of the actuator 1340. In some embodiments, the diverter 1370 can include a pre-sample reservoir 1372 configured to receive a plunger or seal included in and/or coupled to the actuator 1340. The diverter 1370 further includes a needle 1371 or other conduit configured to pierce and/or at least temporarily extend through a seal 1373 disposed within a plunger of the actuator 1340.

The diverter 1370 is configured to transition between a first state and a second state in response the actuator 1340 being transitioned and/or moved relative to the housing 1310. For example, the diverter 1370 can be in the first state when the actuator 1340 is in a first or distal position within the fluid reservoir 1315, as shown in FIG. 32. More particularly, when the diverter 1370 is in the first state, the needle 1371 can extend through the seal 1373 to place the pre-sample reservoir 1372 of the diverter 1370 in fluid communication with the inlet adapter 1320. As such, when a user manipulates the device 1300 to withdraw bodily fluid from a bodily fluid source (e.g., a patient), the pre-sample reservoir 1372 can receive the initial volume of bodily fluid.

As shown in FIG. 33, the user can manipulate the actuator 1340 to transition the diverter 1370 from the first state to the second state. In some embodiments, manipulating the actuator 1340 can include, for example, moving a portion or plunger of the 1340 within the pre-sample reservoir 1372, which in turn, results in a negative pressure differential and/or suction force within the pre-sample reservoir 1372. In some embodiments, the needle 1371 can also be withdrawn from the seal 1373 and disposed in the pre-sample reservoir 1372. As such, the initial volume of bodily fluid can be transferred through the inlet adapter 1320 and the seal 1373, and into the pre-sample reservoir 1372, as shown in FIG. 33. In some embodiments, after receiving the initial volume of bodily fluid in the pre-sample reservoir 1372, the diverter 1370 can be configured to sequester the initial volume therein. Once sequestered, the user can continue to manipulate the actuator 1340 to draw a subsequent volume of bodily fluid into the fluid reservoir 1315 (FIG. 34), as described in detail above with reference to the devices 1 and/or 100. Thus, the device 1300 can perform in a manner substantially similar to the devices 1 and/or 100. Moreover, in some instances, the sequestered initial volume of bodily fluid can be conveyed out of the fluid reservoir 1372 of the diverter 1370 for reinfusion into the body or for any suitable testing not susceptible to false results due to contamination.

The devices described herein are configured to limit, control, meter, and/or modulate a rate at which bodily fluid is drawn into a fluid reservoir of the device. In some instances, limiting, controlling, and/or modulating the rate of fluid transfer similarly limits, controls, meter, and/or modulates a magnitude of a vacuum within a fluid reservoir and/or a volume displaced by an actuator or plunger thereof.

Figure 35:
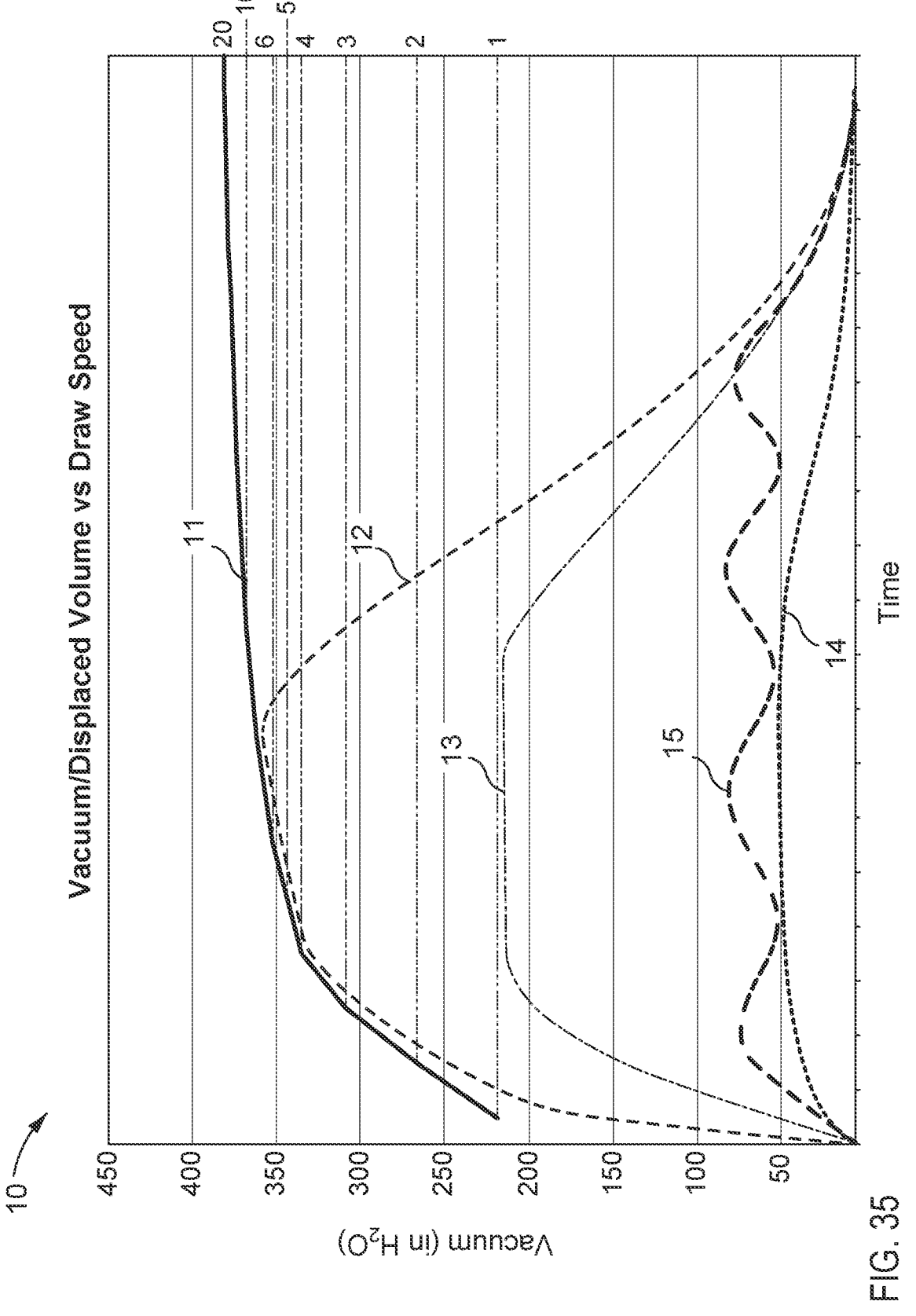
FIG. 35 is a graph illustrating a relationship between a vacuum and/or displaced volume and a draw speed of drawing bodily fluid into a reservoir using various methods.

For example, FIG. 35 is a graph 1400 illustrating a relationship and/or an anticipated, calculated, and/or theoretical relationship between a vacuum and/or displaced volume and a draw speed of drawing bodily fluid into a reservoir using various methods such as any of those described herein. More particularly, the graph 1400 illustrates a vacuum and/or displaced volume as a function of draw speed (e.g., speed of moving an actuator) with a fixed fluid flow, inlet size, and fluid viscosity. As shown, line 1401 illustrates a maximum vacuum using 20 mL displacement with a closed volume. Line 1402 illustrates a vacuum resulting from a "fast draw" in which a 20 mL displacement is performed quickly and held, allowing the bodily fluid to flow into the displaced volume. Line 1403 illustrates a vacuum resulting from a "normal draw" in which a plunger is maintained approximately 1.0 mL ahead of the fluid flow until 20 mL of displacement. Line 1404 illustrates a vacuum resulting from a "slow draw" in which a plunger is moved at a rate substantially equal to a fill rate of the bodily fluid until 20 mL of displacement. Line 1405 illustrates a vacuum resulting from a maximum rate of displacement using any of the devices described herein. As shown by line 1405 in graph 1400, the devices described herein control, limit, meter, and/or modulate an amount of vacuum and/or a rate of displacement within the fluid reservoirs even if actuated as quickly as possible.

Figure 36:
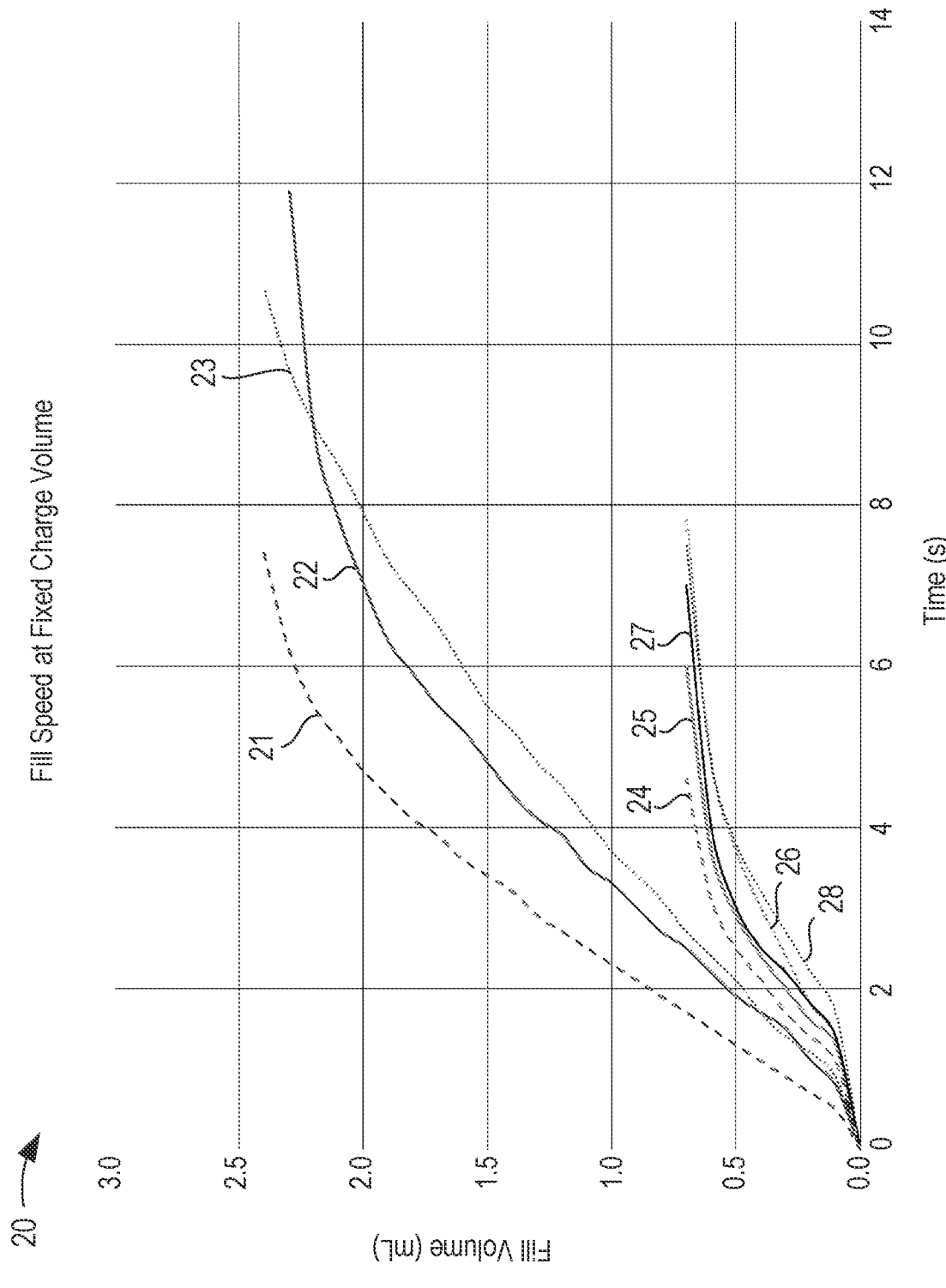
FIG. 36 is a graph illustrating a rate of filling a reservoir having a fixed charged volume using various methods.

FIG. 36 is a graph 1500 illustrating a rate of filling a reservoir having a fixed charged volume using various methods. More particularly, lines 1501, 1502, and 1503 illustrate a fill speed of a fluid having a different viscosities using the same method of procurement (e.g., using a diversion and collection device) with 3.0 mL of displacement. For example, line 1501 illustrates a fill speed of a fluid that simulates blood (e.g., VATA or the like); line 1502 illustrates a fill speed of a fluid having a viscosity of about 4.0 centipoise (cP); and line 1503 illustrates a fill speed of a fluid having a viscosity of about 8.0 cP. Lines 1504, 1505, and 1506 illustrate a fill speed of VATA, the 4.0 cP fluid, and the 8.0 cP fluid, respectively, using a 1.0 mL syringe and 1.0 mL displacement. Lines 1507 and 1508 illustrate a fill speed of the 4.0 cP fluid and the 8.0 cP fluid, respectively, using a 3.0 mL syringe and 1.0 mL displacement.

Figure 37:
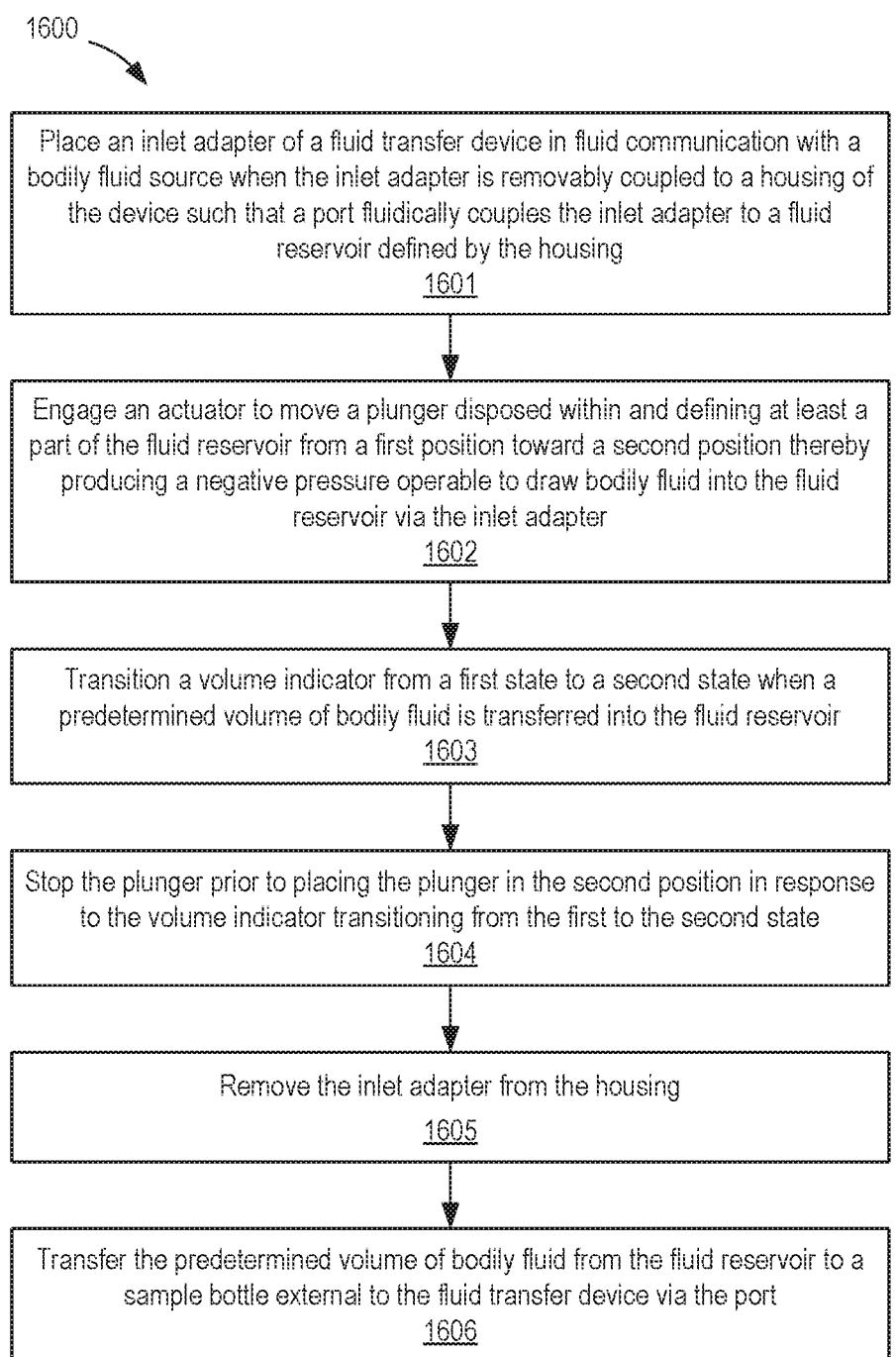
FIG. 37 is a flowchart illustrating a method of using a bodily fluid transfer and distribution device according to an embodiment.

FIG. 37 is a flowchart illustrating a method 1600 of using a fluid transfer and distribution device according to an embodiment. The fluid transfer and distribution device (also referred to herein as device) can be similar to and/or substantially the same as any of the devices (or a combination of any of the devices) described herein. For example, the device can include a housing, a fluid reservoir, an inlet adapter, an actuator, and a volume indicator, as described above with reference to, for example, the device 1 shown in FIGS. 1A-1C.

The method 1600 includes placing the inlet adapter of the fluid transfer device in fluid communication with a bodily fluid source when the inlet adapter is removably coupled to the housing such that a port of the housing fluidically couples the inlet adapter to the fluid reservoir defined by the housing, at 1601. The inlet adapter can be any suitable member, mechanism, device, etc., such as any of those described herein. For example, in some implementations, the inlet adapter can be substantially similar in form and/or function as the inlet adapter 20 described above with reference to FIGS. 1A-1C. In some embodiments, the inlet adapter can be and/or can include a needle, catheter, cannula, conduit, and/or the like that can be in fluid communication with a bodily fluid source (e.g., a patient). The inlet adapter can be configured to removably couple to the housing such that fluid communication is established between the inlet adapter and the fluid reservoir via the port.

The actuator is engaged to move a plunger disposed within and defining at least a part of the fluid reservoir from a first position toward a second position such that the movement of the plunger produces a negative pressure operable to draw bodily fluid into the fluid reservoir via the inlet adapter, at 1602. The actuator can be any suitable member, mechanism, device, etc., such as any of those described herein. For example, in some implementations, the actuator can be substantially similar in form and/or function as the actuator 40 described above with reference to FIGS. 1A-1C. In this manner, the actuator can be manipulated to move the plunger within the housing, which in turn, increases a volume of the fluid reservoir and draws a volume of bodily fluid into the fluid reservoir as the plunger is moved from the first position toward the second position. As described in detail above, in some implementations, the actuator can be configured to control, meter, and/or modulate a rate at which bodily fluid is transferred into the fluid reservoir, which in turn, can increase a likelihood of the user drawing a desired and accurate volume of bodily fluid into the fluid reservoir, as described above, for example, with reference to the device 1.

A volume indicator is transitioned from a first state to a second state when a predetermined volume of bodily fluid is transferred into the fluid reservoir, at 1603. The volume indicator can be any suitable member, mechanism, device, etc., such as any of those described herein. For example, in some implementations, the volume indicator can be substantially similar in form and/or function as the volume indicator 50 described above with reference to FIGS. 1A-1C. In some implementations, the predetermined volume of bodily fluid can be a recommended and/or desired volume of bodily fluid for use in testing the bodily fluid. For example, in some instances, the predetermined volume of bodily fluid can be 10.0 mL. As described above, the volume indicator can be configured to transition from the first state to the second state automatically when the predetermined volume of bodily fluid is in the fluid reservoir.

The plunger is stopped prior to the plunger being moved to (or placed in) the second position in response to the transitioning of the volume indicator from the first state to the second state, at 1604. For example, in some implementations, when the volume indicator is in the second state, a portion of the volume indicator can directly or indirectly block, limit, and/or substantially prevent further transitioning of the actuator (e.g., further movement of the plunger toward the second position). In such embodiments, the predetermined volume of bodily fluid is less than a volume of the fluid reservoir when the plunger is in the second position. As such, the user can choose to continue transferring bodily fluid into the fluid reservoir, for example, by transitioning the volume indicator from its second state (e.g., toward the first state or to a third state different from the first and second states).

The inlet adapter is removed from the housing, at 1605. For example, a user can transfer a desired volume of bodily fluid (e.g., the predetermined volume of fluid) into the fluid reservoir and once disposed therein, the user can remove and/or decouple the inlet adapter from the housing, as described above with reference to the device 1, 100, 200, and/or any of the other devices described herein. In some implementations, removing the inlet adapter from the housing can allow a user to access the port of the housing, which in turn, can allow the user to transfer at least a portion of the bodily fluid in the fluid reservoir into one or more external fluid reservoirs. In some implementations, the inlet adapter can be configured to divert an initial volume of bodily fluid (e.g., in a pre-sample reservoir), which is sequestered in the inlet adapter when the inlet adapter is removed from the housing. In such instances, the inlet adapter (and the initial volume contained therein) can be discarded. In other instances, the initial volume of bodily fluid sequestered in the inlet adapter can be used in testing that has a relatively low sensitivity to contamination, can be reinfused into the patient, and/or can be used for any other suitable purpose.

The predetermined volume of bodily fluid is transferred from the fluid reservoir to a sample bottle external to the fluid transfer device via the port, at 1606. For example, in some instances, the user can couple the port to any suitable collection or sample reservoir such as, for example, a culture bottle (and/or any collection device described herein). Accordingly, the port of the housing can be used to transfer fluid into the fluid reservoir (e.g., acting as an inlet port) and to transfer fluid out of the fluid reservoir (e.g., acting as an outlet port). For example, in some instances, the user can engage the actuator to move the plunger toward the first position (e.g., in a direction opposite to the direction the plunger was moved when being moved from the first position toward the second position), which in turn, can expel the predetermined volume of bodily fluid from the fluid reservoir into the external sample bottle via the port. In other instances, the external sample bottle can be evacuated and/or can define a negative pressure that can be operable in drawing the predetermined volume of bodily fluid into the external sample bottle. In some instances, the user can transition the volume indicator from its second state prior to transferring the predetermined volume of bodily fluid into the external sample bottle. In other instances, the user need not transition the volume indicator from its second state.

The various embodiments of the bodily fluid collection devices described herein can allow the collection of two (or more) sets of bodily fluids (e.g., blood) samples from a single venipuncture. The current standard of care dictates that certain tests (e.g. blood cultures) be conducted with samples procured from distinct, separate bodily fluid access points (e.g. via two separate venipunctures, via a catheter+a venipuncture and/or any combination thereof). Embodiments described herein can facilitate the procurement of multiple samples for specific diagnostic testing (e.g. blood culture test) from a single bodily fluid access point (e.g. venipuncture), which can reduce the annual number of venipunctures required for procurement of these samples by a factor of two. This benefits both patients and health care practitioners alike. A reduction in the number of venipunctures (and/or other bodily fluid access procedures) can significantly reduce the risk of needle stick injury to heath care practitioners and reduce patient associated complications which result from these procedures (e.g. hematoma, thrombosis, phlebitis, infection, etc.).

Additionally, reducing the number of bodily fluid access procedures (e.g. venipunctures) reduces the utilization of supplies, labor, and waste associated with these procedures. The decreased costs realized by the healthcare system are material and represent an opportunity to drive increasingly more efficient consumption of resources as well as enhance patient outcomes due to improved sample integrity. The improved sample integrity can result in increased accuracy in diagnosing patients, which in turn, can facilitate the development and implementation of treatment plan(s). The bodily fluid collection devices also significantly reduce the occurrence of false-positives from post-collection analysis. The bodily fluid collection devices described herein can also streamline the bodily fluid collection process and reduce the number of manual steps and "touch points", thereby decreasing opportunities for external contamination. The devices described herein can also minimize the risk for needle stick injuries and infection for the lab technicians and/or phlebotomists.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features, concepts, and/or combinations of components, other embodiments are possible having any combination or sub-combination of any features, concepts, and/or components from any of the embodiments described herein. Moreover, any of the features, concepts, and/or components from any of the embodiments described herein can be incorporated into any suitable known device. For example, any of the features, concepts, and/or components, and/or any combination thereof can be incorporated into a known syringe and/or any other suitable fluid collection device.

The specific configurations of the various components can also be varied. For example, the size and specific shape of the various components can be different from the embodiments shown, while still providing the functions as described herein. More specifically, the size and shape of the various components can be specifically selected for a desired rate and/or volume of bodily fluid flow into a fluid reservoir. For example, the perimeter, the diameter, and/or the cross-sectional area of any of the fluid flow paths described herein can be designed and/or specifically, selected to accommodate a flow or translocation of fluids (e.g., bodily fluids), gases (e.g., air), or any suitable combination thereof at a desired flow rate. In other words, the components of the fluid control devices described herein, including those components built separately and later affixed together, can be selected individually or together to satisfy desired sample procurement criteria such as, for example, a magnitude of pressure differentials, a desired flow rate of bodily fluid through portions of the device, the ability to modulate pressures and/or flow rates, and/or the like. Likewise, the size and/or shape of the various components can be specifically selected for a desired or intended usage. For example, in some embodiments, devices such as those described herein can be configured for use with or on seemingly healthy adult patients. In such embodiments, the device can include a sequestration chamber that has a first volume (e.g., about 0.5 ml to about 5.0 ml). In other embodiments, a device such as those described herein can be configured for use with or on, for example, very sick patients and/or pediatric patients. In such embodiments, the device can include a sequestration chamber that has a second volume that is less than the first volume (e.g., less than about 0.5 ml). Thus, size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified and that such modifications are in accordance with the variations of the invention. Additionally, certain events and/or procedures may be performed concurrently in a parallel process when possible, as well as performed sequentially as described above. Certain steps may be partially completed or may be omitted before proceeding to subsequent steps.

What is claimed:

1. An apparatus, comprising:
a housing defining a fluid reservoir and including a port in fluid communication with the fluid reservoir;
an inlet adapter removably coupleable to the housing, the inlet adapter including a needle configured to place the port in fluid communication with a bodily fluid source when the inlet adapter is coupled to the housing;
an actuator including a plunger at least partially disposed within the housing and defining at least a part of the fluid reservoir, a first portion of the actuator configured to be engaged by a user to move the plunger within the housing from a first position in which the fluid reservoir has a first volume, to a second position in which the fluid reservoir has a second volume greater than the first volume, the increase in volume operable to draw bodily fluid into the fluid reservoir via the inlet adapter; and
a volume indicator coupled to the housing and configured to transition from a first state in which an arm of the volume indicator is in a first position relative to the housing to a second state in which the arm of the volume indicator is in a second position relative to the housing, the volume indicator being in the second state in response to a predetermined volume of bodily fluid being transferred into the fluid reservoir,
the predetermined volume being less than the second volume of the fluid reservoir, the volume indicator in the second state configured to be brought into contact with a portion of the actuator to at least temporarily stop the plunger from being moved proximally toward the second position.

2. The apparatus of claim 1, wherein the volume indicator in the second state is configured to provide an indication to the user associated with the predetermined volume of bodily fluid being transferred into the fluid reservoir.

3. The apparatus of claim 1, wherein the arm of the volume indicator is configured to rotate between the first position and the second position.

4. The apparatus of claim 1, wherein after the predetermined volume of bodily fluid is transferred into the fluid reservoir, the volume indicator is configured to transition to a third state in which the plunger is allowed to be moved to the second position.

5. The apparatus of claim 1, wherein the first portion of the actuator is moved through a first range of motion when engaged by the user, the actuator configured to move the plunger through a second range of motion different from the first range of motion.

6. The apparatus of claim 1, wherein the actuator is configured to modulate a rate of motion of the plunger below a threshold as the plunger is moved from the first position to the second position.

7. The apparatus of claim 1, wherein the inlet adapter is configured to be removed from the housing after the predetermined volume of bodily fluid is transferred into the fluid reservoir to allow transfer of the predetermined volume to a sample bottle external to the housing via the port.

8. An apparatus, comprising:

a housing defining a fluid reservoir and including a port in fluid communication with the fluid reservoir;

an inlet adapter removably coupleable to the housing, the inlet adapter including a needle configured to place the port in fluid communication with a bodily fluid source when coupled to the housing;

an actuator including a plunger at least partially disposed within the housing and defining at least a part of the fluid reservoir, the actuator configured to move the plunger within the housing between a first position and a second position, the fluid reservoir having a first volume when the plunger is in the first position and a second volume greater than the first volume when the plunger is in the second position, an increase in a volume of the fluid reservoir operable to draw bodily fluid into the fluid reservoir via the inlet adapter, a volume indicator including an arm configured to transition from a first configuration to a second configuration in response to a portion of the actuator engaging the volume indicator as the actuator moves the plunger from the first position toward the second position, the arm being in the second configuration in response to a predetermined volume of bodily fluid being transferred into the fluid reservoir, the predetermined volume being less than the second volume, the arm in the second configuration is configured to be brought into contact with the portion of the actuator to at least temporarily stop the actuator from further moving the plunger proximally to place the plunger in the second position.

9. The apparatus of claim 8, wherein the arm in the second configuration is configured to provide an indication to a user associated with the predetermined volume of bodily fluid being transferred into the fluid reservoir.

10. The apparatus of claim 8, wherein after the predetermined volume of bodily fluid is transferred into the fluid reservoir, the volume indicator is configured to transition to a third configuration in which the plunger is allowed to be move to the second position.

11. The apparatus of claim 8, wherein the actuator is moved through a first range of motion when engaged by a user, the actuator configured to move the plunger through a second range of motion different from the first range of motion.

12. The apparatus of claim 8, wherein the actuator is configured to modulate a rate of motion of the plunger below a threshold as the plunger is moved from the first position to the second position.

13. The apparatus of claim 8, wherein the inlet adapter is configured to be removed from the housing after the predetermined volume of bodily fluid is transferred into the fluid reservoir to allow transfer of the predetermined volume to a sample bottle external to the housing via the port.

14. An apparatus, comprising:

a housing defining a fluid reservoir and including a port in fluid communication with the fluid reservoir, an inlet adapter removably coupleable to the housing, the inlet adapter including a needle configured to place the port in fluid communication with a bodily fluid source when coupled to the housing;

an actuator including a plunger at least partially disposed within the housing and defining at least a part of the fluid reservoir, the actuator configured to move the plunger within the housing between a first position and a second position, the fluid reservoir having a first volume when the plunger is in the first position and a second volume greater than the first volume when the plunger is in the second position, an increase in a volume of the fluid reservoir operable to draw bodily fluid into the fluid reservoir via the inlet adapter, a volume indicator including an arm, the arm separate from the actuator and configured to move through a portion of the housing as the actuator moves the plunger proximally from the first position toward the second position, the arm configured to move relative to the actuator as the volume indicator transitions from a first configuration to a second configuration, the volume indicator in the second configuration configured such that the arm indicates transfer of a predetermined volume of bodily fluid into the fluid reservoir.

15. The apparatus of claim 14, wherein a portion of the volume indicator is configured to at least temporarily stop the plunger from moving further toward the second position when the volume indicator is in the second configuration.

16. The apparatus of claim 14, wherein after the predetermined volume of bodily fluid is transferred into the fluid reservoir, the volume indicator is configured to transition to a third configuration in which the plunger is allowed to be moved toward the second position.

17. The apparatus of claim 14, wherein the actuator is moved through a first range of motion when engaged by a user, the actuator configured to move the plunger through a second range of motion different from the first range of motion.

18. The apparatus of claim 14, wherein the actuator is configured to modulate a rate of motion of the plunger below a threshold as the plunger is moved from the first position to the second position.

19. The apparatus of claim 14, wherein the inlet adapter is configured to be removed from the housing after the predetermined volume of bodily fluid is transferred into the fluid reservoir to allow transfer of the predetermined volume to a sample bottle external to the housing via the port.

* * * * *